(12) United States Patent
Simpkin et al.

(10) Patent No.: US 10,066,993 B2
(45) Date of Patent: Sep. 4, 2018

(54) SPECTROSCOPIC ANALYSIS

(71) Applicant: KLEIN MEDICAL LIMITED, Auckland (NZ)

(72) Inventors: Raymond Andrew Simpkin, Auckland (NZ); Donal Paul Krouse, Wellington (NZ); Bryan James Smith, Auckland (NZ)

(73) Assignee: Klein Medical Limited, Auckland (NZ)

( * ) Notice: Subject to any disclaimer, the term of this patent is extended or adjusted under 35 U.S.C. 154(b) by 0 days.

(21) Appl. No.: 15/620,693

(22) Filed: Jun. 12, 2017

(65) Prior Publication Data

US 2018/0017442 A1  Jan. 18, 2018

Related U.S. Application Data

(63) Continuation of application No. 15/165,866, filed on May 26, 2016, now abandoned, which is a
(Continued)

(51) Int. Cl.
*G01J 5/02* (2006.01)
*G01J 3/10* (2006.01)
(Continued)

(52) U.S. Cl.
CPC .......... *G01J 3/108* (2013.01); *G01J 3/0297* (2013.01); *G01N 21/274* (2013.01);
(Continued)

(58) Field of Classification Search
CPC ...... G01J 3/10; G01J 3/28; G01J 3/42; G01N 2021/3133; G01N 2021/3144; G01N 2021/3155; G01N 21/359
See application file for complete search history.

(56) References Cited

U.S. PATENT DOCUMENTS 4,158,505 A  6/1979  Mathisen et al.
4,297,035 A  10/1981  Bjorklund
(Continued)

FOREIGN PATENT DOCUMENTS

EP  0025491 B1  1/1986
EP  1545659 B1  7/2008
(Continued)

OTHER PUBLICATIONS

U.S. Appl. No. 15/377,914, filed Dec. 13, 2016, Krouse et al.
(Continued)

*Primary Examiner* — Kiho Kim
(74) *Attorney, Agent, or Firm* — Knobbe, Martens, Olson & Bear LLP

(57) ABSTRACT

A method and analyser for identifying or verifying or otherwise characterising a sample comprising: using or having an electromagnetic radiation source for emitting electromagnetic radiation in at least one beam at a sample, the electromagnetic radiation comprising at least two different wavelengths, using or having a sample detector that detects affected electromagnetic radiation resulting from the emitted electromagnetic radiation affected by the sample and provides output representing the detected affected radiation, and using or having a processor for determining sample coefficients from the output, and identifying or verifying or otherwise characterising the sample using the sample coefficients and training coefficients determined from training samples, wherein the coefficients reduce sensitivity to a sample retainer variation and/or are independent of concentration.

6 Claims, 21 Drawing Sheets

Related U.S. Application Data continuation of application No. 14/409,450, filed as application No. PCT/NZ2013/000107 on Jun. 19, 2013, now Pat. No. 9,354,165.

(60) Provisional application No. 61/661,573, filed on Jun. 19, 2012.

(51) Int. Cl.

| | | |
|---|---|---|
| *G01N 21/3577* | (2014.01) | |
| *G01N 21/27* | (2006.01) | |
| *G01J 3/02* | (2006.01) | |
| *G01N 21/359* | (2014.01) | |
| *G01J 3/28* | (2006.01) | |

(52) U.S. Cl.
CPC ....... *G01N 21/359* (2013.01); *G01N 21/3577* (2013.01); *G01J 3/28* (2013.01); *G01N 2201/0691* (2013.01)

(56) References Cited

U.S. PATENT DOCUMENTS

| | | | |
|---|---|---|---|
| 4,805,623 A | 2/1989 | Jobsis | |
| 4,832,491 A | 5/1989 | Sharpe et al. | |
| 5,187,368 A | 2/1993 | Galante et al. | |
| 5,345,395 A | 9/1994 | Griner | |
| 5,355,880 A | 10/1994 | Thomas et al. | |
| 5,357,343 A | 10/1994 | Lowne et al. | |
| 5,437,076 A | 8/1995 | Vasquez | |
| 5,568,400 A * | 10/1996 | Stark ................... | G01J 3/28 702/191 |
| 5,602,647 A | 2/1997 | Xu et al. | |
| 5,647,359 A | 7/1997 | Kohno et al. | |
| 5,920,393 A | 7/1999 | Kaplan | |
| 6,483,589 B1 | 11/2002 | Suzuki et al. | |
| 6,504,616 B1 * | 1/2003 | Haber ................... | G01J 3/26 356/480 |
| 6,643,016 B2 | 11/2003 | Garver et al. | |
| 6,771,369 B2 | 8/2004 | Rzasa et al. | |
| 6,847,899 B2 | 1/2005 | Allgeyer | |
| 6,950,639 B2 | 9/2005 | Gogolla et al. | |
| 6,973,158 B2 | 12/2005 | Besson | |
| 7,006,214 B2 | 2/2006 | Rzasa et al. | |
| 7,154,599 B2 | 12/2006 | Adams et al. | |
| 7,218,395 B2 | 5/2007 | Kaye et al. | |
| 7,417,729 B2 | 8/2008 | Greenwald | |
| 7,460,226 B2 | 12/2008 | Klein | |
| 7,764,372 B2 | 7/2010 | Moran, Jr. et al. | |
| 8,512,279 B2 | 8/2013 | Klein | |
| 9,354,165 B2 | 5/2016 | Simpkin et al. | |
| 2002/0072661 A1 | 6/2002 | Wiesmann et al. | |
| 2003/0020433 A1 | 1/2003 | Knish et al. | |
| 2003/0204330 A1 | 10/2003 | Allgeyer | |
| 2005/0099624 A1 | 5/2005 | Staehr et al. | |
| 2005/0099632 A1 | 5/2005 | Harper | |
| 2005/0162653 A1 | 7/2005 | Carver et al. | |
| 2006/0106293 A1 | 5/2006 | Fantini | |
| 2007/0103678 A1 | 5/2007 | Sterling et al. | |
| 2007/0142777 A1 | 6/2007 | Klein | |
| 2007/0159636 A1 | 7/2007 | Jayaraman | |
| 2007/0182960 A1 | 8/2007 | Jayaraman | |
| 2007/0201025 A1 | 8/2007 | Greenwald | |
| 2007/0228280 A1 | 10/2007 | Mueller | |
| 2008/0218733 A1 | 9/2008 | Benes | |
| 2008/0221412 A1 * | 9/2008 | Baker ................... | A61B 5/0059 600/310 |
| 2009/0097025 A1 | 4/2009 | Iddan | |
| 2009/0166539 A1 * | 7/2009 | Ruan ................... | G01T 1/362 250/361 R |
| 2009/0177407 A1 | 7/2009 | Lennernas | |
| 2009/0213381 A1 | 8/2009 | Appel et al. | |
| 2010/0159609 A1 | 6/2010 | Trygstad et al. | |
| 2010/0208261 A1 | 8/2010 | Sens et al. | |
| 2011/0019183 A1 | 1/2011 | Ukon et al. | |
| 2012/0010477 A1 * | 1/2012 | Amano ................. | A61B 5/0075 600/301 |
| 2012/0143142 A1 | 6/2012 | Klein | |
| 2013/0211218 A1 * | 8/2013 | Suzuki ................ | A61B 5/1455 600/328 |
| 2013/0265566 A1 | 10/2013 | Smith et al. | |
| 2013/0345640 A1 | 12/2013 | Klein | |
| 2014/0246591 A1 | 9/2014 | Krouse et al. | |
| 2016/0131572 A1 | 5/2016 | Klein | |
| 2016/0265972 A1 | 9/2016 | Simpkin et al. | |
| 2016/0320295 A1 | 11/2016 | Smith et al. | |

FOREIGN PATENT DOCUMENTS

| | | | |
|---|---|---|---|
| EP | 2656666 A2 | 10/2013 | |
| JP | 2004535297 A | 11/2004 | |
| JP | 4566743 B2 | 10/2010 | |
| JP | 5943352 B2 * | 7/2016 | |
| WO | WO 2003/079267 | 9/2003 | |
| WO | WO 2003/106981 | 12/2003 | |
| WO | WO 2004/033003 | 4/2004 | |
| WO | WO 2005/046766 | 5/2005 | |
| WO | WO 2005/067110 | 7/2005 | |
| WO | WO 2012/138236 | 10/2012 | |

OTHER PUBLICATIONS

International Search Report; PCT/NZ2013/000107; dated Sep. 19, 2013; 3 pages.

Nagali et al., "Design of a diode-laser sensor to monitor water vapor in high-pressure combustion gases," Dec. 20, 1997, Applied Optics, vol. 36, pp. 9518-9527.

* cited by examiner

FIGURE 15

SPECTROSCOPIC ANALYSIS

FIELD OF THE INVENTION

The present invention relates to a spectroscopic analyser, such as a spectrophotometer, for verifying and/or identifying or otherwise analysing drugs, blood or other substances.

BACKGROUND OF THE INVENTION

Spectroscopy, for example through the use of a spectroscopic analyser such as a spectrophotometer, can be used to analyse substances. For example, by directing incident radiation towards a sample, and analysing the spectral nature of the affected radiation, it can be possible to gain an indication of the nature of the sample.

However, such analysers often provide inaccurate analysis. Accurately discriminating between different substances can be difficult.

SUMMARY OF INVENTION

It is an object of the present invention to provide an analyser and/or method for verifying or identifying or otherwise characterising a drug or other substances using spectroscopy.

The embodiments described in the present specification are directed towards drug characterisation but the invention is not limited to just characterising drugs. Those skilled in the art will appreciate that the disclosure herein can be applied to characterisation of other substances also.

In one aspect the present invention may be said to consist in an analyser for identifying or verifying or otherwise characterising a sample comprising: an electromagnetic radiation source for emitting electromagnetic radiation in at least one beam at a sample, the electromagnetic radiation comprising at least two different wavelengths, a sample detector that detects affected electromagnetic radiation resulting from the emitted electromagnetic radiation affected by the sample and provides output representing the detected affected radiation, and a processor for determining sample coefficients from the output, and identifying or verifying or otherwise characterising the sample using the sample coefficients and training coefficients determined from training samples.

Preferably the sample detector output represents intensities detected by the detector at the at least two wavelengths, and wherein determining the sample coefficients comprises determining and using a fractional spectral intensity at each wavelength.

Preferably the analyser further comprises a reference detector for detecting reference electromagnetic radiation at the at least two wavelengths that provides output representing intensities detected at the at least two wavelengths, and the fractional spectral intensity at each wavelength is a normalised fractional spectral intensity using the output from the reference detector.

Preferably the analyser is used on a plurality of training samples to obtain from the sample detector training output for a plurality of training samples representing intensities detected by the detector at the at least two wavelengths, and wherein the processor is configured to determine the training coefficients by determining and using a fractional spectral intensity at each wavelength of the training output.

Preferably the fractional spectral intensity is a normalised fractional spectral intensity using output from a reference detector.

Preferably the fractional intensity is defined as the proportion of transmitted light measured at a wavelength referenced to the sum of intensities over all the at least two wavelengths.

Preferably the normalised spectral intensity at each wavelength is determined in the processor using:

$$g_m = \frac{f_m}{\Sigma f_m}$$

Where: $f_m$ is an electromagnetic radiation intensity (or some parameter related to it—processed or unprocessed) detected at the $m^{th}$ wavelength, and preferably the intensity $f_m$ is a ratio of (optionally an average of) sample intensity(ies) to (optionally an average of) reference intensity(ies) or of (optionally an average of) training intensity(ies) to (optionally an average of) reference intensity(ies) as appropriate, and $\Sigma f_m$ is the sum of intensities over all of the at least two wavelengths.

Preferably the sample and/or training samples comprise a substance in a dilutant with a concentration and the sample coefficients and/or training coefficients are independent of the concentration.

Preferably each sample coefficient is determined by:

$$y_m^B = \frac{s_m^B}{\sqrt{\Sigma_m (s_m^B)^2}} \equiv \frac{g_m^B(x) - \overline{g_m^o}}{\Sigma_m (g_m^B(x) - \overline{g_m^o})^2}$$

Where $g_m^B(x) - \overline{g_m^0} = s_m^B x$ (preferably being a slope or difference between the undiluted substance and a dilutant)
X is the concentration of the substance in the dilutant
B denoting blind test sample $g_m^B(x)$, is the fractional spectral intensity of the sample with unknown concentration, and $\overline{g_m^0}$ is the fractional spectral intensity of the dilutant.

Preferably each training coefficient is determined by:

$$y_m = \frac{s_m}{\sqrt{\Sigma_m s_m^2}}$$

where $s_m = \overline{g_m} - \overline{g_m^0}$ (preferably being a slope or difference between the undiluted substance and a dilutant)
$\overline{g_m}$ is the fractional spectral intensity of the undiluted sample (being the undiluted substance), and
$\overline{g_m^0}$ is the fractional spectral intensity of the dilutant.

Preferably the analyser further comprises a modulator such that the emitted electromagnetic radiation at the sample is modulated electromagnetic radiation and prior to determining the sample coefficients the processor extracts the desired spectral component from the intensity at each of the at least two wavelengths to eliminate the dark current.

Preferably prior to determining the training coefficients the desired spectral components are extracted by the processor from the intensity at each of the at least two wavelengths to eliminate the dark current.

Preferably the processor extracts the desired spectral component by multiplying the output representing the detected affected modulated electromagnetic radiation by sine and cosine functions and integrating over the period of modulation oscillation to remove the dark current component.

Preferably the processor extracts the desired spectral component by conducting a Fourier Transform on the output representing the modulated detected affected radiation and removing the dark current component from the transformed output.

Preferably the analyser further comprises a temperature sensor to measure the temperature of the sample and provide temperature output to the processor, wherein the processor corrects the desired spectral components of the training coefficients at the at least two wavelengths to the temperate of the sample.

Preferably the temperature is corrected according to:

$$I(T_t) = I(T_b) + \frac{dI}{dT}\Delta T \quad (1)$$

Where,

I is the intensity of affected electromagnetic radiation detected by a detector at a particular wavelength for a sample, $T_t$ is the temperature of the training sample when the affected electromagnetic radiation was detected at that wavelength, $T_b$ is the temperature of the unknown sample when the affected electromagnetic radiation was detected at that wavelength, $\Delta T = T_t - T_b$ is the sample temperature difference between the training sample temperature and unknown sample temperature, and $$\frac{dI}{dT}$$

is the slope of the linear relationship of between measure intensity and temperature for a sample at a given wavelength.

Preferably to identify or verify or otherwise characterise the sample using the coefficients and training coefficients determined from training samples, the processor: determines or obtains a training value for each training sample based on a combination of weights for each training coefficient for each of the training samples, determines or obtains a sample value for the sample based on a combination of weights for each sample coefficient, indentifies or verifies or otherwise characterises the sample based on the relationship between the training and sample values.

Preferably further comprising the processor determining the concentration of the sample.

Preferably to determine the concentration of the sample the processor uses:

$$x = \frac{g_m^B(x) - \overline{g_m^0}}{s_m}$$

Where x is the concentration, and $g_m^B(x) - \overline{g_m^0} = s_m^B x$

X is the concentration of the substance in the dilutant
B denoting blind test sample
$g_m^B(x)$, is the fractional spectral intensity of the sample with unknown concentration, and
$\overline{g_m^0}$ is the fractional spectral intensity of the dilutant $s_m = \overline{g_m} - \overline{g_m^0}$ $\overline{g_m}$ is the fractional spectral intensity of the undiluted sample (being the undiluted substance), and
$\overline{g_m^0}$ is the fractional spectral intensity of the dilutant.

Preferably each wavelength or at least two of the wavelengths is between substantially 1300 nm and 2000 nm, and each wavelength or at least two of the wavelengths is in the vicinity of the wavelength(s) of (or within a region spanning) a spectral characteristic in the liquid spectrum between substantially 1300 nm and 2000 nm.

Preferably the electromagnetic radiation comprises a plurality of electromagnetic radiation beams, each beam having a different wavelength.

Preferably the source is a laser comprising a photodetector, wherein the photodetector is the reference detector.

Preferably the liquid is water, there are six electromagnetic radiation beams and the wavelengths are substantially 1350 nm, 1450 nm, 1550 nm, 1650 nm, 1750 nm and 1850 nm, and optionally wherein 1450 nm is the anchor wavelength.

Preferably the sample is in an intravenous delivery device such as an IV infusions set or syringe, or other receptacle such as a test-cell, test-tube, flow cell or the like.

In another aspect the present invention may be said to consist in a method for identifying or verifying or otherwise characterising a sample comprising: emitting electromagnetic radiation in at least one beam at a sample, the electromagnetic radiation comprising at least two different wavelengths, detecting affected electromagnetic radiation resulting from the emitted electromagnetic radiation affected by the sample and providing detected output representing the detected affected radiation, determining sample coefficients from the output, and identifying or verifying or otherwise characterising the sample using the sample coefficients and training coefficients determined from training samples.

Preferably the detected output represents intensities detected at the at least two wavelengths, and wherein determining the sample coefficients comprises determining and using a fractional spectral intensity at each wavelength.

Preferably the method further comprises detecting reference electromagnetic radiation at the at least two wavelengths and providing output representing intensities detected at the at least two wavelengths, and the fractional spectral intensity at each wavelength is a normalised fractional spectral intensity using the output from the reference detector.

Preferably the method further comprises: for a plurality of training samples, emitting electromagnetic radiation in at least one beam at each training sample, the electromagnetic radiation comprising at least two different wavelengths, for each training sample, detecting affected electromagnetic radiation resulting from the emitted electromagnetic radiation affected by the sample and providing detected output representing the detected affected radiation, for each sample, determining training coefficients from the output by determining and using a fractional spectral intensity at each wavelength of the training output.

Preferably the fractional spectral intensity is a normalised fractional spectral intensity using output from a reference detector.

Preferably the fractional intensity is defined as the proportion of transmitted light measured at a wavelength referenced to the sum of intensities over all the at least two wavelengths.

Preferably the normalised spectral intensity at each wavelength is determined by:

$$g_m = \frac{f_m}{\Sigma f_m}$$

Where: $f_m$ is an electromagnetic radiation intensity (or some parameter related to it—processed or unprocessed) detected at the $m^{th}$ wavelength, and preferably the intensity $f_m$ is a ratio of (optionally an average of) sample intensity(ies) to (optionally an average of) reference intensity(ies) or of (optionally an average of) training intensity(ies) to (optionally an average of) reference intensity(ies) as appropriate, and $\Sigma f_m$ is the sum of intensities over all of the at least two wavelengths.

Preferably the sample and/or training samples comprise a substance in a dilutant with a concentration and the sample coefficients and/or training coefficients are independent of the concentration.

Preferably each sample coefficient is determined by:

$$y_m^B = \frac{s_m^B}{\sqrt{\Sigma_m (s_m^B)^2}} \equiv \frac{g_m^B(x) - \overline{g_m^o}}{\Sigma_m (g_m^B(x) - \overline{g_m^o})^2}$$

Where $g_m^B(x) - \overline{g_m^0} = s_m^B x$ (preferably being a slope or difference between the undiluted substance and a dilutant)
X is the concentration of the substance in the dilutant
B denoting blind test sample
$g_m^B(x)$, is the fractional spectral intensity of the sample with unknown concentration, and
$\overline{g_m^0}$ is the fractional spectral intensity of the dilutant.

Preferably each training coefficient is determined by:

$$y_m = \frac{s_m}{\sqrt{\Sigma_m s_m^2}}$$

where $s_m = \overline{g_m} - \overline{g_m^0}$ (preferably being a slope or difference between the undiluted substance and a dilutant)
$\overline{g_m}$ is the fractional spectral intensity of the undiluted sample (being the undiluted substance), and
$\overline{g_m^0}$ is the fractional spectral intensity of the dilutant.

Preferably the emitted electromagnetic radiation at the sample is modulated electromagnetic radiation and prior to determining the sample coefficients the desired spectral component is extracted from the intensity at each of the at least two wavelengths to eliminate the dark current.

Preferably prior to determining the training coefficients the desired spectral components are extracted from the intensity at each of the at least two wavelengths to eliminate the dark current.

Preferably the desired spectral component is extracted by multiplying the output representing the detected affected modulated electromagnetic radiation by sine and cosine functions and integrating over the period of modulation oscillation to remove the dark current component.

Preferably the desired spectral component is extracted by conducting a Fourier Transform on the output representing the modulated detected affected radiation and removing the dark current component from the transformed output.

Preferably the method further comprises measuring the temperature of the sample and provide temperature output to the processor, and correcting the desired spectral components of the training coefficients at the at least two wavelengths to the temperate of the sample.

Preferably the temperature is corrected according to:

$$I(T_t) = I(T_b) + \frac{dI}{dT} \Delta T \tag{1}$$

Where,
I is the intensity of affected electromagnetic radiation detected by a detector at a particular wavelength for a sample,
$T_t$ is the temperature of the training sample when the affected electromagnetic radiation was detected at that wavelength,
$T_b$ is the temperature of the unknown sample when the affected electromagnetic radiation was detected at that wavelength,
$\Delta T = T_t - T_b$ is the sample temperature difference between the training sample temperature and unknown sample temperature, and $$\frac{dI}{dT}$$

is the slope of the linear relationship of between measure intensity and temperature for a sample at a given wavelength.

Preferably to identify or verify or otherwise characterise the sample using the coefficients and training coefficients determined from training samples, comprises: determining or obtaining a training value for each training sample based on a combination of weights for each training coefficient for each of the training samples, determining or obtaining a sample value for the sample based on a combination of weights for each sample coefficient, identifying or verifying or otherwise characterising the sample based on the relationship between the training and sample values.

Preferably the method further comprises determining the concentration of the sample.

Preferably determining the concentration of the sample the processor uses:

$$x = \frac{g_m^B(x) - \overline{g_m^o}}{s_m} \tag{7}$$

Where x is the concentration, and

Where $g_m^B(x) - \overline{g_m^0} = s_m^B x$

X is the concentration of the substance in the dilutant
B denoting blind test sample
$g_m^B(x)$, is the fractional spectral intensity of the sample with unknown concentration, and
$\overline{g_m^0}$ is the fractional spectral intensity of the dilutant $s_m = \overline{g_m} - \overline{g_m^0}$ $\overline{g_m}$ is the fractional spectral intensity of the undiluted sample (being the undiluted substance), and
$\overline{g_m^0}$ is the fractional spectral intensity of the dilutant.

Preferably each wavelength or at least two of the wavelengths is between substantially 1300 nm and 2000 nm, and each wavelength or at least two of the wavelengths is in the vicinity of the wavelength(s) of (or within a region spanning) a spectral characteristic in the liquid spectrum between substantially 1300 nm and 2000 nm.

Preferably the electromagnetic radiation comprises a plurality of electromagnetic radiation beams, each beam having a different wavelength.

Preferably the liquid is water, there are six electromagnetic radiation beams and the wavelengths are substantially 1350 nm, 1450 nm, 1550, nm, 1650, nm, 1750 nm and 1850 nm, and optionally wherein 1450 nm is the anchor wavelength.

Preferably the sample is in an intravenous delivery device such as an IV infusions set or syringe, or other receptacle such as a test-cell, test-tube, flow cell or the like.

In another aspect the present invention may be said to consist in a method for identifying or verifying or otherwise characterising a sample comprising: emitting electromagnetic radiation in at least one beam at a sample, the electromagnetic radiation comprising at least two different wavelengths, detecting the emitted electromagnetic radiation at each wavelength and providing detected output representing the emitted electromagnetic radiation being reference intensity detected at each wavelength, detecting affected electromagnetic radiation resulting from the emitted electromagnetic radiation affected by the sample and providing detected output representing the detected affected radiation being output intensity detected at each wavelength, measuring the temperature of the sample determining sample coefficients from the output, and identifying or verifying or otherwise characterising the sample using the sample coefficients and training coefficients determined from training samples, wherein determining the sample coefficients comprises: eliminating dark current from the output of the reference and output intensities, determining fractional spectral intensities from the reference and output intensities', determining a concentration independent coefficient from the fractional spectral intensities, wherein the training coefficients have be determined from data temperature corrected to the temperature of the sample.

In another aspect the present invention may be said to consist in an analyser for identifying or verifying or otherwise characterising a sample comprising: an electromagnetic radiation source for emitting electromagnetic radiation in at least one beam at a sample, the electromagnetic radiation comprising at least two different wavelengths, a sample detector that detects affected electromagnetic radiation resulting from the emitted electromagnetic radiation affected by the sample and provides output representing the detected affected radiation, and a processor for determining sample coefficients from the output, and identifying or verifying or otherwise characterising the sample using the sample coefficients and training coefficients determined from training samples, wherein the sample coefficients are found from the slope/difference of normalised spectral intensity at a particular wavelength normalised with respect to the root-sum-of-squares slope/difference of normalised spectral intensity taken over all wavelengths, each slope/difference of normalised spectral intensity being obtained from detector output for the sample in undiluted form and a dilutant for a particular wavelength, and each normalised spectral intensity being found from the detected intensity at a particular wavelength over the sum of detected intensities for all wavelengths for a sample.

The wavelengths relate to the test wavelengths.

In another aspect the present invention may be said to consist in an analyser for identifying or verifying a liquid based drug sample comprising: an electromagnetic radiation source for emitting electromagnetic radiation in at least one beam at a sample, the electromagnetic radiation comprising at least two different wavelengths, a sample detector that detects affected electromagnetic radiation resulting from the emitted electromagnetic radiation affected by the sample and provides output representing the detected affected radiation, and a processor for identifying or verifying the sample from the detector output representing the detected affected electromagnetic radiation, wherein each wavelength or at least two of the wavelengths is between substantially 1300 nm and 2000 nm, and each wavelength or at least two of the wavelengths is in the vicinity of the wavelength(s) of (or within a region spanning) a spectral characteristic in the liquid spectrum between substantially 1300 nm and 2000 nm.

Preferably the electromagnetic radiation comprises a plurality of electromagnetic radiation beams, each beam having a different wavelength.

Preferably verifying or identifying the drug sample is against comparison data for one of a set of n drugs, and wherein the electromagnetic radiation comprises at least $\log_2 n$ different wavelengths in one or more beams.

Preferably the different wavelengths span or capture a plurality of at least some of the spectral characteristics in the liquid spectrum between 1300 nm and 2000 nm.

Preferably the liquid spectrum comprises two or more spectral characteristics, and wherein: each spectral characteristic falls in or spans a region of the liquid spectrum, each wavelength falls within one of the regions.

Preferably each region is defined by a wavelength range.

Preferably the spectral characteristics comprise peaks, troughs, inflections, stable points or regions plateaus, knees and/or slopes of the liquid spectrum.

Preferably the liquid is water and comprises spectral characteristics falling in the following regions of the water spectrum: a first region between 1300 nm and 1400 nm, a second region between 1400 nm and 1500 nm, a third region between 1500 nm and 1600 nm, a fourth region between 1600 nm and 1700 nm, a fifth region between 1700 nm and 1800 nm, and a sixth region between 1800 nm and 200 nm.

Preferably the electromagnetic radiation has an anchor wavelength in the vicinity of the wavelength(s) of (or within a region spanning) a stable region in the liquid spectrum.

Preferably the each wavelength further corresponds to a wavelength produced by a source that is readily/cheaply obtainable.

Preferably the source is a plurality of lasers, each laser configured to emit an electromagnetic radiation beam at a fixed or tuneable wavelength.

Preferably comprises a modulator for modulating the electromagnetic radiation beam(s) emitted at the sample resulting in detected affected radiation detected by the sample detector that is modulated wherein the processor as part of identifying or verifying the sample from the output from the detector removes the dark current component from the output representing the detected affected modulated electromagnetic radiation Optionally the processor removes the dark current component by multiplying the output representing the detected affected modulated electromagnetic radiation by sine and cosine functions and integrating over the period of modulation oscillation to remove the dark current component.

Optionally the processor removes the dark current component by conducting a Fourier Transform on the output representing the modulated detected affected radiation and removing the dark current component from the transformed.

Preferably the processor identifies or verifies the drug sample using reference information. Preferably the affected electromagnetic radiation at or the electromagnetic radiation beam comprising the anchor wavelength provides the reference information.

Preferably the analyser further comprises: an optical device for directing the plurality of electromagnetic radiation beams to a reference sample, a reference detector that detects affected electromagnetic radiation beams affected by the reference sample to obtain the reference information and that passes the reference information to the processor.

Preferably the detector and/or source are temperature compensated to provide temperature stability, preferably using thermistors and peltier devices in a closed loop system.

Preferably each electromagnetic radiation beam is a high intensity narrowband light beam.

Preferably the detector is a broadband photodiode that is biased to have a response corresponding to the wavelength/s of the affected radiation.

Preferably the emitted electromagnetic radiation beams from the plurality of lasers are directed to a sample path by one or more of: a carousel or carriage device to position the laser beams in the sample path, or a prism, diffraction grating, beam splitter or other optical device to redirect a radiation beam along the sample path.

Preferably the processor receives: output representing the affected electromagnetic radiation from the drug sample which provides drug sample information, and optionally reference information for each wavelength, and the processor: determines a representative value of the drug sample information using that information and optionally reference information for each wavelength.

Preferably the sample information and reference information correlate intensity and wavelength for each electromagnetic radiation beam.

Preferably the representative value corresponds to a best fit between the sample information and optionally the reference information.

Preferably the representative value for the electromagnetic radiation beam for each wavelength is compared to stored values to verify or identify the drug sample.

Preferably the liquid is water, there are six electromagnetic radiation beams and the wavelengths are substantially 1350 nm, 1450 nm, 1550, nm, 1650, nm, 1750 nm and 1850 nm, and optionally wherein 1450 nm is the anchor wavelength.

Preferably the sample is in an intravenous delivery device such as an IV infusions set or syringe, or other receptacle such as a test-cell, test-tube, flow cell or the like.

Preferably the source is a laser comprising a photodetector, wherein the photodetector detects electromagnetic radiation from the laser and outputs the reference information.

In another aspect the present invention may be said to consist in a method for identifying or verifying or otherwise characterising a liquid based drug sample comprising: emitting electromagnetic radiation in at least one beam at a sample, the electromagnetic radiation comprising at least two different wavelengths, detecting affected electromagnetic radiation resulting from the emitted electromagnetic radiation affected by the sample and providing output representing the detected affected radiation, and identifying or verifying the sample from the output representing detected affected electromagnetic radiation, wherein each wavelength or at least two of the wavelengths is between substantially 1300 nm and 2000 nm, and each wavelength or at least two of the wavelengths is in the vicinity of the wavelength(s) of (or within a region spanning) a spectral characteristic in the liquid spectrum between substantially 1300 nm and 2000 nm.

Preferably the electromagnetic radiation comprises a plurality of electromagnetic radiation beams, each beam having a different wavelength.

Preferably verifying or identifying the drug sample is against comparison data for one of a set of n drugs, and wherein the electromagnetic radiation comprises at least $\log_2 n$ different wavelengths in one or more beams.

Preferably the different wavelengths span or capture a plurality of at least some of the spectral characteristics in the liquid spectrum between 1300 nm and 2000 nm.

Preferably the liquid spectrum comprises two or more spectral characteristics, and wherein: each spectral characteristic falls in or spans a region of the liquid spectrum, each wavelength falls within one of the regions.

Preferably each region is defined by a wavelength range.

Preferably the spectral characteristics comprise peaks, troughs, inflections, stable points or regions, plateaus, knees and/or slopes of the liquid spectrum.

Preferably the liquid is water and comprises spectral characteristics falling in the following regions of the water spectrum: a first region between 1300 nm and 1400 nm, a second region between 1400 nm and 1500 nm, a third region between 1500 nm and 1600 nm, a fourth region between 1600 nm and 1700 nm, a fifth region between 1700 nm and 1800 nm, and a sixth region between 1800 nm and 200 nm.

Preferably the electromagnetic radiation has an anchor wavelength in the vicinity of the wavelength(s) of (or within a region spanning) a stable region in the liquid spectrum.

Preferably each wavelength further corresponds to a wavelength produced by a source that is readily/cheaply obtainable.

Preferably the electromagnetic radiation is generated using a source comprising a plurality of lasers, each laser configured to emit an electromagnetic radiation beam at a fixed or tuneable wavelength.

Preferably wherein a modulator is used for modulating the electromagnetic radiation beams emitted at the sample resulting in detected affected radiation that is modulated, and wherein identifying or verifying the sample from the output from the output comprises removing the dark current component from the output representing the detected affected modulated electromagnetic radiation.

Optionally removing the dark current component comprises multiplying the output representing the detected affected modulated electromagnetic radiation by sine and cosine functions and integrating over the period of modulation oscillation to remove the dark current component.

Optionally removing the dark current component comprises conducting a Fourier Transform on the output representing the modulated detected affected radiation and removing the dark current component from the transformed.

Preferably the identifying or verifying is carried out by a processor that identifies or verifies the drug sample using reference information.

Preferably the affected electromagnetic radiation at or the electromagnetic radiation beam comprising the anchor wavelength provides the reference information.

Preferably the method further comprises: directing the plurality of electromagnetic radiation beams to a reference sample using an optical device, detecting using a reference detector affected electromagnetic radiation beams affected by the reference sample to obtain the reference information and that passes the reference information to the processor.

Preferably the method further comprises temperature compensating the detector and/or source provide temperature stability, preferably using thermistors and peltier devices in a closed loop system.

Preferably each electromagnetic radiation beam is a high intensity narrowband light beam.

Preferably the detector is a broadband photodiode that is biased to have a response corresponding to the wavelength/s of the affected radiation.

Preferably the emitted electromagnetic radiation beams from the plurality of lasers are directed to a sample path by one or more of: a carousel or carriage device to position the laser beams in the sample path, or a prism, diffraction grating, beam splitter or other optical device to redirect a radiation beam along the sample path.

Preferably the processor receives: affected electromagnetic radiation from the drug sample which provides drug sample information, and optionally reference information for each wavelength, and the processor: determines a representative value of the drug sample information and optionally reference information for each wavelength.

Preferably the sample information and reference information correlate intensity and wavelength for each electromagnetic radiation beam.

Preferably the representative value corresponds to a best fit between the sample information and optionally the reference information.

Preferably the representative value for the electromagnetic radiation beam for each wavelength is compared to stored values to verify or identify the drug sample.

Preferably the liquid is water, there are six electromagnetic radiation beams and the wavelengths are substantially 1350 nm, 1450 nm, 1550, nm, 1650, nm, 1750 nm and 1850 nm, wherein 1450 nm is the anchor wavelength.

Preferably the sample is in an intravenous delivery device such as an IV infusions set or syringe, or other receptacle such as a test-cell, test-tube, flow cell or the like.

Preferably each laser comprises a photodetector, wherein the photodetector detects electromagnetic radiation from the laser and outputs the reference information.

In another aspect the present invention may be said to consist in an analyser for identifying or verifying or otherwise characterising a drug sample (or other substance) in a liquid carrier comprising: an electromagnetic radiation source for emitting electromagnetic radiation in at least one beam at a sample, the electromagnetic radiation comprising at least two different selected wavelengths, a sample detector that detects affected electromagnetic radiation resulting from the emitted electromagnetic radiation affected by the sample, and a processor for identifying or verifying the sample from the detected affected electromagnetic radiation, wherein each wavelength is selected to be in the vicinity of the wavelength(s) of (or within a region spanning) a spectral characteristic in the spectrum of the liquid carrier, each wavelength falling within an analysis range suitable for the liquid carrier.

In another aspect the present invention may be said to consist in a method for identifying or verifying or otherwise characterising a drug sample (or other substance) in a liquid carrier comprising: emitting electromagnetic radiation in at least one beam at a sample, the electromagnetic radiation comprising at least two different selected wavelengths, detecting affected electromagnetic radiation resulting from the emitted electromagnetic radiation affected by the sample, and identifying or verifying the sample from the detected affected electromagnetic radiation, wherein each wavelength is selected to be in the vicinity of the wavelength(s) of (or within a region spanning) a spectral characteristic in the spectrum of the liquid carrier, each wavelength falling within an analysis range suitable for the liquid carrier.

In another aspect the present invention may be said to consist in an analyser for identifying or verifying or otherwise characterising a liquid based drug sample (or other substance) comprising:
an electromagnetic radiation source for emitting electromagnetic radiation in at least one beam at a sample, the electromagnetic radiation comprising at least two different wavelengths, a sample detector that detects affected electromagnetic radiation resulting from the emitted electromagnetic radiation affected by the sample, and a processor for identifying or verifying the sample from the detected affected electromagnetic radiation, wherein each wavelength is falls in an analysis range that provides improved identification/verification for drugs in the liquid carrier, and each wavelength is in the vicinity of the wavelength(s) of (or within a region spanning) a spectral characteristic in the liquid spectrum in the analysis range.

In another aspect the present invention may be said to consist in a method for identifying or verifying or otherwise characterising a liquid based drug sample (or other substance) comprising: emitting electromagnetic radiation in at least one beam at a sample, the electromagnetic radiation comprising at least two different wavelengths, detecting affected electromagnetic radiation resulting from the emitted electromagnetic radiation affected by the sample, and identifying or verifying the sample from the detected affected electromagnetic radiation, wherein each wavelength is falls in an analysis range that provides improved identification/verification for drugs in the liquid carrier, and each wavelength is in the vicinity of the wavelength(s) of (or within a region spanning) a spectral characteristic in the liquid spectrum in the analysis range.

In another aspect the present invention an analyser for identifying or verifying or otherwise characterising a liquid based drug sample comprising: an electromagnetic radiation source for emitting modulated electromagnetic radiation in at least one beam at a sample, the electromagnetic radiation comprising at least two different wavelengths, a sample detector that detects affected modulated electromagnetic radiation resulting from the emitted electromagnetic radiation affected by the sample and provides output representing the detected affected modulated radiation, and a processor for identifying or verifying the sample from the output representing detected affected modulated electromagnetic radiation including removing dark current from the output, wherein each wavelength or at least two of the wavelengths is between substantially 1300 nm and 2000 nm.

In another aspect the present invention a method for identifying or verifying or otherwise characterising a liquid based drug sample comprising: emitting modulated electromagnetic radiation in at least one beam at a sample, the electromagnetic radiation comprising at least two different wavelengths, detecting affected modulated electromagnetic radiation resulting from the emitted electromagnetic radiation affected by the sample and providing output representing the detected affected radiation, and identifying or verifying the sample from the output representing detected affected modulated electromagnetic radiation including removing dart current from the output, wherein each wavelength or at least two of the wavelengths is between substantially 1300 nm and 2000 nm.

In another aspect the present invention an analyser for identifying or verifying or otherwise characterising a liquid based drug sample comprising: an electromagnetic radiation source for emitting electromagnetic radiation in at least one beam at a sample, the electromagnetic radiation comprising at least two different wavelengths and for measuring the power of the emitted electromagnetic radiation, a sample detector that detects affected electromagnetic radiation resulting from the emitted electromagnetic radiation affected by the sample and provides output representing the detected affected radiation, and a processor for identifying or verifying the sample from the detector output representing the detected affected electromagnetic radiation including using the measured power of the emitted electromagnetic radiation, wherein each wavelength or at least two of the wavelengths is between substantially 1300 nm and 2000 nm, and each wavelength or at least two of the wavelengths is in the vicinity of the wavelength(s) of (or within a region spanning) a spectral characteristic in the liquid spectrum between substantially 1300 nm and 2000 nm.

In another aspect the present invention a method for identifying or verifying or otherwise characterising a liquid based drug sample comprising: emitting electromagnetic radiation in at least one beam at a sample, the electromagnetic radiation comprising at least two different wavelengths and measuring the power of the emitted electromagnetic radiation, detecting affected electromagnetic radiation resulting from the emitted electromagnetic radiation affected by the sample and providing output representing the detected affected radiation, and identifying or verifying the sample from the output representing detected affected electromagnetic radiation including using the measured power of the emitted electromagnetic radiation, wherein each wavelength or at least two of the wavelengths is between substantially 1300 nm and 2000 nm.

In another aspect the present invention a analyser for identifying or verifying or otherwise characterising a sample comprising: an electromagnetic radiation source for emitting electromagnetic radiation in at least one beam at a sample, the electromagnetic radiation comprising at least two different wavelengths, a sample detector that detects affected electromagnetic radiation resulting from the emitted electromagnetic radiation affected by the sample, and a processor for identifying or verifying the sample from the detected affected electromagnetic radiation, wherein each wavelength or at least two of the wavelengths is between substantially 1300 nm and 2000 nm.

Preferably the source is a plurality of lasers in a single package, each laser configured to emit an electromagnetic radiation beam at a fixed or tuneable wavelength.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

The term "comprising" as used in this specification means "consisting at least in part of". Related terms such as "comprise" and "comprised" are to be interpreted in the same manner.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

Preferred embodiments of the invention will be described with reference to the following drawings, of which:

FIG. 15 shows a matrix indicating verification for a set of sample drugs.

DETAILED DESCRIPTION OF THE PREFERRED EMBODIMENTS

Overview

Figure 1:
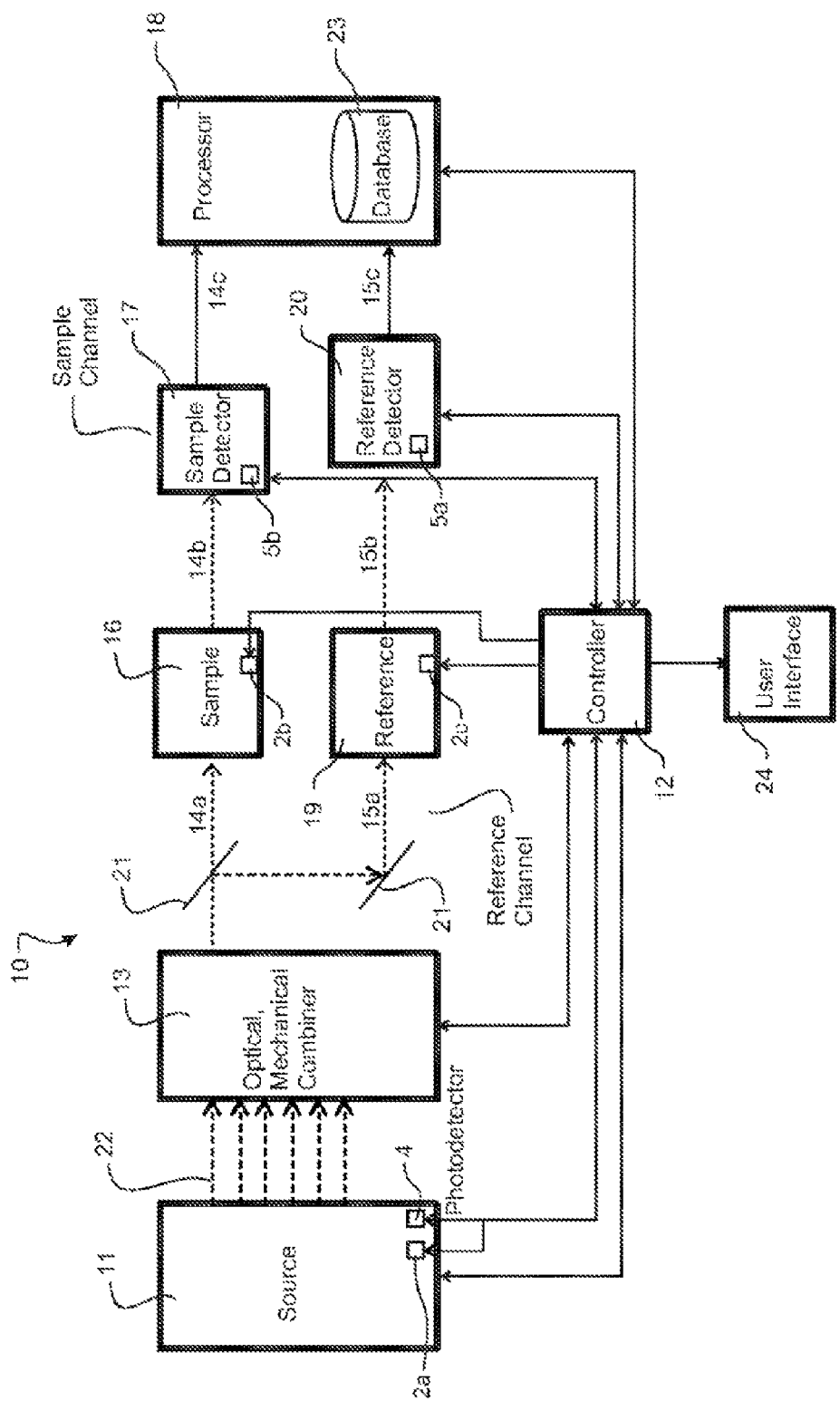
FIG. 1 shows in schematic form a spectroscopic analyser according to the present invention.

FIG. 1 shows an overview of a spectroscopic analyser 10 (for example, a spectrophotometer) according to the present invention for verifying or identifying (that is, analyse/characterise) drugs or other samples (e.g. blood, biological samples, etc.). The term "drug" should be interpreted broadly to cover any pharmaceutical or other medicament or substance for treating patients, which is clinician controlled 9 (e.g. through a hospital, prescription or pharmacy) or freely available. The analyser can be used for blind tests, wherein an unknown sample is analysed to be verified/identified or otherwise characterised. The analyser can also be used to obtain training data from test samples during a training process to assist in the later analysis of an unknown sample in a blind test.

The analyser (apparatus) 10 comprises a controller 12 that controls both physical control and processing aspects of operation. The analyser 10 comprises an electromagnetic radiation source 11 for generating and emitting electromagnetic radiation 22 with/at a plurality of wavelengths within a wavelength range. The source might also have a photodetector 4 or similar for control purposes. The electromagnetic radiation could take the form of a plurality of electromagnetic radiation beams at different wavelengths, or a single electromagnetic radiation beam comprising a plurality of wavelength components.

The term "wavelength" used for electromagnetic radiation output refers to a particular wavelength, such as 1300 nm. As will be appreciated, in practice, a source will not provide electromagnetic radiation output with a pure single wavelength—the output could contain components either side of the centre wavelength/peak. In this case, the term "wavelength" refers to the centre wavelength/peak of the electromagnetic radiation output, where the radiation output might also have a wavelength components either side of the centre wavelength, e.g. +/−30 nm, or +/−12 nm or even just a few nm (e.g. 2 nm for lasers) either side. Each such wavelength could be termed a "discrete" wavelength, as for practical purposes it is discrete, even if other components exist.

The electromagnetic radiation beams 22 could be visible light beams emitted from one or more lasers, for example. In one example, the electromagnetic radiation source ("source") 11 could be a single device that can be configured to generate and emit a plurality of electromagnetic radiation beams with different wavelengths in sequence or simultaneously, or that emits a single electromagnetic radiation beam with multiple wavelength components.

In another example, the source 11 could be a set of individual sources, each configured to generate and emit electromagnetic radiation beams 22 with a desired wavelength. The term "source" can refer to a single source or multiple sources making up a source. In each case, the source 11 might generate a fixed wavelength electromagnetic radiation beam(s), or it might be tuneable to emit an electromagnetic radiation beam(s) at one of a range of wavelengths. The source electromagnetic radiation might optionally be modulated as described later. Other examples could be envisaged by those skilled in the art also. The source can have an inbuilt or separate temperature sensor 2a (which may form part of the photodiode 4), such as a thermistor for detecting the operating temperature. The output can be passed to the processor 18.

Preferably, the source 11 is configured so that each electromagnetic radiation beam 22 with a corresponding wavelength(s) can be independently emitted in sequence. This might be achieved through using a single source that is tuned to emit electromagnetic radiation beams that sweep through a range of wavelengths. Alternatively, where a source comprises multiple electromagnetic radiation sources, each of which can be operated in turn, it might be achieved by each source becoming the "active" source—such as a single package comprising multiple lasers. So that the electromagnetic radiation beam of the active source is directed along the desired sample path 14a, each electromagnetic radiation beam output from the source can be arranged to hit a grating, mirror, prism or other optical apparatus 13 that redirects the beam from that source along the desired sample path 14a. In such arrangement, each electromagnetic radiation beam can be directed in sequence along the desired path as it is generated/activated. Alternatively, multiple electromagnetic radiation beams could be simultaneously directed along a beam path 14a, resulting in a single beam of electromagnetic radiation comprising a plurality of wavelength components. Alternatively, the sources could be arranged on a carousel or linear carriage (also represented by 13) that can be mechanically controlled to physically position each source to emit a radiation beam along the path 14a. These alternatives will be described further later. Other arrangements for redirecting a plurality of electromagnetic radiation beams from a source 11 along a desired path 14a could also be envisaged. The electromagnetic radiation beam directed along the path 14a can be termed the sample electromagnetic radiation beam.

The apparatus 10 comprises a sample/sample retainer 16 for holding a sample in the path 14a of the sample electromagnetic radiation beam. A non-contact infrared or other temperature sensor 71 is incorporated into or disposed near the sample retainer 16 to enable a measurement to be made of the temperature of the sample under test and the retainer. This could be the same or separate to the retainer temperature sensor 2b, 2c.

The sample retainer 16 could be a test-tube/test-tube holder, other type of test cell, part of an infusion pump/IV set, flow-cell, syringe or any other type of device for holding any of these or for holding a sample/substance in any manner. The sample could alternatively simply be placed in the path 14a. Any sample retainer allows for transmission of the electromagnetic radiation 22 to and through the sample. The sample is preferably (although not limited to) a liquid based drug. The liquid based sample could, for example be a water based drug, but it could also be another type of sample/substance in water or other liquid carrier. The use of "drug" in the embodiments below is for illustrative purposes only and it will be appreciated that the embodiments could be used for other types of samples. The term "sample" is used generally to indicate a substance for analysis (e.g. verification/identification) and is not necessarily restricted to a test sample/small portion of a larger amount of substance. For example, the sample could be an actual drug to be administered—not simply a (sample) portion of that drug to be administered. The apparatus 10 can be used in a clinical or other environment to verify/identify a drug prior to admission. In this case, the sample put in the apparatus 10 will be the actual drug being administered. The sample can be a training sample, or an unknown sample under test. The retainer in the sample and reference channels can have an inbuilt or separate temperature sensor, such as a thermistor, for detecting the retainer temperature, 2a, 2c and/or the sample. The output can be passed to the processor 18.

An electromagnetic radiation beam emitted along the path 14a provides incident electromagnetic radiation on a sample (substance) 16 placed in the path (e.g. in the sample retainer.) Any incident electromagnetic radiation beam 14a that reaches the sample 16 is affected by the sample (e.g. either by transmission through and/or reflection by the sample.) The affected (sample) electromagnetic radiation 14b that exits the sample 16 is affected electromagnetic radiation and contains spectral information regarding the sample.

Spectral information broadly means any information contained in affected electromagnetic radiation. For example, the affected electromagnetic radiation 14b comprises information about the intensity of the affected electromagnetic radiation at one wavelength of the incident radiation.

A sample detector 17 is placed in the affected electromagnetic radiation path 14b such that affected electromagnetic radiation 14b exiting the sample can be detected. The detector 17 can comprise, for example, one or more photodetectors. The detector 17 outputs information 14c in the form of data/a signal that represents or indicates spectral information of the sample 16—that is, the output represents the detected affected electromagnetic radiation. The detector output 14c could, for example represent or provide an indication of the electromagnetic intensity of the affected electromagnetic radiation incident on the detector—typically in the form of a voltage that is proportional to the intensity. It will be appreciated that while the output might not actually be the electromagnetic radiation intensity, it will have some relationship to it, such as being a signal with a voltage being proportional to the actual intensity. Use of the term "intensity" throughout this specification when referring to the detector output will be understood to not be limiting and could relate to any parameter relating to intensity. The detector 17 output 14c is passed through to a processor 18 that carries out a verification/identification algorithm in order to verify or identify or otherwise analyse the sample in the retainer. Pre-processing can optionally occur, although this is not essential; for example if a stable source is used such as a laser. The processor 18 can form part of the controller 12, or can be separate thereto. The processor 18 comprises or has access to a database 23 with reference/training/comparison data for verifying or identifying or otherwise analysing the sample. The database 23 is a datastore and can take any suitable form and use any suitable hardware (such as memory in the processor or an external or even remote hardware). It is not necessarily part of the processor 18, but is shown as such for simplicity. The path 14a, 14b, emitted and affected radiation and/or the sample/sample holder. 16 can be termed the "sample channel." The sample detector 16 and inputs to the processor 18 (and optionally the processor itself) can also form part of the sample channel.

Optionally there might also be a reference channel, in which the emitted electromagnetic radiation beam 14a incident on the sample 16 is split 21 or otherwise redirected along a reference path 15a towards another retainer 19 containing a reference sample/substance (or simply "reference") 19. A beam splitter 21 could be used to achieve this. The reference could be saline, for example. The reference sample retainer 19 could be any one of those retainers 16 mentioned with respect to the sample channel. Alternatively, the reference may have no retainer and/or sample and be for the purposes of measuring uninterrupted electromagnetic radiation. The reference channel, while shown as a separate channel, could in fact be the same as the sample channel, but reconfigured to remove the sample and/or retainer and place the appropriate reference sample (if any) in the electromagnetic radiation path. The reference electromagnetic radiation beam along the reference path 15a is incident on and affected by the reference sample 19 (if any) to produce affected (reference) electromagnetic radiation 15b which is incident on and detected by a reference detector 20. The reference detector 20 could be the same or different detector to that of the sample channel. In FIG. 1, the reference detector 20 is shown as an independent detector by way of example.

The reference detector 20 outputs information 15c in the form of data/a signal that represents or indicates spectral information 15c of the reference—that is, the output represents the detected affected electromagnetic radiation. The detector output 15c could, for example, represent the electromagnetic intensity of the affected electromagnetic radiation such as described earlier for the sample channel. The detector output 15c is passed through to the processor 18 that carries out a verification/identification algorithm in order to verify or identify the sample 16 in the retainer. Pre-processing can be carried out, although this is not essential if a stable source is used, such as a laser. The detector output 15c from the reference channel provides data from which to normalise and/or correct the sample channel data 14c. The reference channel might also comprise a neutral density filter prior to the sample. This attenuates the incident electromagnetic radiation in a manner to normalise the detected affected electromagnetic radiation, or otherwise modify it so that the output of the detector is at a suitable level to enable processing/comparison with the output of the detector on the sample channel.

In an alternative to the reference channel, optionally the output from a monitor diode 4 on the source could be used to provide reference data/output/signal/information from which to normalise and/or correct the sample channel data 14c. The output can be provided to the controller 12 and/or processor 18 The monitor diode could be a pre-existing detector on the source that measures power of the output electromagnetic radiation. In this case, the monitor diode could be considered a "reference detector" and in effect provide a reference channel.

Each electromagnetic radiation beam 22 has a wavelength (or has a plurality of wavelength components) that falls in the analysis range ("analysis region"), preferably of 1300-2000 manometers (nm). This region can nominally be termed "near infrared" or "NIR". This region provides useful spectral information for verifying or identifying drugs. The wavelength of each electromagnetic radiation beam 22 (or the wavelengths making up an electromagnetic beam) is preferably selected based on spectral characteristics (features) of the base liquid of the drug sample that fall within the analysis range. Such characteristics could be, for example, peaks, troughs, points of inflection, stable point or regions, plateaus, knees and/or slopes of that base liquid spectrum. Each wavelength selected is in the vicinity of (or within a region spanning) such a spectral characteristic. The position of a spectral characteristic could be defined by a nominal wavelength (of for example the centre wavelength of the characteristic) or a range of wavelengths defining a region spanning the characteristic.

Figure 2:
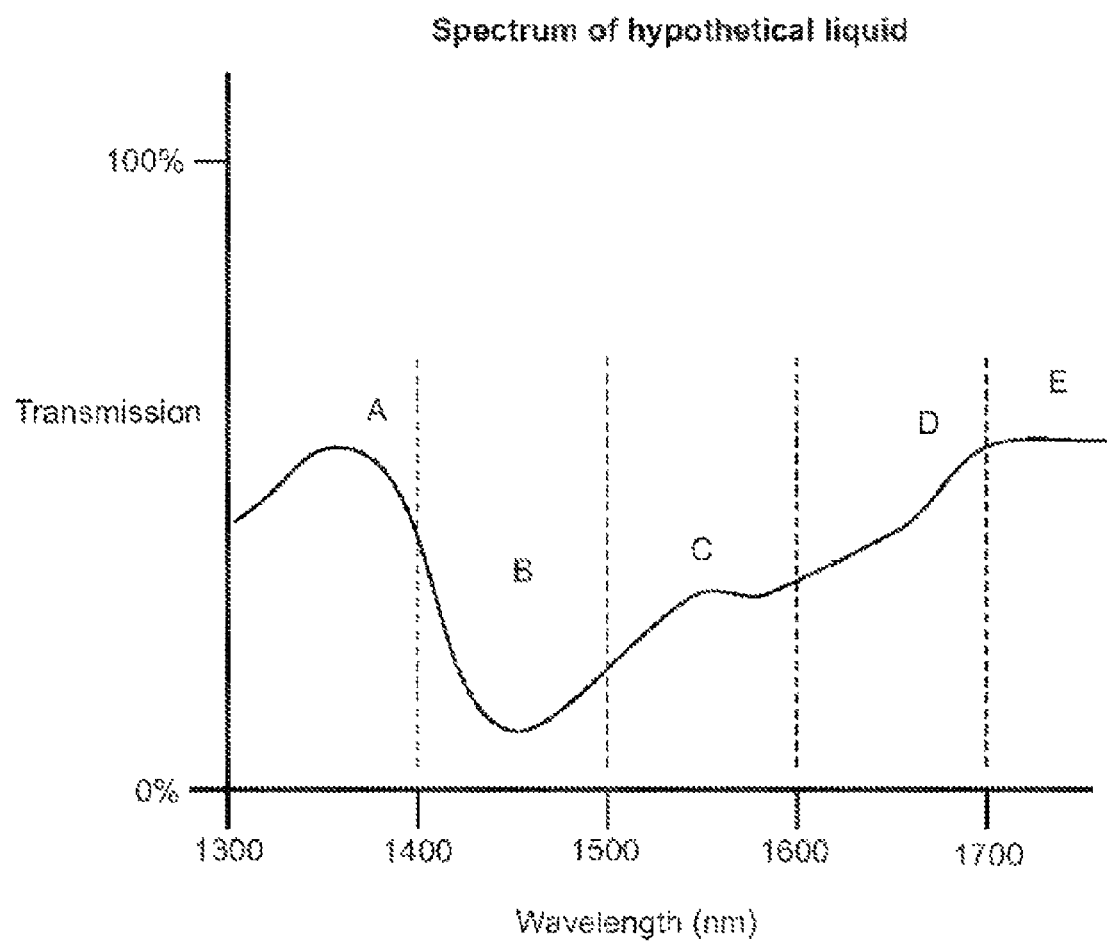
FIG. 2 shows in schematic form the hypothetical spectrum of a hypothetical liquid base/carrier.

Selection of each wavelength can be demonstrated with reference to the spectrum of a hypothetical base liquid as shown in FIG. 2. The hypothetical spectrum comprises the following spectral characteristics A-E in the analysis range.

A peak between 1300 nm and 1400 nm (centre wavelength of 1350 nm of actual peak) (A).

A trough between 1400 nm and 1500 nm (centre wavelength of 1450 nm of actual trough) (B).

An inflection between 1500 nm and 1600 nm (centre wavelength of 1550 of actual inflection) (C).

A slope between 1600 nm and 1800 nm (D).

A plateau between 1800 nm and 2000 nm (E).

A knee is also shown around 1800 nm between characteristics D and E.

For analysis of drugs with this hypothetical liquid as a base, wavelengths could be chosen that are within the vicinity of the wavelength ranges (or centre wavelength) for one or more of the spectral features A-E above, or that fall within in a region spanning (defining/delimiting) the wavelength ranges for one or more of the spectral features A-E above. A wavelength in the "vicinity" of a spectral characteristic also can mean a wavelength at the spectral characteristic centre wavelength. For example, three different wavelengths could be chosen as follows.

Wavelength #1 1310 nm—within the region 1300-1400 nm for feature A.

Wavelength #2 1450 nm, roughly at or within the vicinity of the centre wavelength of feature B.

Wavelength #3 1800 nm, at the edge/knee (i.e. within the region) of feature E.

The chosen discrete wavelengths that relate to spectral characteristics of the liquid spectrum can be termed "selected wavelengths" or "chosen wavelengths". In general terms, the selected or chosen wavelengths "correspond" to or "capture" a spectral characteristic.

It will be appreciated that FIG. 2 shows just some hypothetical examples of spectral characteristics (features)—many more are possible for a spectrum. Further, the wavelength ranges for spectral characteristics could overlap or even coincide. Further, a separate wavelength need not be chosen for each spectral characteristic in the analysis range—just a selection of wavelengths relating to a selection of spectral characteristics might be chosen. It might not be possible to define a spectral characteristic by a wavelength range, or any such range might vary depending on interpretation. A wavelength in the vicinity of a spectral characteristic might instead be chosen. This could be a wavelength that is near or within a certain tolerance (e.g. +/−30 nm) of the centre point wavelength of a spectral characteristic, for example.

In addition, the selected wavelength might be influenced by sources 11 that are readily obtainable or configurable to a wavelength that is in the vicinity of or falls within in a region spanning such a spectral characteristic. The selection of suitable wavelengths for the emitted radiation will provide better information for accurate verification or identification by the processor.

In addition, preferably, the selected wavelengths can be selected independently from the drug(s) being tested.

It will be appreciated that the wavelengths could be selected in any other suitable manner, such as by randomly or evenly spacing them across the region, or using some other selection criteria.

Figure 3:
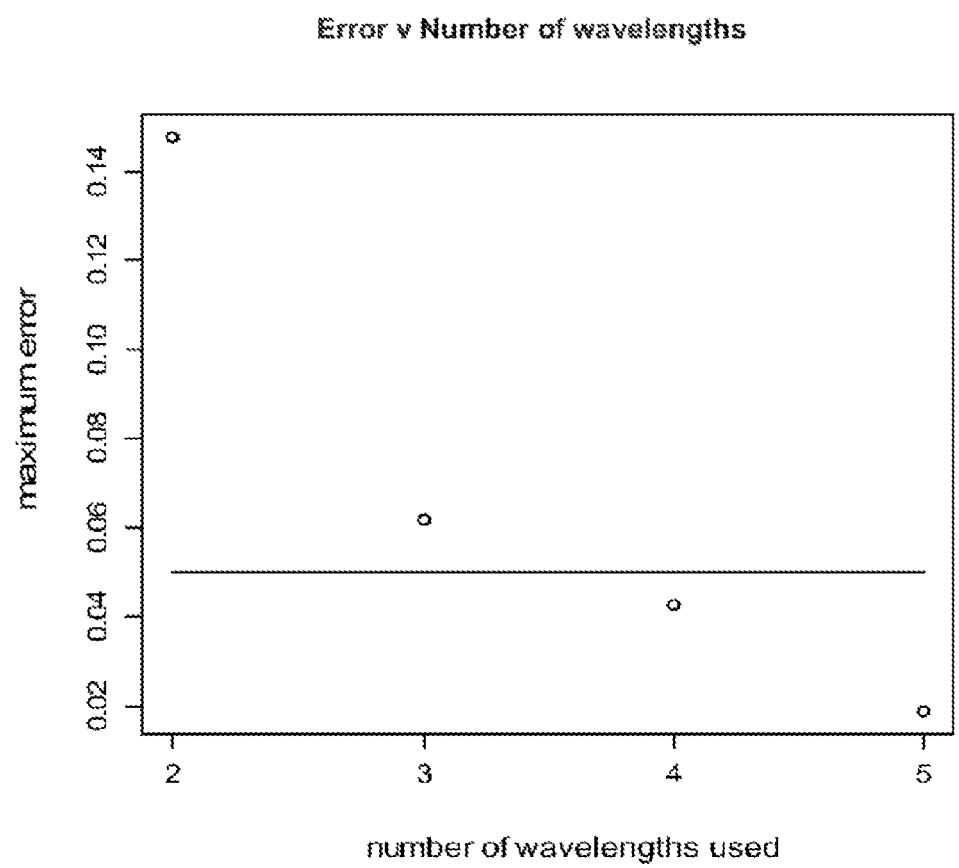
FIG. 3 is a graph showing the error vs. number of wavelengths used in the spectroscopic analyser.

Any suitable number of wavelengths can be used. Optionally, although not essentially, the number of different wavelengths constituting the electromagnetic radiation (either in one or multiple beams 22) provided by the source 11 is at least $\log_2 n$, where n is the number of samples that are tested for. The more wavelengths that are used, the better the accuracy, but this is optimised against costs and convenience. As seen in FIG. 3, as the number of electromagnetic radiation beams/wavelengths increases, the error of detection decreases. A selection of two wavelengths provides an error of 0.14 for a set of 30 drugs, whereas five wavelengths provide an error of just 0.02.

One of the electromagnetic radiation wavelengths 22 can optionally be selected to have a wavelength at an anchor point, which can be used to eliminate the need for a reference channel. The anchor point is chosen to have a wavelength in a stable or other suitable portion of the spectrum of the underlying base liquid. The anchor wavelength is described further later.

Upon receiving output from a sample detector 17 and optionally a reference detector 20 (or alternatively output from a monitor diode that measures power of output electromagnetic radiation), the processor 18 executes an algorithm that accesses a database 23 comprising training/comparison data (possibly in the form of a look up table), and uses that output to verify or identify ("characterise") the sample 16 based on the affected electromagnetic radiation 14b detected from the sample 16, and optionally:

a) where a reference channel is used, the output of the detected affected radiation 15b from that reference sample, or b) where a source monitor diode is used, measured power of the output source electromagnetic radiation, using the training/comparison data. The training/comparison data can be obtained in a previous analysis of training samples using the analyser. In one option, the raw training/comparison data obtained from the detector(s) is processed to obtain training/comparison coefficients that can be used for characterisation of an actual unknown sample in a blind test.

The processor 18 can operate with or independently from the controller 12. Processing will be described further later.

In addition to or as part of the verification/identification process one or more of the following can be undertaken.

Measurement of the sample (including where appropriate the retainer) temperature and correction of the training/comparison data based on the sample temperature.

Determining parameters (coefficients) representative of the sample or training data/sample that are independent of sample concentration that can be referenced against parameters representative of the comparison data/comparison sample for identification/verification.

Determining concentration of the sample.

Processing raw training/comparison data and actual sample data to reduce inaccuracies caused by dimension tolerances in the system including the sample retainer (e.g. a test-tube/test-tube holder, other type of test cell, part of an infusion pump/IV set, flow-cell, syringe or any other type of device for holding any of these or holding a sample/substance in any manner.)

Determine and/or eliminate the dark current of the photodetectors using either a technique involving a modulated source or dark current measured using a chopper wheel arrangement.

A user interface 24 allows a user to operate the apparatus 10, including setting parameters, inputting anticipated drugs (e.g. for verification) or other sample identification and receiving the results of analysis (via a screen, display, audio alarm, indicator or similar). The results might indicate whether the drug is as anticipated (verification/confirmation), or might advise of the drug (identification) and/or might indicate concentration of the sample under blind test.

The controller 12 and/or processor 18 might also control an external device (such as an infusion pump) to allow or prevent delivery of a drug based on the test result.

Preferably, the apparatus 10 also comprises a feedback system to stabilise the temperature of the electromagnetic radiation source 11 and/or the detectors(s) 17, 20. In one example, thermistors detect the temperature of the electromagnetic radiation source and/or detector(s) and/or also optionally the sample retainer 2a, 2b, 2c, 5a, 5b. Peltier cooling devices can be operated to cool and stabilise the temperate of the source 11 and detectors 17, 20. The output of the thermistor(s) is sent to the controller 12, which controls the peltier cooling devices to cool the source and/or detectors. Preferably the thermistor is the built-in photodetector/source thermistor 2a, 2b, 2c, 5a, 5b, and the peltier thermo-electric cooler is built-in to the photodetector/source 2a, 2b, 2c, 5a, 5b.

The apparatus 10 works generally as follows, with reference to the flow diagram in FIG. 4. The controller 12 is used to operate the source 11 to emit one or more electromagnetic radiation beams 22 (preferably—although not essentially—individually and in sequence) with/at the selected wavelengths towards the sample 16, step 40. The electromagnetic radiation incident 14a on a sample 16 is transmitted or reflected through the sample and becomes affected electromagnetic radiation 14b which is detected by the detector 17, step 41. Optionally, the emitted radiation maybe diverted by a beam splitter 21 also to a reference sample 19 (of free-space path), which is detected by the same or a different detector 20, step 42. The outputs 14c, 15c from the sample detector 17 and optionally the reference detector 20 are passed to the processor 18, step 42. Here pre-processing takes place to normalise and/or correct the detector output 14c, 15c, step 42 if required. Then the identification/verification algorithm is executed, step 43, which includes querying the database 23 of reference drugs, the information from which (e.g. training/comparison data) being utilised to identify or verify the sample from the normalised detector output. The result of the verification or identification of the sample is communicated by the user interface 24, step 44.

Other options will become apparent as a more detailed description of the invention is provided.

First Embodiment

One embodiment of the invention will now be described in detail by way of example. This should not be considered limiting but illustrative. The embodiment is described in relation to an apparatus for providing verification or identification of water or other liquid based drugs from e.g. a set of 15 drugs set out in the table below. While in this embodiment the sample is referred to as a drug, more generally the embodiment could be applied to any other sample type.

Figure 5:
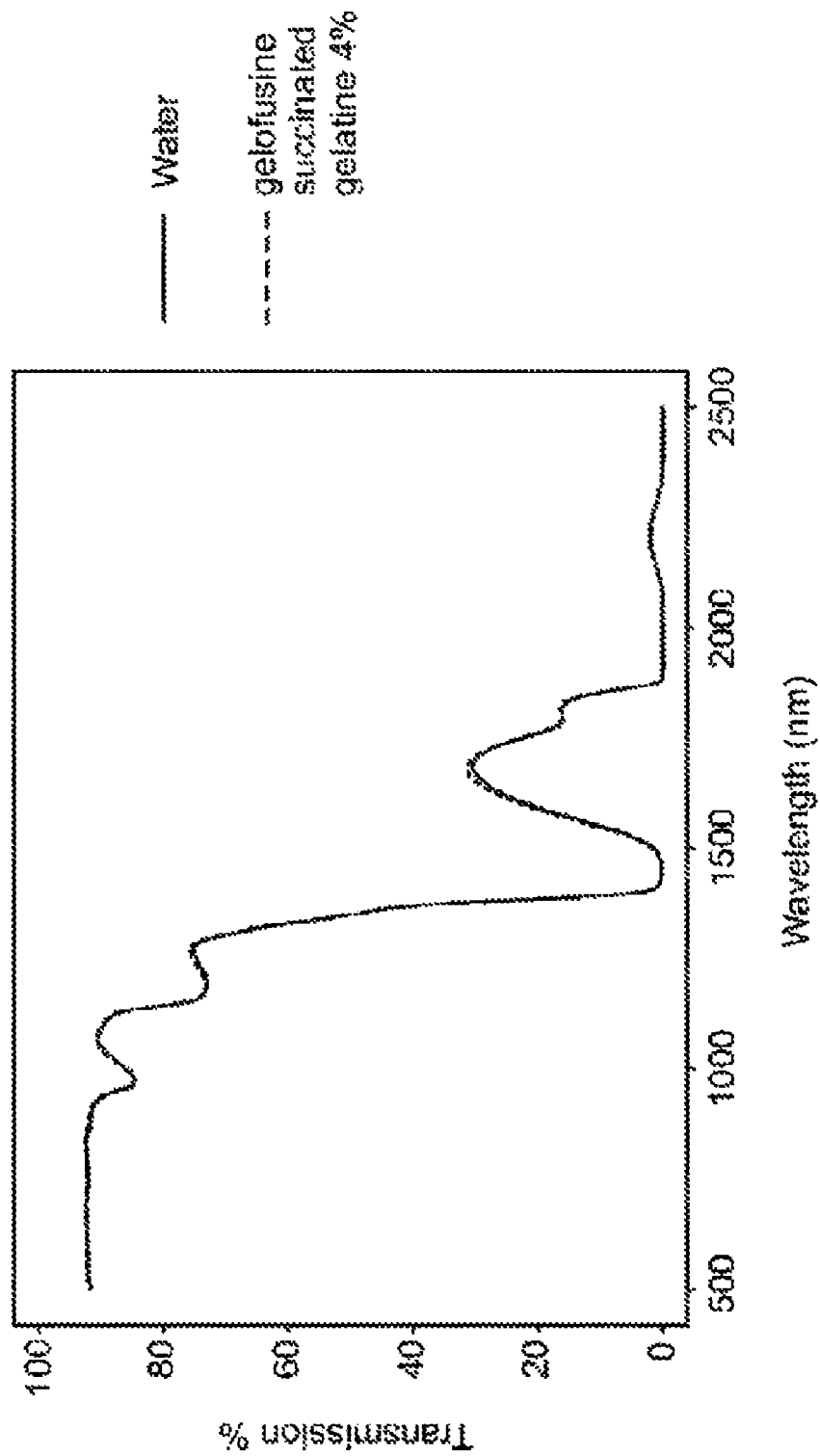
FIG. 5 shows the spectrum of a drug (gelofusine succinated gelatine solution 4%) overlaid the spectrum of a liquid based, being water.

Six wavelengths of electromagnetic radiation are chosen for this example, six being greater than $\log_2 n$ of 30. The wavelengths are chosen in the analysis range and are based on the spectral characteristics of water, being the base liquid, falling in that range. The spectrum of a water based drug (or other liquid based drug or aqueous solution) will be heavily dominated by the base liquid spectrum. For example referring to FIG. 5, the spectrum (dotted line) of drug W (gelofusine succinated gelatine solution 4%) is very similar to the spectrum of water (solid line). This is because the spectrum of water dominates. However, the differences in transmission coefficient between different water based drugs can be measured. Focussing on areas/wavelengths of spectral characteristics of the water spectrum, by using electromagnetic radiation beams at those wavelengths, the difference between the water spectrum and the water based drug spectrum at those wavelengths can be utilised to provide drug discrimination for drug identification or verification.

Figure 6:
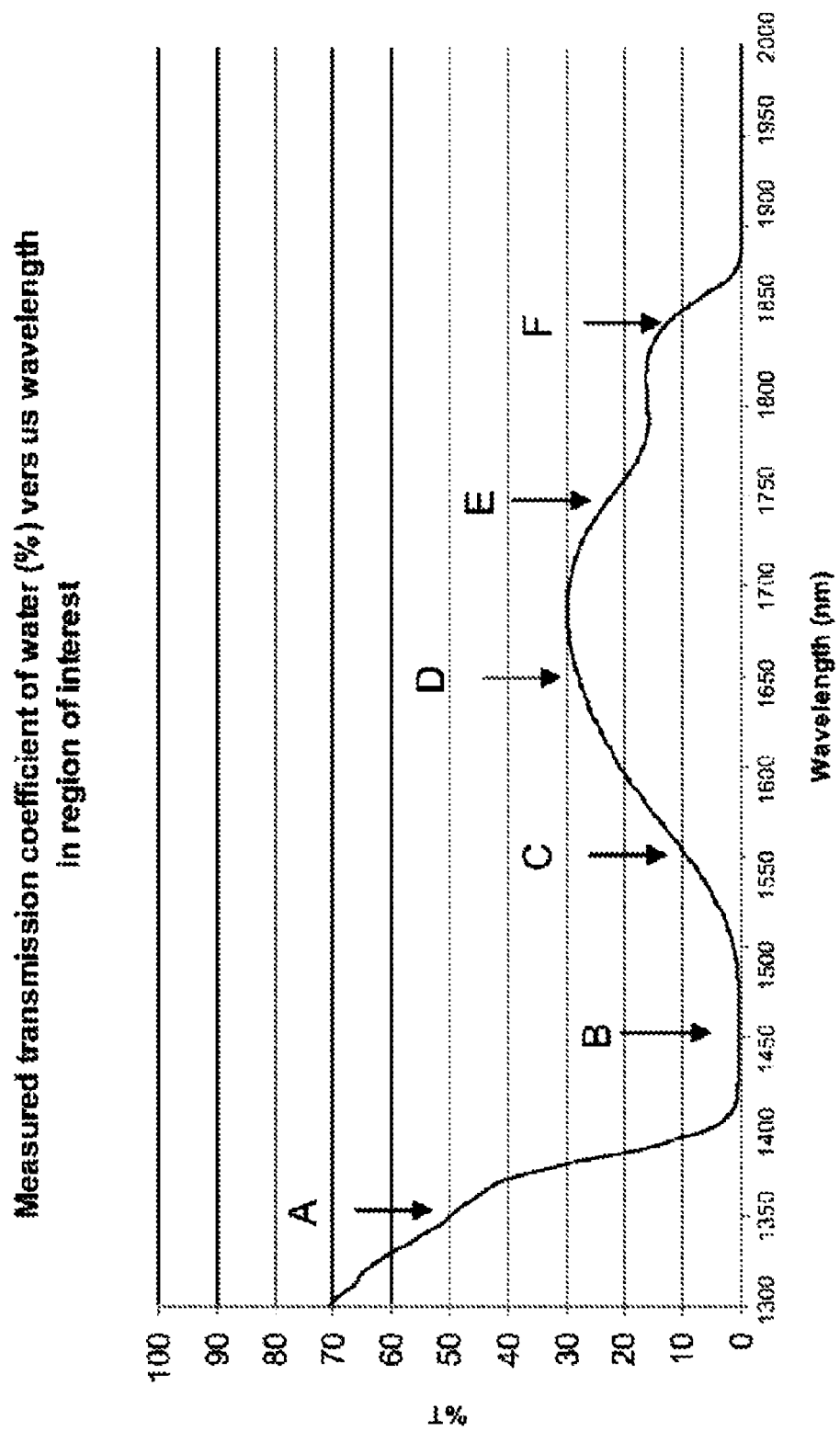
FIG. 6 shows spectral characteristics of water between 1300 and 2000 nm.

FIG. 6 shows a spectrum of water with some possible spectral characteristics (features) in the analysis range identified, and explained further below.

Spectral characteristic A (slope)—in a first region between 1300 nm and 1400 nm.
Spectral characteristic B (plateau/trough)—in a second region between 1400 nm and 1500 nm.
Spectral characteristic C (slope)—in a third region between 1500 nm and 1600 nm.
Spectral characteristic D (peak)—in a fourth region between 1600 nm and 1700 nm.
Spectral characteristic E (inflection)—in a fifth region between 1700 nm and 1800 nm.
Spectral characteristic F (knee) a sixth region between 1800 nm and 2000 nm.

This is not an exhaustive list of possible spectral features.

The selection of a wavelength for an electromagnetic radiation beam is not strictly fixed, and not necessarily solely based on spectral characteristics of the base liquid. It is influenced by the wavelength of spectral characteristics in spectrum of the base water of the drug sample, but in addition the selected wavelength can be based on other factors also. For example, in interest of cost effectiveness and a regularly obtainable supply chain, it might be preferable to use or select an alternative wavelength that is close to the spectral characteristic but not quite the same, if that alternative wavelength is easily obtainable by an off-the-shelf laser or other optical component.

For example, it is possible to use 1310 and 1550 nm as selected wavelengths for water based drugs as there are many devices configured for these wavelengths as they have wide spread use within the communications industry. Laser diodes nominally have centred wavelengths at 1650 nanometers, 1750 nanometers and 1850 nanometers, although these can be varied by up to plus or minus 30 nanometers. So wavelengths in these ranges can also be selected. Therefore by looking at the availability of these components, and the spectral characteristics of the base liquid, suitable wavelengths for the emitted radiation can be determined.

Therefore, based on the above explanation, each of the six wavelengths can be chosen to be within the vicinity or within the region spanning one of each of the spectral features, but also influenced by the availability of hardware. The six wavelengths for water could therefore be (by way of example): 1350 nanometers corresponding to feature A, 1450 nanometers corresponding to feature B, 1550 nanometers corresponding to feature C, 1650 nanometers corresponding to feature D, 1750 nanometers corresponding to feature E and 1850 nanometers corresponding to feature F, all which fall within the 1300-2000 nanometers. As can be seen the 1350 nm to 1850 nm wavelength selections do not match exactly to peaks and troughs and other spectral characteristics in the water spectrum, although are close. The selections also relate to operating wavelengths of available hardware. These are of course nominal wavelengths and the actual wavelength might vary in practice due to source 11 characteristics. It should also be noted that arbitrary wavelengths could be chosen spread across the region, rather than selected at specific spectral features.

Figure 22:
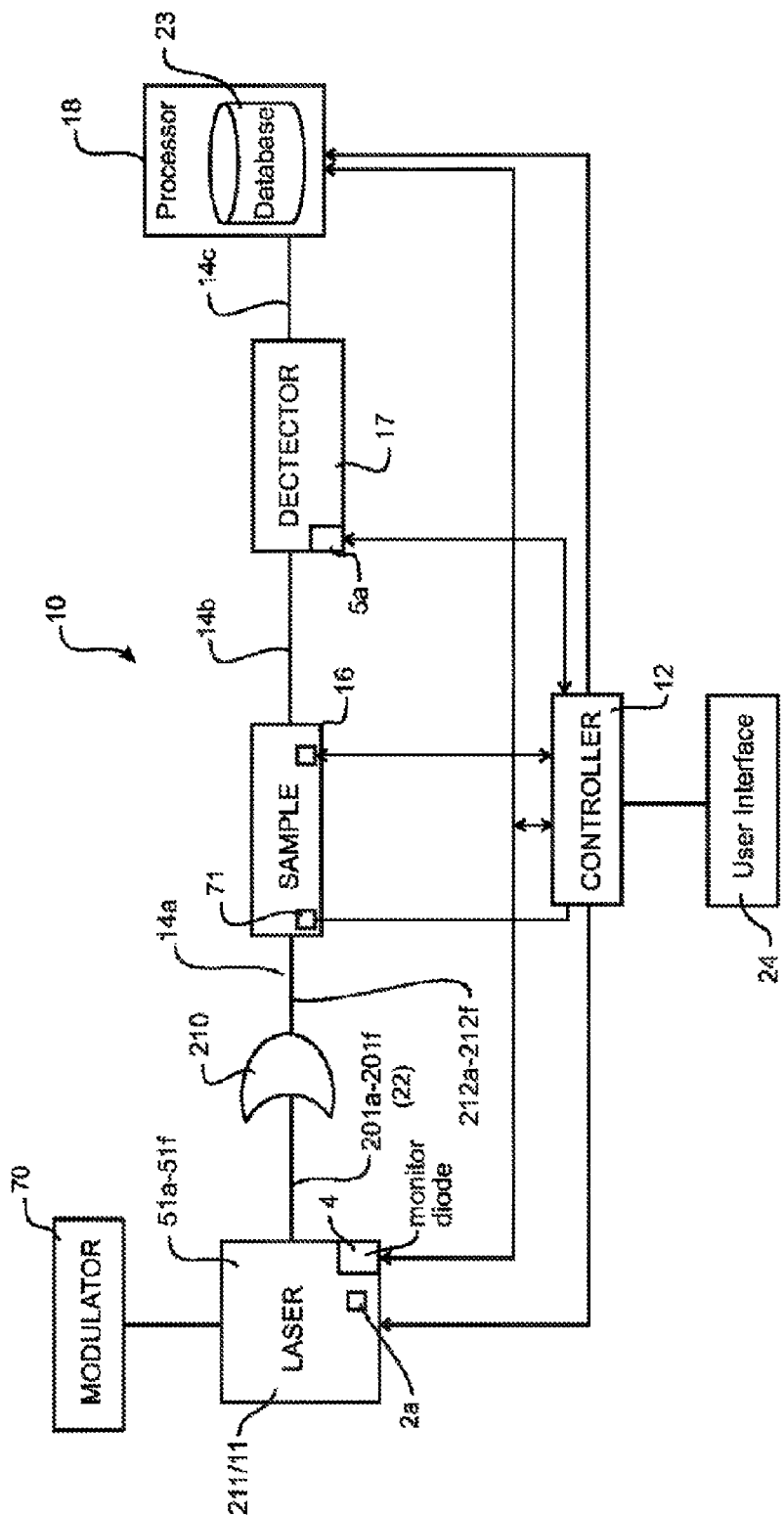
FIG. 22 shows a schematic diagram of a first embodiment of the spectroscopic analyser in which the sources are lasers in a single package.

FIG. 22 shows in schematic form one possible form of the apparatus 10 as generally described in FIG. 1. The spectroscopic analyser 10 has a controller 12 and a single laser package (more generally "laser") that contains six laser modules 51a-51f, which together form the source 11 to output electromagnetic radiation 22 at a plurality of wavelengths in the form of light. The single package 211 comprises 6 lasers forming the source 11 that are arranged to emit their electromagnetic radiation beam 22 (which could be any one of wavelengths 201a-201f) towards an integrated collimating lens 210. The package is operable to emit a tuned or tuneable wavelength at each of six wavelengths 201a-201f towards the lens 210. The package comprises one or more laser diodes providing a stable, high intensity, narrow band collimated electromagnetic radiation output that is controlled electronically via controller 12. The controller can have a user interface 24 for user input and output. The source can have an inbuilt or separate temperature sensor 2a, such as a thermistor for detecting the operating temperature. The output can be passed to the processor 18.

The controller 12 activates the laser package to sequentially or otherwise to emit a beam 201a-201f of a single wavelength towards the sample. Alternatively, multiple beams 201a-201f could be operated at once such that an electromagnetic beam 22 comprising multiple wavelength components (e.g. 201a-201f or a subset thereof) could be emitted towards 14a the sample 16 via the lens 210.

The apparatus comprises a modulator 70, which can be a separate device coupled to the laser package 211 or incorporated into the controller 12, or it can be incorporated into the laser package itself. The modulator 70 controls the laser package 211 to modulate the output electromagnetic radiation 22. Modulating the electromagnetic radiation allows for processing to account for dark current as will be described below.

The package 211 comprises one or more monitor photodiodes 4a for detecting output electromagnetic radiation 22 (e.g. for measuring output power of the electromagnetic radiation) for feedback control of that radiation. This can be combined with the temperature sensor 2a. The output is provided to the processor 18 either directly or via the controller 12. Lasers have fewer heat emission problems than other sources, thus reducing the detrimental effects of heat on the measurements. The output power of each laser preferably is nominally the same (typically 2-3 mW although could be more) in the interests of having a balanced apparatus. Preferably, this also enables a common diode driver circuit to be used for the laser diodes.

There is also a temperature sensor 71 (e.g. non-contact infrared sensor) for measuring the sample 16 under test and its retainer. There may be a combined or separate temperature sensor for measuring the retainer temperature as well. The outputs are provided to the processor 18, either directly or via the controller 12.

Once activated, the laser 211 emits (preferably modulated) electromagnetic radiation 22 towards the sample along the path 14a via the lens 210. The path 14a from the source to the detector is a combination of free-space with optical fibre components. This reduces optical attenuation and hardware. The apparatus also comprises a sample retainer 16a, which is aligned with the beam path 14a. The emitted electromagnetic radiation from an active laser 51a-51f is incident on and transmits or reflects through the sample 16 in the sample retainer.

The detector 17 is placed in the affected radiation path 14b that exits the sample 16. Preferably the detector 17 is a single photodetector (such as a photodiode) biased to have a suitable response to detect electromagnetic radiation of wavelengths that will be in the affected radiation. A single detector reduces the errors due to variability introduced by components—it removes the relative differences between multiple photodetectors enabling a more stable response to the output of the emitted electromagnetic radiation thus enhancing sensitivity. An InGaAs photodiode could be used, for example. The detector 17 detects the affected radiation 14b and the output 14c of the detector 17 is passed to a processor 18 that using previously obtained training/comparison data in a database 23 verifies or identifies or otherwise characterises the sample as described herein. In addition to or as part of that process the processor 18 also undertakes the following.

Measurement of the sample (including where appropriate the retainer) temperature and correction of the training/comparison data based on the sample temperature.

Determining parameters (coefficients) representative of the sample or training data/sample that are independent of sample concentration that can be referenced against parameters representative of the comparison data/comparison sample for identification/verification.

Determining concentration of the sample.

Processing raw training/comparison data and actual sample data to reduce inaccuracies caused by dimension tolerances in the system including the sample retainer (e.g. a test-tube/test-tube holder, other type of test cell, part of an infusion pump/IV set, flow-cell, syringe or any other type of device for holding any of these or holding a sample/substance in any manner.)

Determine and/or eliminate the dark current of the photodetectors using either a technique involving a modulated source or dark current measured using a chopper wheel arrangement.

Preferably, the apparatus also comprises a feedback system to stabilise the temperature of the electromagnetic radiation source 11 and the detectors(s). In one example, thermistors 2a, 71, 5a detect the temperature of the electromagnetic radiation source and/or detector(s) and/or retainer. Peltier cooling devices can be operated to cool and stabilise the temperate of the source and detectors. The output of the thermistor(s) is sent to the controller, which controls the Peltier cooling devices to cool the source and/or detectors. Preferably the thermistor is the built-in photodetector/source thermistor 2a, 71, 5a, and the peltier thermo-electric cooler is built-in to the photodetector 2a, 5a.

The apparatus/analyser 10 is used to obtain raw training/comparison data from training samples carried out during a training process/test. It also obtains raw data of an actual unknown sample under test during a blind test. It can process the raw training/comparison data and/or the raw data of the sample under test to obtain coefficients (comparison data) that can be utilised in a process to characterise the unknown sample in the blind test.

Figure 23:
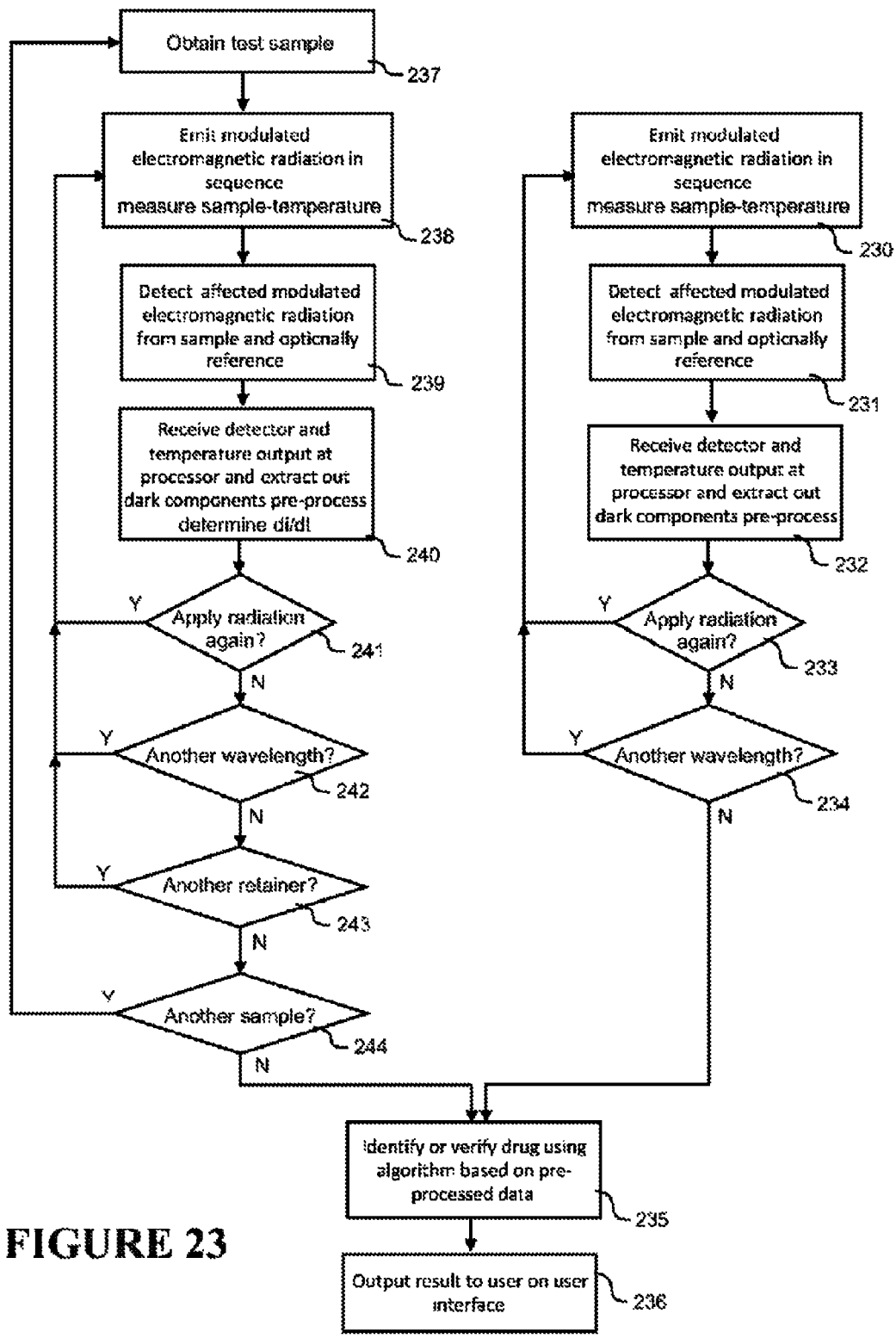
FIG. 23 is a flow diagram showing operation of the spectroscopic analyser according to the first embodiment.

Referring to FIG. 23 (which is based on but provides more detail than Figure), operation of the apparatus 10 will now be described for a blind test. A blind test is where an actual unknown sample for verification or identification or other characterisation is tested. An unknown sample 16 to be tested is placed in the retainer or otherwise placed in or introduced to the analyser 10. The controller 12 operates the laser 211 to emit an electromagnetic radiation beam 22 at one of the selected wavelengths 201a-201f to the sample 16, step 230 As part of this, preferably the modulator 70/controller 12 operates the laser 211 to modulate the electromagnetic source radiation beam 20, step 230, in a manner to be described below with respect to the processor 18. In this manner, six modulated electromagnetic source radiation beams 201a-201f with different selected wavelengths can be emitted, step 230, in sequence from the laser 211, each tuned to a different selected wavelength. The temperature of the sample is measured and recorded for each test at any suitable time in the process, e.g. at the same time as emitting the radiation, step 230.

Each electromagnetic beam 22 is emitted via the integrated collimating lens 210 along the path 14a towards the sample 16. The affected radiation coming from the sample is detected by the photodetector 17, step 231, for each electromagnetic radiation beam emitted 14a towards the sample 16.

Figure 18:
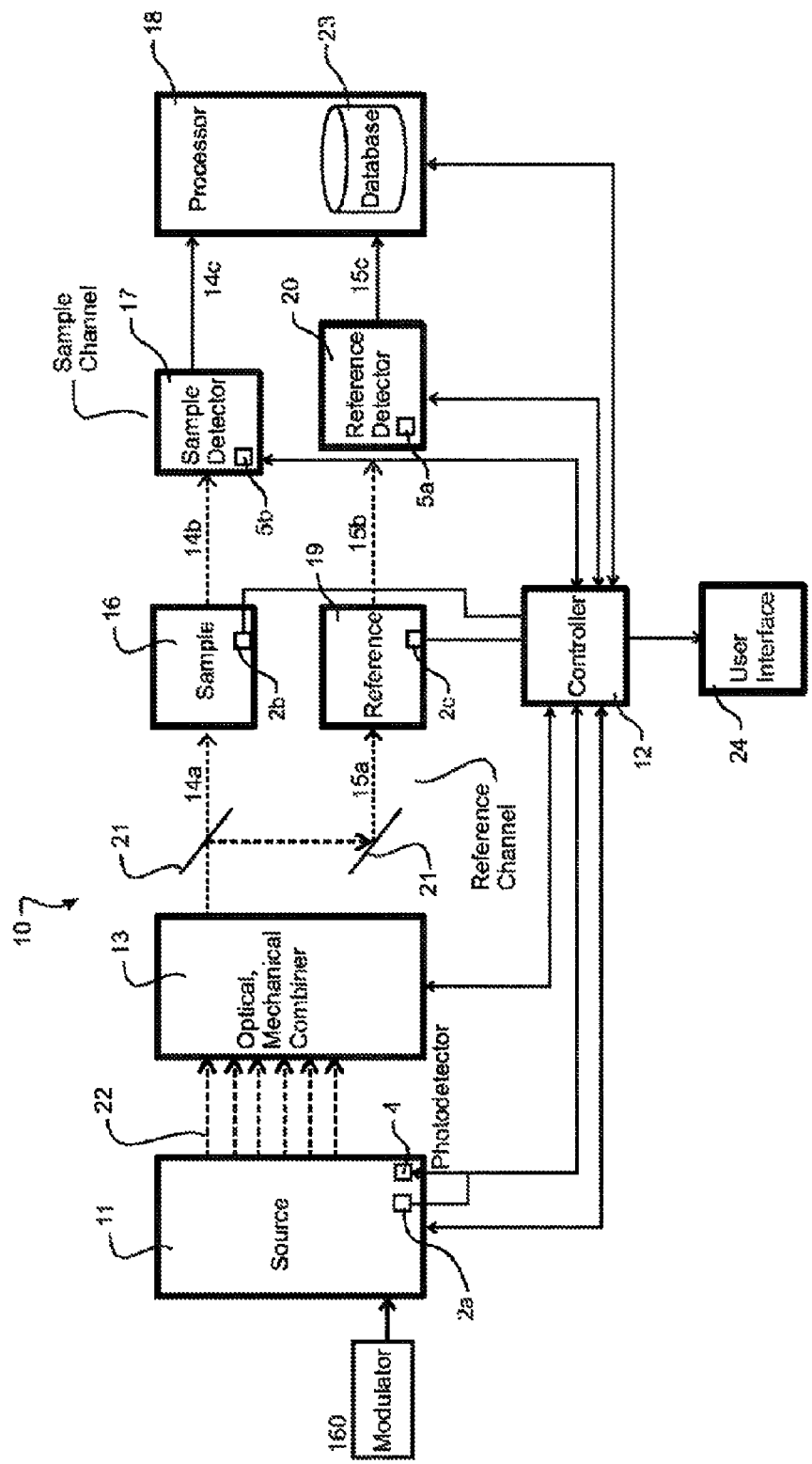
FIG. 18 shows a schematic diagram of an analyser with a modulator.
Figure 19:
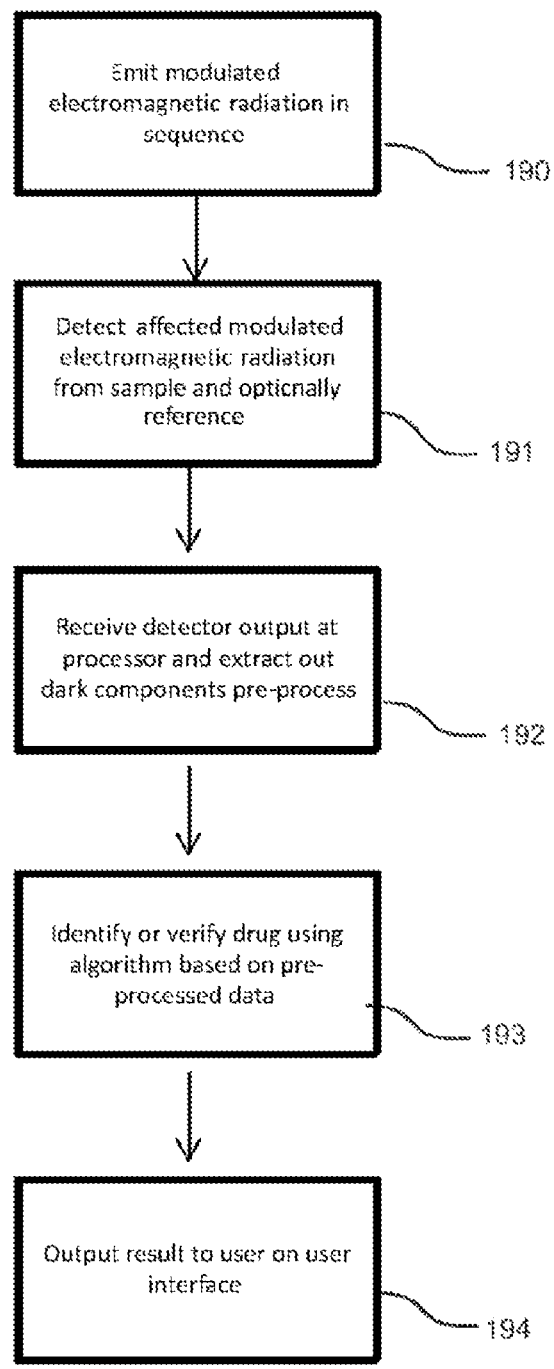
FIG. 19 shows a flow diagram for extracting dark current

Optionally, the monitor diode 4a in the laser 211 measures the power of the output electromagnetic radiation beam 22 to obtain reference information. Alternative, reference information can be obtained using a reference channel such as shown in FIG. 1 or FIG. 18.

The output (electromagnetic radiation intensity measurements) from the sample detector 17 and optionally the monitor diode 4 in the source laser 211 are passed to the processor 18 and/or database 23 where it is stored as data, step 232, for identification/verification of the sample 16 under test. The temperature measurement is also passed to the processor 18 and/or database 23. The output 14c received at the processor 18 from the sample detector 17 or from the monitor diode 4 indicates the intensity of the affected electromagnetic radiation 14b for each emitted electromagnetic radiation beam at the sample 16. It may, for example, comprise data which directly or indirectly indicates photocurrent of the detector (such as a voltage proportional to intensity) and/or intensity of the detected electromagnetic radiation. In this case of modulated source (as discussed below) a modulated waveform output is received which is digitised. The steps 230-232 are preferably repeated several times for each wavelength to obtain multiple intensity measurements that can be processed to obtain an average or other representative intensity for each wavelength, step 233. For example, at each wavelength, the analyser detects affected electromagnetic radiation affected by the sample at 25 different times and passes this output to the processor 18 and/or database 23, step 230-233. Once the process has been completed for one wavelength, the process, steps 230-233, is repeated for the remaining wavelengths, step 234. The temperature measurement can be taken during each iteration also and stored in the processor/database as appropriate, step 230. The intensity and temperature data in the processor/database can be termed "blind test raw data".

Once all the intensity, temperature and any other measurements have been received by the processor 18, verification or identification can take place, step 235. Identification or verification of a sample is based on training data (also termed "comparison data") that has previously been generated or otherwise obtained. In this embodiment, sample coefficients or other data representing the sample under blind test are obtained/determined from the blind test raw data during the identification/verification process and these are compared to corresponding training coefficients or other comparison data obtained from test samples during a training process. If the coefficients or other data of the sample under test match to the required similarity to those of a test sample, then a verification or identification can be made.

It will be appreciated that in general terms, the raw training data and/or blind test raw data can be used as is or processed in any suitable way to undertake characterisation of the unknown sample under test. The coefficients described in this embodiment demonstrate one way in which to use the raw data. "Training data" can refer to raw training data in its unprocessed form, or processed raw training data. Furthermore, "comparison data" can refer to processed or unprocessed raw training data and/or processed or unprocessed raw blind test data. Comparison data refers to any data that can be used to characterise an unknown sample under blind test.

Verification involves confirming that a sample drug is the drug that is expected. For example, a clinician can specify what they think the drug is (e.g. from the set of n drugs) through the user interface 24 step 85, then use the apparatus to confirm whether the drug in the retainer is actually that drug which is specified by the clinician. Identification involves determining what a drug actually is, without any suggestion from the clinician as to what the drug is. For verification/identification, the blind test raw data are processed and are compared against the processed raw training data in the database 23, step 85, to identify the drug, or verify whether it is the anticipated drug as specified by the clinician. Output is then provided to the user interface, step 87.

The verification/identification processing will now be described in more detail. However, as the verification/identification processing utilises training data, the acquisition and (optional) processing of training data will be described first with reference to FIG. 23.

Acquisition of Training Data

In overview, training data is obtained during a training process at some point prior to verification/identification of an actual unknown sample taking place in a blind test. It can be obtained once, or periodically updated. It is stored in the processor 18 and/or the database 23, either integrated with or accessible by the processor 18 for use during verification/identification. As mentioned above, the terms "training data" and "comparison data" in general can refer to raw data obtained during a training process, or raw data that has subsequently been post-processed for utilisation in the identification/verification process. The training data is obtained from known samples against which data from blind test samples will be analysed. Preferably, any unknown sample type (e.g. a particular drug) that may be tested for in a blind test will have corresponding training data previously obtained from the same sample type (e.g. drug). A set of training samples (e.g. a set of drugs) corresponding to those that may be tested for, are obtained, analysed in the training process and raw training data obtained for them and stored. The raw training data is obtained in the same way as actual the blind test data is obtain as described herein, e.g. as shown in FIG. 23 using e.g. the apparatus in FIG. 22 or any of the other embodiments described.

As an example, with reference to FIG. 23, a set of test (training) samples (e.g. different training drugs/dilutants such as those in the table below) are obtained, step 237. The samples comprise a range of undiluted drugs of known concentration and dilutants of interest (e.g. 0.9% saline, 5% glucose) being the dilutants in which a drug may be diluted in for an actual blind test. Each one is analysed in turn, using e.g. the analyser of FIG. 22. As described previously for the actual blind test, the training drug is placed in a retainer, and (optionally modulated) electromagnetic radiation of different wavelengths is emitted at the drug in the retainer in sequence, step 238. The intensity of the affected electromagnetic radiation from the drug at each wavelength is detected by a detector, step 239 and is passed to the processor 18, and/or database 23, step 240. Preferably, each wavelength of electromagnetic radiation can be emitted multiple times, step 241, and the detector intensity output/measurement from each is averaged or otherwise processed in the processor to obtain the raw training data. Once one wavelength is complete, the sample is tested at the next wavelength 242. Each drug can also be tested multiple times at each wavelength in a different retainer (e.g. different test tubes) to average out variations in each retainer, step 243. The temperature at each measurement at each wavelength for the lasers, detectors and sample/retainer can also be taken and passed to the processor/database for storing along with the intensity measurement, steps 238, 240. This is repeated for each sample drug, step 244. Note, while the FIG. 23 shows that each wavelength is tested multiple times, then the retainer is changed, alternative orders could occur—such as the retainer changed for each wavelength before changing the wavelength. Various orders are possible and the description and FIG. 8 should not be considered limiting.

If a reference channel is used, the same process is carried out for the reference channel—that is (optionally modulated) electromagnetic radiation of different wavelengths is emitted at detector without a sample or retainer in the path, step 238. The intensity of the received electromagnetic radiation at each wavelength is detected by a detector, step 239, and is passed to the processor 18, and/or database 23, step 240. Preferably, each wavelength of electromagnetic radiation can be emitted multiple times, step 241, and the detector intensity output/measurement from each is averaged or otherwise processed in the processor to obtain the raw training data. Once one wavelength is complete, the next wavelength is emitted, step 242. The temperature at each measurement at each wavelength for the lasers and detectors can also be taken and passed to the processor/database for storing along with the intensity measurement. This is repeated for each sample drug, step 244.

Alternatively, if a monitor diode 4 is used instead of a reference channel, the same process is undertaken. Optionally modulated electromagnetic radiation of different wavelengths is emitted at detector without a sample or retainer in the path, step 238. The intensity of the received electromagnetic radiation at each wavelength is detected by the monitor diode 4, step 239, and is passed to the processor 18, and/or database 23, step 240. Preferably, each wavelength of electromagnetic radiation can be emitted multiple times, step 241, and the monitor diode intensity output/measurement from each is averaged or otherwise processed in the processor to obtain the raw training data. Once one wavelength is complete, the next wavelength is emitted, step 242. Each drug can also be tested multiple times at each wavelength in a different retainer (e.g. different test tubes) to average out variations in each retainer, step 243—the monitor diode output is obtained for each one. The temperature at each measurement at each wavelength for the lasers and detectors can also be taken and passed to the processor/database for storing along with the intensity measurement. This is repeated for each sample drug, step 244.

The result is a store of raw training data of (spectral) intensities and temperatures for each measurement at each wavelength for each sample drug and for each monitor diode 4 or reference channel measurement. The data comprises spectral transmission intensities (in the form described previously) at the wavelengths of interest (e.g. 6 wavelengths) along with respective temperature readings for each training drug. Where a monitor diode is used, the data also comprises spectral transmission intensities at the wavelengths of interest (e.g. 6 wavelengths) for each training drug. Where a reference channel is used, the data also comprises spectral transmission intensities at the wavelengths of interest (e.g. 6 wavelengths) along with respective temperature readings for each reference channel measurement. The raw training data will consist of multiple scans at each wavelength (typically 25 scans are used although any suitable number can be) using different retainers (for example, 5 different test tube retainers). The (spectral) intensities can take the form of a voltage or similar output from the detector that is digitised for the processor. In the case of the modulated source (which will be described further below) the digitised intensity may take the form of a wave form, or the amplitudes of components of the wave form.

The training data is obtained at a measured temperature. For later temperature compensation, the slope of the intensity versus temperature for a sample at a particular wavelength is obtained, step 240. This happens by placing the sample under test (preferably in the same retainer) into a laboratory spectrometer known in the art. The intensity for each sample is measured at several temperatures for each wavelength, and a straight line slope di/dt of the intensity versus temperature determined and passed to the processor 18/database 23 for later use.

The raw training data is later processed during the verification/identification process to obtain comparison (also termed "training") coefficients (comparison data) that can be used to verify/identify unknown samples in an actual blind test. In a preferred embodiment, the raw training data has dark current eliminated and is temperature corrected to match the blind sample test temperature. The data is converted into a set of coefficients, each of which reduces sensitivity to variations in the retainer path length and that is concentration independent and compensates for variations in the retainer path length. In a preferred embodiment, this processing occurs at the time of carrying out the blind test or shortly thereafter, but this is not essential. The processing could alternatively be carried out in advance of the actual blind test or after the blind test. The processing of the raw training data is described in detail further below.

Acquisition of Blind Test Data and Verification/Identification

In overview, the blind test data for an unknown sample drug is acquired as described previously resulting in raw blind test data comprising intensities and sample temperatures ($T_b$) at various wavelengths as measured during the blind test of the actual drug, and also (where used) reference intensities and temperatures at various wavelengths from the monitor diode (or alternatively the reference channel). The blind test raw data is processed to generate blind test (sample) coefficient(s). Mathematical analysis can be carried out between training coefficients based on previously determined training/comparison data and blind test coefficients to identify/verify the unknown sample under test.

In summary, the following occurs to each value of the raw data (each being data representing the detected intensity for a particular wavelength for a particular sample), which initially represents a modulated output from the detector.

First, the DC component of the output (for the blind test data and the training data) is removed/eliminated (e.g. utilising a modulation technique) and the magnitude of the signal is obtained (see heading—eliminating dark current using modulation). This DC component elimination occurs on the raw training data, either at the time of collection, or during the verification/identification process. This results in:
a set of dark current eliminated data ($N_1$ to $N_n$) (for the unknown sample under test) comprising a data point for each wavelength of the blind test data;
a set of dark current eliminated data ($N_1$ to $N_n$) for each drug in the training set comprising a data point for each wavelength of the raw training data.

Second, the magnitude of the set of dark current eliminated data ($N_1$ to $N_n$) for each drug in the training set comprising a data point for each wavelength of the raw training data then undergoes temperature correction/adjustment (see heading—temperature correction). This results in a set of temperature corrected data ($I(T_b)_1$ to $I(T_b)_n$) for each drug in the training set that matches the temperature of the blind test sample.

Third, a fractional intensity ratio (fractional spectral intensity) is obtained for:
each dark current eliminated data point ($N_1$ to $N_n$) for the unknown sample under test;
each dark current eliminated data point ($N_1$ to $N_n$) for each drug in the training set
wherein the fractional intensity ratio is a parameter that reduces retainer tolerance sensitivity in verifying/identifying a substance (see heading—retainer tolerance sensitivity reduction.

This results in:
a set of fractional spectral intensity data ($g_{m1}$ to $g_{mn}$) (for the unknown sample under test) comprising a data point for each wavelength of the blind test data;
a set of fractional spectral intensity data ($g_{m1}$ to $g_{mn}$) for each drug in the training set comprising a data point for each wavelength of the raw training data.

Fourth, a coefficient is derived from using the fractional intensity ratio that is independent of sample concentration (see heading—concentration independent coefficients).

This results in:
a set of concentration independent data ($y_{m1}$ to $y_{mn}$) (for the unknown sample under test) comprising a data point for each wavelength of the blind test data;
a set of concentration independent data ($y_{m1}$ to $y_{mn}$) for each drug in the training set comprising a data point for each wavelength of the raw training data.

The set of data ($y_{m1}$ to $y_{mn}$) for the unknown sample under test can then be compared to set of data ($y^B_{m1}$ to $y^B_{mn}$) for each drug in the training set to verify or identify the unknown sample under test.

The verification/identification processing will now be described in more detail, with reference to FIG. 24 that shows step 235 of FIG. 23 in more detail.

Eliminating Dark Current Using Modulation

First, the dark current of the photodetectors 17/4 is compensated for, step 235a. This is done for the reference and sample data for both the raw training data and the blind test data. Photodectors have a baseline output (termed "dark current") even when there is no incident radiation. In this embodiment, rather than using a traditional chopper wheel arrangement to find dark current, laser driver current modulation is used to eliminate the need for dark current readings. Referring to the analyser in FIG. 22, the laser is output is modulated as previously described, step 230, FIG. 23. The affected detected radiation is received by the sample and reference detectors 17 (for both the training process and the blind test) and passed to the processor 18, steps 231, 232 for processing as previously described. The received output at the processor contains DC components corresponding to dark current as demonstrated in the derivation below. This output can be processed by the processor step 235a to remove the dark current (DC) component $A_{OS}$ and $A_{OR}$ of the received output (as per the equations below) and any other unwanted components. The desired components $\sin(\omega t)$ and $\cos(\omega t)$ are obtained and represent the intensity measurement without dark current. This processing can be done using any suitable signal processing know to those in the art.

For example, in one possibility, Fourier analysis of the output currents could be performed by multiplying the outputs by $\sin(\omega t)$ and $\cos(\omega t)$ respectively, and integrating over a period of the oscillation. This can be used where the modulation is a single frequency, e.g. sine wave modulation at a single frequency. This procedure provides a form of averaging which is beneficial in reducing measurement noise.

Alternatively, a Fast Fourier Transform (FFT) algorithm can be applied to a digitised output waveform and the relevant Fourier components extracted. From the Fourier coefficients we therefore obtain:
$S.\Delta P = \sqrt{A_{1S}^2 + B_{1S}^2}$ for the sample channel and $R.\Delta = \sqrt{A_{1R}^2 + B_{1R}^2}$ for the reference channel.

Taking the ratio of these Fourier amplitudes eliminates the dependence on the modulation depth $\Delta P$ to give a normalised (intensity) output, N, given by:

$$N = \frac{S}{R}$$

Where:
S is a constant representing the attenuation in the optical path including the sample cell.
R is a constant representing the fraction of incident power delivered to the reference.

A value of N (compensated intensity component) is determined at each wavelength of interest for the liquid/drug under analysis (be it a training sample or unknown sample under blind test) The set of values for each wavelength for a drug form a set of dark current eliminated data ($N_1$ to $N_n$). For example, where 8 wavelengths are used for testing, the set will comprise 8 N values—one for each wavelength The procedure results in dark current eliminated training data (comprising intensity components with the dark current removed) for the samples/drugs in the training process/set and dark current compensated blind test data (comprising intensity components with the dark current removed) for the sample under blind test. The intensity components with the dark current eliminated ($N_1$ to $N_n$) for each drug (in the training set and under actual blind test) are stored in the processor 18 and/or database 23.

Derivation of Dark Current Elimination Using Modulation

The modulated affected radiation leaving the sample 16 is detected by the photodetector 17, which provides a resulting output current. The output current is the sum of two components—a dark current term that is present even in the absence of any illumination, and a term proportional to the intensity of light incident on the detector. Therefore, we can write the sample channel output current, $I_S$ as follows:

$$I_S = I_S^{Dark} + S.P \quad (1)$$

where in (1):
$I_S^{Dark}$ is the dark current signal of the sample channel detector
S is a constant representing the attenuation in the optical path including the sample cell.
P is the incident power illuminating the sample cell.

A similar expression can be written for the reference channel output current, $I_R$, generated from the built-in photo-detector of the laser diode source, namely:

$$I_R = I_R^{Dark} + R.P \quad (2)$$

where in (2):
$I_R^{Dark}$ is the dark current signal of the reference photo-detector in the laser diode package.
R is a constant representing the fraction of incident power delivered to the reference.

Figure 17:
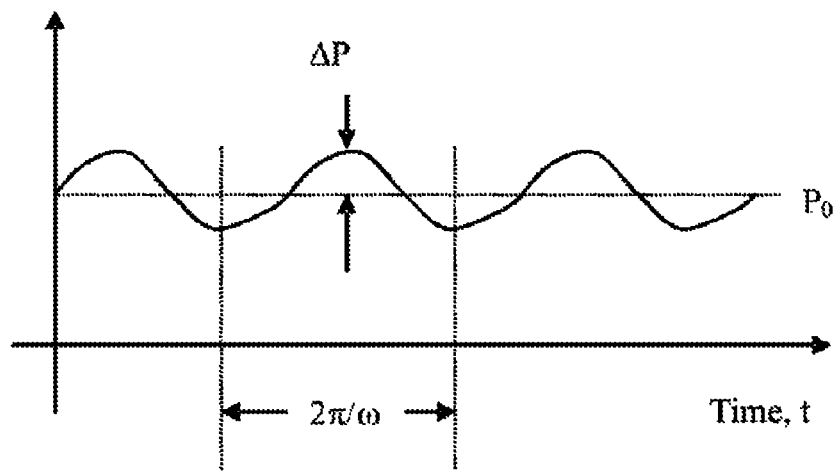
FIG. 17 shows laser output power where the source is modulated.

The laser 211 output is modulated by modulating the driver current with a known waveform. Typically, a sinusoidal modulation with angular frequency $\omega$ is used to vary the current about a mean value. This has the effect of modulating the output power of the laser diode source in a similar sinusoidal manner illustrated in FIG. 17:

Mathematically, the time-dependent laser output power, P(t), can be written as follows:

$$P(t) = P_0 + \Delta P.\sin(\omega t + \varphi) \quad (3)$$

where in (3):
$P_0$ is the mean output power from the laser
$\Delta P$ is the modulation amplitude in the output power waveform (depth of modulation)
$\varphi$ is the phase of the modulation waveform at tine, t=0.

Substituting for the incident power in equations (1) and (2) using (3), the following expressions for the output currents from sample and reference channels are obtained:

$$I_S = I_S^{Dark} + S.P_0 + S.\Delta P.\sin(\omega t + \varphi)$$

$$I_R = I_R^{Dark} + R.P_0 + R.\Delta P.\sin(\omega t + \varphi)$$

The parameters of interest with respect to characterising the sample under test are the constants S and R. The ratio of these two constants represents a normalised coefficient characteristic of the liquid in the sample cell.

Expanding the sinusoidal term in the above equations, gives:

$$\sin(\omega t+\varphi)=\sin(\omega t)\cos\varphi+\cos(\omega t)\sin\varphi$$

which gives the following:

$$I_S = I_S^{Dark} + S \cdot P_0 + S \cdot \Delta P \cdot \sin(\omega t)\cos\phi + S \cdot \Delta P \cdot \cos(\omega t)\sin\phi \quad (4)$$
$$\equiv A_{0S} + A_{1S}\cos(\omega t) + B_{1S}\sin(\omega t)$$

$$I_R = I_R^{Dark} + R \cdot P_0 + R \cdot \Delta P \cdot \sin(\omega t)\cos\phi + R \cdot \Delta P \cdot \cos(\omega t)\sin\phi \quad (5)$$
$$\equiv A_{0R} + A_{1R}\cos(\omega t) + B_{1R}\sin(\omega t)$$

So that:

$$A_{0S}=I_S^{Dark}+S.P_0$$

$$A_{0R}=I_R^{Dark}+R.P_0$$

$$A_{1S}=S.\Delta P.\sin\varphi$$

$$B_{1S}=S.\Delta P.\cos\varphi$$

$$A_{1R}=R.\Delta P.\sin\varphi$$

$$B_{1R}=R\Delta P.\cos\varphi$$

Inspection of equations (4) and (5) shows the output currents have the form of a simple Fourier series consisting of constant DC terms, $A_{0S}$ and $A_{0R}$, plus sine and cosine terms that oscillate with the modulation frequency, $\omega$, with amplitudes $A_{1S}$, $A_{1R}$, $B_{1S}$ and $B_{1R}$.

The dark current terms contribute only to the DC term of the Fourier series in (4) and (5). The dark current terms are contained within the DC components of equations (4) and (5). Therefore, a simple Fourier analysis of the modulated output waveform gives the Fourier coefficients of the $\sin(\omega t)$ and $\cos(\omega t)$ terms—which are independent of the dark current.

By measuring the sinusoidally varying component of each output current, the constants, S and R, can be determined without the need to measure the dark current of each detector diode. These latter terms can be eliminated from the measurement by DC blocking components or by performing a Fourier analysis of the output currents and discarding all but the sinusoidal terms.

In conventional spectrometer systems, the dark current would be measured by blocking off the illumination to the detector diode using a rotating mechanical chopper that periodically blocks then re-instates the optical illumination. Using the laser-current modulation described above eliminates the need for mechanical components such as rotating choppers which simplifies the spectrometer design, reduces cost and improves reliability by not using any moving parts. Electrical interference from the electric motors used to drive mechanical choppers is also eliminated.

Temperature Correction

Figure 24:
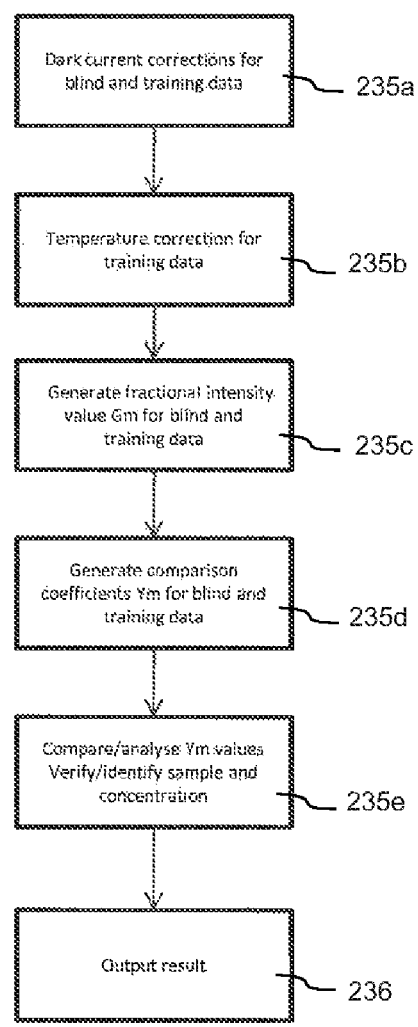
FIGS. 24 and 25 are flow diagrams showing the verification/identification process in more detail.

In overview, next temperature correction processing can be done to compensate for changes in intensity measurements from the detector due to temperature fluctuations of the retainer/sample step 235b of FIG. 24.

It can be shown that the temperature dependence is linear with respect to changes in sample temperature—see further the explanation below. Therefore, for each wavelength, the gradient of the intensity value with respect to temperature provides information to characterise the change in transmission intensity with changes in temperature. This gradient data is obtained as described earlier and stored in the drug/dilutant data base along with the spectral training data.

Using the temperature dependence data in the training set data base (the gradient of intensity with respect to temperature; one gradient for each wavelength for each undiluted drug), the processor generates a new training data set for all undiluted drugs and dilutants at the same temperature as the blind test sample was measured at, namely, $T_b$. This temperature correction is applied to data for all retainers (e.g. test tubes) in the original reference training data set (which has had dark current eliminated as above). This results in a set of temperature corrected training data that are the next step in obtaining the comparison coefficients for verifying/identifying the unknown sample under test. Temperature correction applied to the training data set in this manner allows a direct comparison to be made with data acquired for the blind test since all data is now converted to/valid at the blind test sample temperature, $T_b$.

As previously described, when performing a blind test on an unknown drug sample, intensity data is measured at different wavelengths and the temperature is taken of the sample and also stored in the database 23. With the temperature of the fluid known, a set of temperature-corrected training data coefficients is generated for all drugs in the data base corresponding to the temperature of the unknown drug measured in the blind test. Therefore, both the blind test concentration-independent coefficients and those of the training data set have a common temperature.

Referring to FIG. 24, step 235b, temperature compensation occurs as follows. For each drug in the training set, the set of training data is taken and for each training data value (with dark current eliminated) $N_1$ to $N_n$ at each wavelength, the dark current corrected intensity value is then corrected for temperature using the following equation in the processor 18:

$$I(T_t) = I(T_b) + \frac{dI}{dT}\Delta T \quad (6)$$

Where in (6),
I is the intensity of affected electromagnetic radiation detected by a detector at a particular wavelength for a sample (with dark current eliminated e.g. N),
$T_t$ is the temperature of the training sample when the affected electromagnetic radiation was detected at that wavelength,
$T_b$ is the temperature of the unknown sample when the affected electromagnetic radiation was detected at that wavelength,
$\Delta T=T_t-T_b$ is the sample temperature difference between the training sample temperature and unknown sample temperature, and $$\frac{dI}{dT}$$

is the slope of the linear relationship of between measure intensity and temperature for a sample at a given wavelength.

All parameters are known from the training data and blind test data.

In particular, the equation is rearranged to solve for $I(T_b)$: $I(T_b)=I(T_t)-(dI/dT)\Delta T$. Each intensity I $(T_t)$ is obtained (being the intensity of the training sample obtained during training) along with $$\frac{dI}{dT}$$

and $\Delta T$. For each intensity I $(T_t)$ from the training data, a corresponding a temperature corrected $I(T_b)$ is obtained using the rearranged equation (6) and stored—this correlating to an "expected" intensity for the unknown drug at the blind test temperature if the unknown drug were the training drug. $I(T_b)$ is the temperature corrected intensity. This corrected $I(T_b)$ is what is used to calculate the training coefficients below.

The temperature correction is not applied to the reference data if it comes from the monitor diode 4. However, if it comes from a reference channel with components and/or a sample the temperature correction does take place as described above.

After this step, the processor 18/database 23 now has a set of training data $(I(T_b)_1$ to $I(T_b)_n)$ for each drug in the training set that represents intensities that have had dark current eliminated and have been temperature corrected to match the temperature of the unknown sample under test.

Derivation of Temperature Correction

When performing a blind test on an unknown drug sample, intensity data is measured at different wavelengths and the temperature of the sample are stored. With the temperature of the fluid known, a set of temperature-corrected training data coefficients is generated for all drugs in the data base corresponding to the temperature of the unknown drug measured in the blind test. Therefore, both the blind test concentration-independent coefficients and those of the training data set have a common temperature.

The temperature correction is implemented by exploiting the experimentally observed linear relationship between measured intensity and temperature for a given drug at a particular wavelength as set out below. Thus, the temperature dependence of a given drug can be measured and characterised by a single coefficient at each wavelength of interest which corresponds to the slope of the measured intensity with respect to temperature change.

For a given drug in the training data set, at a given wavelength, we can express the intensity at temperature $T_0+\Delta T$ in terms of that at temperature, $T_0$ as follows:

$$I(T_0 + \Delta T) = I(T_0) + \frac{dI}{dT}\Delta T \qquad (A6)$$

Equation (A6) is equivalent to equation (6)
In (A6), the slope $$\frac{dI}{dT}$$

is a constant coefficient that is known for each drug in the data base. These coefficients are determined by measurement on each dilutant and undiluted drug of interest. There is a separate coefficient for each wavelength. These temperature coefficients form part of the training data set.

The temperature $T_0$ in (A6) is defined as the temperature at which the original training data measurements were performed (as determined from the temperature sensor in the fluid test cell holder). This need not be the same for each entry in the data base, and can be different for each wavelength.

The temperature deviation from $T_0$ is denoted by $\Delta T$. This is determined by measuring the fluid temperature of the unknown drug under test (the blind test) and subtracting the known value of $T_0$. Thus, a temperature-corrected set of concentration-independent training coefficients can be generated at the same temperature as the blind test measurement using the linear correction formula of (A6).

Retainer Tolerance Sensitivity Reduction

The sample retainer 16 could be a test tube, cell, IV line, syringe or other suitable retainer having a transparent wall. Inaccuracies due to tolerances in the sample retainer wall and path length and any other geometric and/or material parameters can be reduced. For example, during blind or training tests, the fluid (sample) thickness is controlled by having a fixed cavity bounded by two optically transparent walls typically made of a plastic. In the present invention, such plastic retainers are designed to be a consumable product that is used just once prior to disposal. Although well-controlled during the manufacturing process, inevitably there are minor deviations from the intended nominal fluid thickness from tube to tube due to manufacturing tolerances. Typically, for a nominal fluid thickness of e.g. several mm there will be a dimensional tolerance of +/−15 microns. This dimensional uncertainty from tube to tube translates into a spread in measured intensity values for a given fluid around the mean value associated with a retainer of nominal thickness.

In overview, in order to reduce the sensitivity of the intensity data to variations in the retainer (e.g. test tube) geometry (due to manufacturing tolerances) the following 'retainer correction' algorithm has been found to work well which generates normalised ratios of the intensity values for the training data and blind test data, step 235c. This algorithm is applied to both training data and blind test data after dark current and temperature correction has been applied. Details of the derivation of this algorithm are set out below. While not necessarily a correction as such, the algorithm produces coefficients that render the verification/identification process less sensitive to retainer tolerance/variations.

The process will now be described in more detail with reference to FIG. 8, step 235c. The ratio of the sample intensity to the reference intensity for each wavelength (from the compensated training data or blind test data as appropriate) is then evaluated by the processor, for each retainer (in the case where multiple tests are carried out on the same sample in multiple retainers). Second, the ratio data is normalised by the processor for each retainer with respect to the sum-over-wavelengths. Mathematically, this is described below.

Firstly, for each undiluted drug and dilutant in the training set, for each wavelength, the average is found over the number of scans for the set of reference raw data intensities (however obtained, e.g. by monitor diode or via a reference channel) and the set of training data raw intensities $((I(T_b)_1$ to $I(T_b)_n)$ in the case where both the reference and training data set have been processed for dark current and temperature correction as described earlier). The ratio $f_m$ of these averages (being training raw data average intensities divided by the reference raw data average intensities) is found for each wavelength, for each, retainer. Secondly, the ratio data is normalised for each tube with respect to the sum-over-wavelengths. Mathematically, this is described below.

Denoting the ratio at the $m^{th}$ wavelength by $f_m$, the normalised ratios are given by the parameter $g_m$ as follows:

$$g_m = \frac{f_m}{\Sigma f_m} \qquad (7)$$

The same is also carried out for the sample data as required. That is, for the sample drug and dilutant, for each test wavelength, the average is found over the number of scans for the reference raw data intensities (however obtained, e.g. by monitor diode or via a reference channel) and the unknown sample data raw intensities (both of which may have been processed for dark current and temperature correction). The ratio $f_m$ of these averages (unknown sample raw data average intensities divided by the reference raw data average intensities) is found for each (test) wavelength. Secondly, the ratio data is normalised for each tube with respect to the sum-over-wavelengths. Mathematically, this is described in equation (7) above.

The $g_m$ values represent the fractional (spectral) intensity (also termed "fractional ratio") defined as the proportion of transmitted light measured at the $m^{th}$ wavelength referenced to the sum of intensities over all test wavelengths measured for a given retainer. The values of g always lie between 0 and 1 since they represent fractions of the total amount of energy received over all test wavelengths measured.

For the temperature corrected and dark current eliminated training data, a set of $g_m$ values ($g_{m1}$ to $g_{mn}$) for each retainer used is obtained as per equation (7). The same procedure is applied to the dark current corrected blind test data to obtain a set of $g_m$ values ($g_{m1}$ to $g_{mn}$) for the retainer used.

This results in a set of $g_m$ coefficients ($g_{m1}$ to $g_{mn}$) for each drug, that are stored in the processor 18/database 23 and that form the basis of training and blind test coefficients that can be calculated (as set out further below) that can be used for verification/identification purposes with reduced sensitivity to retainer geometry.

Derivation for Retainer Tolerance Sensitivity Reduction

Measurements of intensity for the fluid under test are carried out using a purpose-made test tube (vial) which contains the fluid sample. The fluid thickness is controlled by having a fixed cavity bounded by two optically transparent walls typically made of a plastic. A typical fluid thickness is several mm with the plastic walls having a comparable total thickness. In the present invention, such plastic test tubes are designed to be a consumable product that is used just once prior to disposal.

Although well-controlled during the manufacturing process, inevitably there are minor deviations from the intended nominal fluid thickness from tube to tube due to manufacturing tolerances. Typically, for a nominal fluid thickness of several mm there will be a dimensional tolerance of +/−15 microns for an injection-moulded component. This dimensional uncertainty from tube to tube translates into a spread in measured intensity values for a given fluid around the mean value associated with a tube of nominal thickness. This error can be expressed mathematically for the $m^{th}$ wavelength in the measurement set using the Beer-Lambert law as a starting point, namely:

$$f_m = \left(\frac{I}{I_0}\right)_m = T_m e^{-2\bar{\alpha}_m w} e^{-2\alpha_m d} \quad (B1)$$

where in (B1):
I=Measured transmitted intensity through the fluid in its test tube (in this case temperature corrected $I(T_b)$).
$I_0$=Incident intensity on the test tube (proportional to the reference channel reading).
$T_m$=Transmission factor involving the refractive indices of the test tube wall and fluid that accounts for reflections at the material interfaces.
$\bar{\alpha}_m$=Attenuation coefficient of test tube wall material with total thickness, w, at $m^{th}$ wavelength.
$\alpha_m$=Attenuation coefficient of fluid with thickness, d, at $m^{th}$ wavelength.

By way of example, consider the sensitivity of the measured transmission coefficient $f_m$ with respect to changes in the fluid thickness, d. Differentiating (B1) with respect to d while keeping all other variables constant gives:

$$\frac{\partial f_m}{\partial d} = -2\alpha_m f_m \quad (B2)$$

Defining the nominal fluid thickness as $d_0$ and the deviation from this value as $\Delta d$, the resulting effect on the measured intensity can be expressed as:

$$f_m(d_0 + \Delta d) = f_m(d_0) + \frac{\partial f_m}{\partial d}\Delta d \quad (B3)$$

Combining (B2) and (B3) gives the error term $f_m$ as:

$$\Delta f_m = f_m(d_0 + \Delta d) - f_m(d_0) = -2\alpha_m f_m \Delta d \quad (B4)$$

Measurements carried out on fluids using numerous test tubes of the same nominal design have shown that errors of the form given in (B4) are consistent with the typical dimensional tolerance associated with the fluid space, d. It has also been found that these tube-to-tube variations can be comparable or larger in magnitude than the difference between mean intensity values between some drugs. This makes drug discrimination for certain drugs very difficult or even impossible.

To remedy this, an alternative measurement parameter is considered which is less sensitive to the dimensional tolerances associated with the test tubes. This parameter is the fractional intensity, denoted by $g_m$, which is defined as the proportion of transmitted light measured at the $m^{th}$ wavelength referenced to the sum of intensities over all wavelengths measured for a given test tube. That is we define:

$$g_m = \frac{f_m}{\Sigma f_m} \quad (B5)$$

The values of $g_m$ always lie between 0 and 1 since they represent fractions of the total amount of energy received over all wavelengths measured. To estimate the sensitivity of $g_m$ to dimensional tolerances in the fluid thickness, we follow a similar procedure to before using partial differentiation with respect to the fluid thickness, d. Denoting $\Sigma f_m$ by $\Sigma$, this gives:

$$\frac{\partial g_m}{\partial d} = \frac{1}{\Sigma}\frac{\partial f_m}{\partial d} - \frac{f_m}{\Sigma^2}\frac{\partial \Sigma}{\partial d} \quad (B6)$$

Using (B6) and noting that, using (B2), $$\frac{\partial \Sigma}{\partial d} = -2\Sigma \alpha_m f_m$$

we can express the error term $\Delta g_m$ associated with $g_m$ in the following form:

$$\Delta g_m = g_m(d_0 + \Delta d) - g_m(d_0) = \frac{\Delta f_m}{\Sigma} - \frac{f_m}{\Sigma^2}\Sigma_m \Delta f_m \quad (B7)$$

Inspection of (B7) indicates that the spread in values, $\Delta g_m$, associated with dimensional tolerances in the fluid thickness in the test tube are reduced in magnitude when we use the fractional intensity $g_m$ instead of the transmission coefficient $f_m$. This is by virtue of the denominator terms in (B7) which involve the factors $\Sigma$ and $\Sigma^2$ which are larger than unity.

We now consider the case of the fractional intensity parameter for a test tube of nominal fluid thickness $d_0$ when the fluid attenuation coefficient changes, as would occur when performing measurement s on different drugs. If the fluid attenuation coefficient changes from $\alpha_m$ to $\alpha_m + \Delta\alpha_m$ then the effect on the fractional intensity is as follows:

$$g_m(\alpha_m + \Delta\alpha_m) = \frac{f_m(\alpha_m + \Delta\alpha_m)}{\Sigma f_m(\alpha_m + \Delta\alpha_m)} = \frac{f_m(\alpha_m)(1 - 2d_0\Delta\alpha_m)}{\Sigma f_m(\alpha_m)(1 - 2d_0\Delta\alpha_m)} \quad (B8)$$

In (B8), variations in attenuation coefficient in the denominator will be negligible compared to those in the numerator. Therefore, we can write (B8) as:

$$g_m(\alpha_m + \Delta\alpha_m) \cong \frac{f_m(\alpha_m)(1 - 2d_0\Delta\alpha_m)}{\Sigma f_m(\alpha_m)} = g_m(\alpha_m)(1 - 2d_0\Delta\alpha_m) \quad (B9)$$

Therefore, from (B9), the fractional change in the parameter, $g_m$ with respect to changes in the fluid attenuation coefficient is given by:

$$\frac{g_m(\alpha_m + \Delta\alpha_m) - g_m(\alpha_m)}{g_m(\alpha_m)} \cong -2d_0\Delta\alpha_m \quad (B10)$$

Equation (B10) establishes that the fractional intensity parameter $g_m$ remains sensitive to changes in fluid attenuation coefficient and so is suitable as a drug discrimination parameter. The use of the fractional intensity parameter $g_m$ has been tested with measured data obtained using multiple test tubes containing the same fluid. The resulting spread in values across different tubes was found to be greatly reduced compared to values obtained using just the measured transmission coefficients, thereby verifying the theoretical result of (B7).

It was also found that the inherent differences in the attenuation coefficients of different drugs were still maintained when using the fractional intensity parameter, which verified the result of (B10).

The reduction in sensitivity to fluid thickness variations from test tube to test tube proved to be a key factor in discriminating between drugs which had previously proven impossible to tell apart from just the transmission coefficient data alone.

Concentration Independent Coefficients

Having applied dark current, temperature correction and path length correction as described above resulting in the $g_m$ coefficients from the training data and blind test data, the next step is from that to generate a set of spectral (comparison) coefficients at each wavelength for a given drug-dilutant combination that are independent of concentration, step 235d, for both the training sample drugs and unknown sample drug under blind test.

It has been shown experimentally and theoretically that the intensity for a given drug-dilutant combination is linearly dependent on the concentration. Consequently, it is possible to characterise this dependence using the slope of the resulting straight line with respect to the volume fraction of undiluted drug, denoted by x. Here, x=0 corresponds to the case of pure dilutant, and x=1, the case for the pure undiluted drug. Details of the derivation of the concentration-independent coefficients are set out below.

Referring to FIG. 24, step 235d, the steps involved in calculating in the processor the concentration-independent coefficients are given below: First choose a dilutant—for example, 0.9% saline. Next, from the compensated training data set obtain/evaluate, as set out previously, the average-over-test-tubes for the $g_m$ values for the chosen dilutant and for each undiluted drug. There will be one such average value for each drug and the chosen dilutant for each wavelength (suffix m). Denote the undiluted drug tube averages by $\overline{g_m}$ and those of the dilutant as $\overline{g_m^0}$. For the blind test data, (for which there is only a single retainer), also obtain/evaluate $g_m$ value denoted by $g_m^B(x)$ where x is the unknown concentration (superscript B for blind test). Next, for each drug, subtract the dilutant tube average from each undiluted drug tube average, to give the slope, $s_m$, of the intensity versus concentration curve for each drug-dilutant combination, that is:

$$s_m = \overline{g_m} - \overline{g_m^0} \quad (8)$$

Next, the processor carries out the same steps for each further dilutant. Next, the processor evaluates the training-set coefficients $y_m$ as follows:

$$y_m = \frac{s_m}{\sqrt{\Sigma_m s_m^2}} \quad (9)$$

These coefficients are the slopes of equation (8) normalised with respect to the root-sum-of-squares taken over all wavelengths. These coefficients are independent of the concentration x and are defined at each wavelength for a given undiluted drug and its chosen dilutant.

Next, we now turn our attention to the blind data for which the drug identity and concentration are both unknown. For the case of a mixture of drug and chosen dilutant with unknown concentration, x, the linear dependence on concentration for the spectral intensity, $g_m^B(x)$ at the $m^{th}$ wavelength can be defined by the following:

$$g_m^B(x) - \overline{g_m^0} = s_m^B x \quad (10)$$

Where in equation (10) the concentration slope for the blind test drug is denoted by $s_m^B$ which, along with the concentration, x, is unknown.

Using equation (10) and the equation given in (9), a set of concentration-independent coefficients for the blind test drug, $y_m^B$, can be evaluated by the processor as follows:

$$y_m^B = \frac{s_m^B}{\sqrt{\Sigma_m (s_m^B)^2}} = \frac{g_m^B(x) - \overline{g_m^0}}{\Sigma_m (g_m^B(x) - \overline{g_m^0})^2} \quad (11)$$

Equation (11) shows that the above coefficients $y_m^B$ can be determined from the measured values of $g_m^B(x)$ and the known dilutant values $\overline{g_m^0}$ obtained from the training data set.

Since there will be several possible dilutants used, if the identity of the dilutant is not known or in doubt, the above procedure can be repeated for each different dilutant giving rise to a different set of concentration-independent coefficients for both training data and blind test data. The full set of $y_m$ and $y_m^B$ would therefore, in general, consist of coefficients for all dilutants of interest.

Using the equations 9 and 11, the processor obtains $y_m$ resulting in a set ($y_{m1}$ to $y_{mn}$) of training data coefficients for each drug, and $y_m^B$ resulting in a set ($y_{m1}^B$ to $y_{mn}^B$) of blind test data coefficients (together "comparison coefficients"), which are stored in the processor 18/database and can be used for verification identification.

Derivation of Concentration Independent Coefficients

The properties of each fluid of interest can be characterised by its complex refractive index. We can write the complex refractive index of the fluid under test, n, in terms of its real and imaginary parts n' and n" as:

$$n = n' - jn''  \quad (C1)$$

where in (C1): $j = \sqrt{-1}$.

Physically, the real part of the refractive index, n', determines the wavelength of electromagnetic radiation in the fluid according to $\lambda = \lambda_0/n'$ where $\lambda_0$ is the wavelength in free space. More importantly for NIR transmission through aqueous fluids, the imaginary part of the refractive index, n", determines the attenuation (via absorption) of incident electromagnetic waves consistent with the Beer-Lambert law as follows:

$$\frac{I}{I_o} = e^{-2\alpha d} \quad (C2)$$

In (C2), the transmitted light intensity through the fluid is denoted by I with $I_0$ the intensity incident on the fluid sample. The thickness of the fluid is denoted by d and $\alpha$ is the attenuation coefficient which is given by:

$$\alpha = \frac{2\pi}{\lambda_0} n'' \quad (C3)$$

Therefore, the measured attenuation through a fluid under test at a given free-space wavelength is determined by the imaginary part of the complex refractive index of the fluid. A common occurance in the preparation of intravenous drugs prior to administration, is dilution of a drug with a dilutant such as saline or water. Drug verification under these circumstances has the additional complication of drug concentration which needs to be accounted for in any subsequent verification analysis. The following procedure is applied to obtain a set of coefficients for each undiluted drug that is independent of the drug's concentration when the identity of the dilutant is known.

Consider the diluted drug as a mixture of two fluids, each denoted by subscripts '1' and '2', with complex relative permittivities $\epsilon_1$ and $\epsilon_2$, respectively. The complex relative permittivity of the fluid under test is denoted by $\epsilon$ and is related to the complex refractive index, n, of the fluid by the relation:

$$\epsilon = n^2 \quad (C4)$$

This complex relative permittivity can be expressed in terms of the complex relative permittivities of the individual components and the volume fraction of each component by invoking the Lichtenecker mixture law [ref 1] which is given below:

$$\frac{\epsilon}{\epsilon_1} = \left(\frac{\epsilon_2}{\epsilon_1}\right)^x \quad (C5)$$

In (C5), x denotes the volume fraction of component '2' which we can define as the undiluted drug, with component '1' the dilutant. Thus, when x=0, the mixture consists of 100% dilutant, and when x=1, the mixture is 100% undiluted drug.

Until recently, this formula was regarded as semi-empirical in nature without any firm physical basis. However, in 2010, the formula was derived from first principles by Simpkin [ref 2] using Maxwell's equations and the conservation of charge.

Equation (C5) can now be expressed in terms of the complex refractive indices of the relevant media by substituting (C4) into (C5) and taking the square root of each side. This gives the self-same formula for the complex refractive indices of the mixture, namely:

$$\frac{n}{n_1} = \left(\frac{n_2}{n_1}\right)^x \quad (C6)$$

Where $n_1$ is the complex refractive index of the dilutant and $n_2$ is the complex refractive index of the undiluted drug with volume fraction x.

We now express the complex refractive index of the undiluted drug in terms of the difference, $\Delta n$, with respect to that of the dilutant, that is:

$$n_2 = n_1 + \Delta n \quad (C7)$$

Substituting (C7) into (C6) gives:

$$\frac{n}{n_1} = \left(1 + \frac{\Delta n}{n_1}\right)^x \quad (C8)$$

For the case of intravenous drugs, the complex refractive index is dominated by the properties of water and deviations in complex refractive index from that of water are small in magnitude. Therefore, in (C8), the fraction $\Delta n/n_1$ is small compared with unity so that to a very good approximation we can expand the right hand side in a Binomial series and use only the first few terms. Thus, (C8) becomes:

$$\frac{n}{n_1} \cong 1 + x\frac{\Delta n}{n_1} \quad (C9)$$
$$\Rightarrow n \cong n_1 + x\Delta n = n_1 + x(n_2 - n_1)$$

Therefore, the mixture law for the two fluids is well-approximated by a linear relationship with respect to the volume fraction of the undiluted drug. Taking the imaginary part of both sides of (C9) then gives:

$$n'' = n_1'' + x(n_2'' - n_1'') \quad (C10)$$

If we now take the natural logarithm of the Beer-Lambert law of equation (C2) and substitute for the attenuation coefficient $\alpha$ using (C3), we obtain:

$$-\ln\left(\frac{I}{I_0}\right) = 2\alpha d = \frac{4\pi d}{\lambda_0} n'' \quad (C11)$$

If I represents the measured transmitted intensity of a diluted drug, then we can substitute for n" using equation (C10) to obtain the following:

$$-\ln\left(\frac{I}{I_0}\right) = \frac{4\pi d}{\lambda_0}\{n_1'' + x(n_2'' - n_1'')\}$$

The above expression can be expressed as follows:

$$\ln\left(\frac{I}{I_0}\right) = (1-x)\ln\left(\frac{I_1}{I_0}\right) + x\ln\left(\frac{I_2}{I_0}\right) \quad \text{(C12)}$$

where in (C12):

$$\ln\left(\frac{I_1}{I_0}\right) = -\frac{4\pi d}{\lambda_0} n_1''$$

is the Beer-Lambert law applicable to the pure dilutant with measured intensity $I_1$, and $$\ln\left(\frac{I_2}{I_0}\right) = -\frac{4\pi d}{\lambda_0} n_2''$$

is the Beer-Lambert law applicable to the undiluted drug with measured intensity $I_2$.

The above can be further simplified since the incident intensity $I_0$ cancels out in (C12) to give:

$$\ln\left(\frac{I}{I_1}\right) = x\ln\left(\frac{I_2}{I_1}\right) \quad \text{(C13)}$$

Equation (C13) shows that the measured intensities obey a logarithmic mixture law identical to the Lichtenecker formula. Expressions like those in (C13) can be applied to a given drug-dilutant mixture for each of several wavelengths measured.

In (C13), we can simplify the logarithmic expressions by observing that the measured spectral intensities differ only slightly for different drugs. That is, the ratios $$\left(\frac{I}{I_1}\right) \text{ and } \left(\frac{I_2}{I_1}\right)$$

are close to unity. Therefore, we can write the following approximations:

$$\ln\left(\frac{I}{I_1}\right) = \ln\left(1 + \frac{(I-I_1)}{I_1}\right) \cong \frac{(I-I_1)}{I_1}$$

and $$\ln\left(\frac{I_2}{I_1}\right) = \ln\left(1 + \frac{(I_2-I_1)}{I_1}\right) \cong \frac{(I_2-I_1)}{I_1}$$

which are valid since $I-I_1$ and $I_2-I_1$ are small in magnitude with respect to $I_1$. Using these approximations in (C13) results in the following linear expression:

$$I(x) - I_1 = (I_2 - I_1)x \quad \text{(C14)}$$

Expressions of the form given in (C14) can be defined for each wavelength. The important point to note is that the volume fraction of the undiluted drug, x, which is a measure of the drug concentration, is common to all wavelengths for a given mixture. Therefore, by making measurements at a minimum of two wavelengths, it is possible to eliminate the concentration, x, and obtain values that are characteristic of the particular undiluted drug with respect to a given dilutant.

The optimum way to eliminate the concentration, x, that utilises measured data at all wavelengths, is proposed as follows. A normalisation procedure is used whereby the normalising factor is the root-sum-of-squares over all wavelengths. To illustrate this latter scheme, consider M wavelengths so that we obtain a set of M equations like that in (C14), one for each wavelength, $\lambda_m$, where m=1, 2, 3 ... M, namely:

$$I(x, \lambda_m) - I_1(\lambda_m) = (I_2(\lambda_m) - I_1(\lambda_m))x \quad \text{(C15)}$$

In (C15) we now square both sides, sum over all wavelengths (suffix m) and take the square root to give the following expression for x:

$$x = \sqrt{\frac{\Sigma_m (I(x, \lambda_m) - I_1(\lambda_m))^2}{\Sigma_m (I_2(\lambda_m) - I_1(\lambda_m))^2}} \quad \text{(C16)}$$

Substituting for x in (C14) using (C16) then gives for each wavelength a coefficient, $y_m$ defined as follows:

$$y_m = \frac{I(x,\lambda_m) - I_1(\lambda_m)}{\sqrt{\Sigma_m(I(x,\lambda_m) - I_1(\lambda_m))^2}} = \frac{I_2(\lambda_m) - I_1(\lambda_m)}{\sqrt{\Sigma_m(I_2(\lambda_m) - I_1(\lambda_m))^2}} \quad \text{(C17)}$$

By virtue of the far right-hand side of (C17), the coefficients $y_m$ are independent of the drug concentration and are characteristic of the undiluted drug and its dilutant.

When performing a blind test on an unknown drug, the coefficients are found by measuring the intensity $I(x,\lambda_m)$ for the unknown drug mixture at M wavelengths. For each wavelength, the difference between these measured intensities and the dilutant is then normalised with respect to the root-sum-over-squares over all wavelengths as per the first expression on the right hand side of (C17). The identity of the dilutant is assumed known and its intensity $I_1(\lambda_m)$, which will typically be contained within the set of training data. Usually, the dilutant is saline, water, or glucose. If the dilutant identity is not known, or is in doubt, concentration-independent coefficients for all possible combinations of dilutants and undiluted drugs can be determined for use in the drug verification analysis.

The consequence of (C17) is that when generating a set of training data, it is only necessary to measure the intensities of the dilutants of interest (denoted by $I_1(\lambda_m)$ in (C17) and the intensities of the drugs of interest in their undiluted form (denoted by $I_2(\lambda_m)$ in (C17). It is not necessary to generate training data for every possible combination of dilutant and drug—just data for each dilutant and each undiluted drug of interest. The set of training data for a range of drugs and dilutants is then populated by concentration-independent coefficients given by the far right-hand side of (C17).

Once a drug's identity has been verified from the blind test and training set coefficients so generated, it is possible to determine the concentration of the drug by calculating the value of x by back-substitution using (C15).

Drug Verification/Identification or Other Characterisation

Now that there exists a set of concentration-independent coefficients for each of the drugs in the training data set with its chosen dilutant—these are the training coefficients $y_m$ obtained from equation (9). Now there also exists a set of concentration-independent coefficients for the unknown blind test drug—these are the sample coefficients $y_m^B$ obtained from equation (11).

The drug identity is now verified/identified or otherwise characterised by the processor using, for example, Linear Discriminant Analysis, with $y_m$ as training data and $y_m^B$ as test data, step 235e. In general terms, the representative sample/training coefficients are found for the sample at each selected wavelength and with respect to each other comparison sample. The sample coefficients are analysed against the training coefficients. Representative value(s) could be obtained for each sample based on the coefficients. If there is sufficient similarity between the representative value(s) found for the unknown sample and the representative value(s) of a training sample (corresponding to the same sample), then verification or identification is made. Sufficient similarity can be determined using any suitable statistical or other technique. For example, sufficient similarity might occur when some or all of the representative values match those in the verification matrix. In another example, this might occur when the sample falls below the threshold for each comparison sample. An alarm or output might be made via a user interface to advise the user of the result of the verification/identification.

In verification, the $y_m^B$ values for the unknown sample are analysed against the $y_m$ values for the drug identified/entered by the clinician to see if there is a match. An output answer such as "Yes" or "no" can be output on the interface to advise the clinician if the blind test sample matches the expected input drug, step 236 of FIG. 23. In identification, the $y_m^B$ values for the unknown sample are analysed against the $y_m$ values for all training samples. The processor 18 can provide an output on the user interface for example advising the clinician what the sample drug is, step 236 of FIG. 23 and also control external equipment where appropriate.

Figure 25:
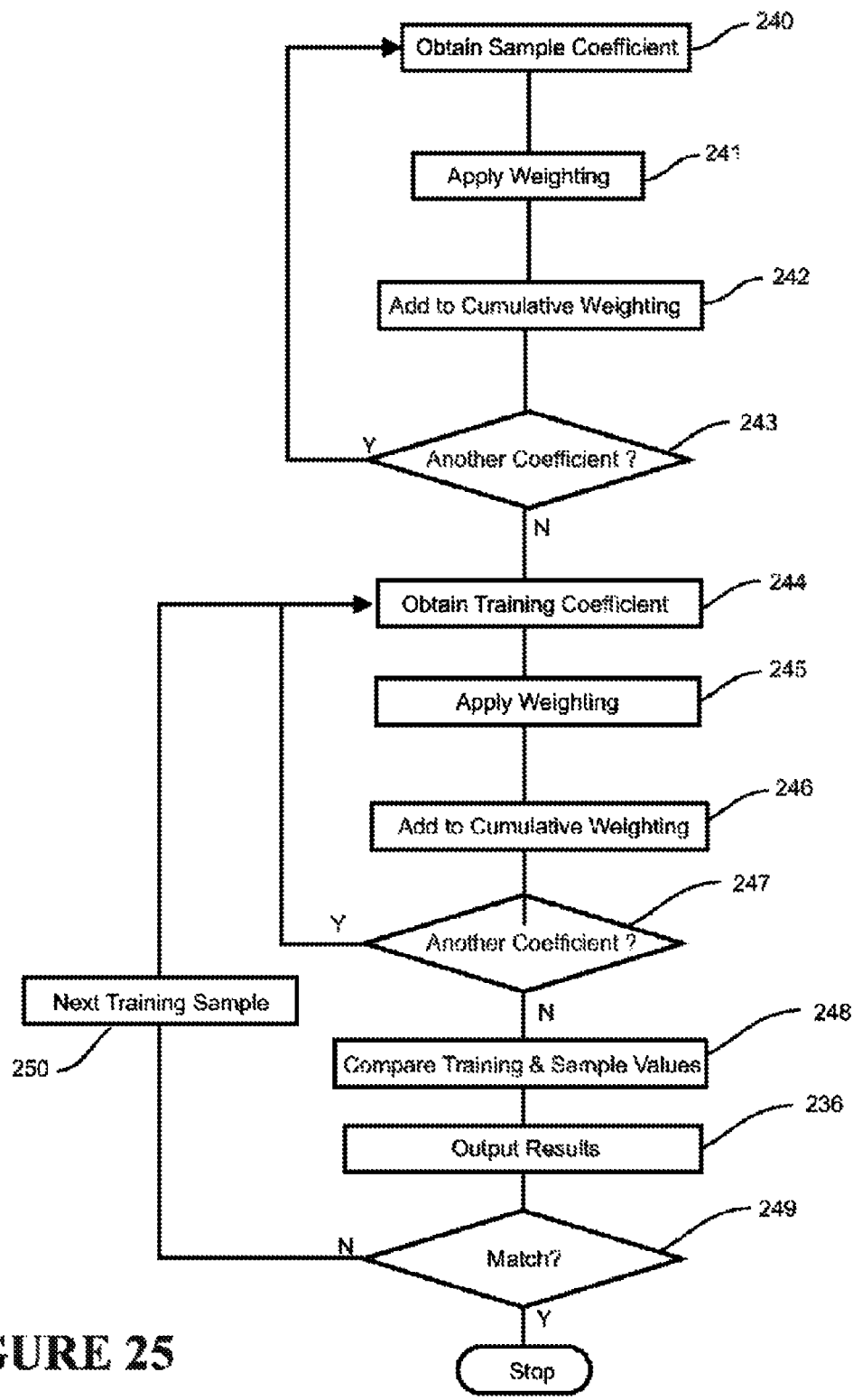

One possible embodiment of a verification/identification method is described with reference to FIG. 25 (which shows step 235e of FIG. 24 in more detail)—the processor 18 undertakes the steps. As previously described, each unknown sample and training sample have a set of coefficients, one for each wavelength. In overview, a linear score is defined for the set of coefficients for each sample by 6 weights—one for each wavelength: score=$w_1$×normalised value at wavelength 1+ . . . +$w_6$×normalised value at wavelength 6. In addition, for each score a threshold value is determined, τ, such that an alarm is raised when the score e.g. exceeds τ.

First a sample coefficient is obtained by the processor 18 from the database 23, step 240. It is then multiplied by or otherwise has a weighting applied to it, step 241. The weighting is added to a previous weighting for that sample, step 242. This provides a cumulative weighting which becomes a representative sample value for the sample. If all coefficients for the sample have been processed, step 243, the method moves to the next step. If not, step 243, the next coefficient is obtained, step 240, weighted, step 241, and added to the cumulative weighting, step 242 for that sample.

Next, the same process happens for the training sample coefficients—the processor 18 undertakes the steps. If verification takes place then following happens. The first coefficient is obtained by the processor 18 for the sample/drug that the clinician input previously as the predicted drug, step 244. It is then multiplied by or otherwise has a weighting applied to it, step 245. The weighting is added to a previous weighting for that training sample, step 246. This provides a cumulative weighting which becomes a representative training value for the training sample. If all coefficients for the sample have been processed, step 247, the method moves to the next step. If not, step 247, the next coefficient is obtained, step 244, for that training sample weighted, step 245, and added to the cumulative weighting, step 246 for that sample.

Next the cumulative representative training value and the cumulative representative sample value are compared or compared against a threshold(s) or some other relationship between them is determined, step 248. For example, if the sample value is within 'X' of the training value or if the sample value is above or below a threshold with some reference to the training value, then a "match" is determined, and the unknown sample is deemed the same as that of the training value. Otherwise it is deemed not to be a match. Output as previously described can then take place indicating the result, step 236. The process stops.

Where identification takes placed, steps 244 to 248 cycles through for all training sample coefficients for all training samples, step 249. That is, if the comparison step 248 results in no match, step 249, then the processor 18 determines the representative training sample value from the training coefficients for the next training sample in the database 23, steps 244 to 247. The training and sample representative values are compared, and it is determined whether a match occurs, step 248, and the result outputted step 236. If there is no match, step 249, steps 244 to 248 are repeated until all training sample coefficients have been analysed, or a match occurs.

It will be appreciated that the above embodiment is conceptual only and the actual steps taken and their order by a processor could be different. For example, training samples coefficients could be processed first. Many alternatives could be envisaged.

Determining Weights and Thresholds

The drugs below were tested using and apparatus and method as described in the first embodiment. The weights $w_1$ . . . $w_5$ are chosen by solving a linear program that provides a separation of 1 unit in the score. This is possible if the 'intended' drug is well-separated from the rest. However, even when it is possible to get a solution, there is, the issue of 'robustness'. Large weights are symptomatic of a lack of 'robustness'. To get a better idea of blind test performance we will need to add+/−1% to the training data and consider the resulting false and missed alarm rates. The threshold value r is chosen to give acceptable error rates (if possible).

Determination of Drug Concentration.

With the drug identity verified, the slope of the concentration curve $S_m$ can now be found by the processor using equation (8). Then, the concentration of the drug in its chosen dilutant can be found by the processor from back-substitution into equation (10) on setting $S_m^B = S_m$. Thus, the concentration, x, is given by:

$$x = \frac{g_m^B(x) - \overline{g_m^o}}{S_m} \quad (12)$$

The processor can provide output on the user interface advising the clinician what the concentration of the sample drug is.

It will be appreciated that in this embodiment that not all corrections or processing are essential. While the raw data is described as having dark current eliminated, temperature corrected, fractional intensities found, and concentration-independent coefficients found, a subset of these could be used. Further, the order in which they are described as occurring should not be considered limiting. It will also be appreciated that while temperature correction, fractional intensity and concentration independent coefficients are found after the blind test, this is not essential. Some or all of these might be found after the training test. A database 23 (e.g. in the form of a look up table) could be produced at training acquisition time or afterwards and then used by the characterisation process after the blind test. Training sample coefficients could be provided for e.g. all likely temperatures and then used by the processor 18 during characterisation.

It will also be appreciated that where verification takes place, it may not be necessary to process and compare all training data/coefficients. Rather, just the training data/coefficients for the identified drug are processed and compared to those of the unknown sample. In identification the training data/coefficients for several or all of the training samples may need processing/comparing with the unknown drug until a match is found.

Second Embodiment

One possible embodiment of the invention will now be described in detail by way of example. This should not be considered limiting but illustrative. The embodiment is described in relation to an apparatus for providing verification or identification of water based drugs from e.g. a set of 30 drugs.

Six wavelengths of electromagnetic radiation are chosen for this example, six being greater than $\log_2 n$ of 30. The wavelengths are chosen in the analysis range and are based on the spectral characteristics of water, being the base liquid, falling in that range. The spectrum of a water based drug (or other liquid based drug or aqueous solution) will be heavily dominated by the base liquid spectrum. For example referring to FIG. 5, the spectrum (dotted line) of drug W (gelofusine succinated gelatine solution 4%) is very similar to the spectrum of water (solid line). This is because the spectrum of water dominates. However, the differences in transmission coefficient between different water based drugs can be measured. Focussing on areas/wavelengths of spectral characteristics of the water spectrum, by using electromagnetic radiation beams at those wavelengths, the difference between the water spectrum and the water based drug spectrum at those wavelengths can be utilised to provide drug discrimination for drug identification or verification.

FIG. 6 shows a spectrum of water with some possible spectral characteristics (features) in the analysis range identified, and explained further below.

Spectral characteristic A (slope)—in a first region between 1300 nm and 1400 nm.
Spectral characteristic B (plateau/trough)—in a second region between 1400 nm and 1500 nm.
Spectral characteristic C (slope)—in a third region between 1500 nm and 1600 nm.
Spectral characteristic D (peak)—in a fourth region between 1600 nm and 1700 nm.
Spectral characteristic E (inflection)—in a fifth region between 1700 nm and 1800 nm.
Spectral characteristic F (knee) a sixth region between 1800 nm and 2000 nm.

This is not an exhaustive list of possible spectral features.

The selection of a wavelength for an electromagnetic radiation beam is not strictly fixed, and not necessarily solely based on spectral characteristics of the base liquid. It is influenced by the wavelength of spectral characteristics in spectrum of the base water of the drug sample, but in addition the selected wavelength can be based on other factors also. For example, in interest of cost effectiveness and a regularly obtainable supply chain, it might be preferable to use or select an alternative wavelength that is close to the spectral characteristic but not quite the same, if that alternative wavelength is easily obtainable by an off-the-shelf laser or other optical component.

For example, it is possible to use 1310 and 1550 nm as selected wavelengths for water based drugs as there are many devices configured for these wavelengths as they have wide spread use within the communications industry. Laser diodes nominally have centred wavelengths at 1650 nanometers, 1750 nanometers and 1850 nanometers, although these can be varied by up to plus or minus 30 nanometers. So wavelengths in these ranges can also be selected. Therefore by looking at the availability of these components, and the spectral characteristics of the base liquid, suitable wavelengths for the emitted radiation can be determined.

Therefore, based on the above explanation, each of the six wavelengths can be chosen to be within the vicinity or within the region spanning one of each of the spectral features, but also influenced by the availability of hardware. The six wavelengths for water could therefore be (by way of example): 1350 nanometers corresponding to feature A, 1450 nanometers corresponding to feature B, 1550 nanometers corresponding to feature C, 1650 nanometers corresponding to feature D, 1750 nanometers corresponding to feature E and 1850 nanometers corresponding to feature F, all which fall within the 1300-2000 nanometers. As can be seen the 1350 nm to 1850 nm wavelength selections do not match exactly to peaks and troughs and other spectral characteristics in the water spectrum, although are close. The selections also relate to operating wavelengths of available hardware. These are of course nominal wavelengths and the actual wavelength might vary in practice due to source 11 characteristics.

Figure 7:
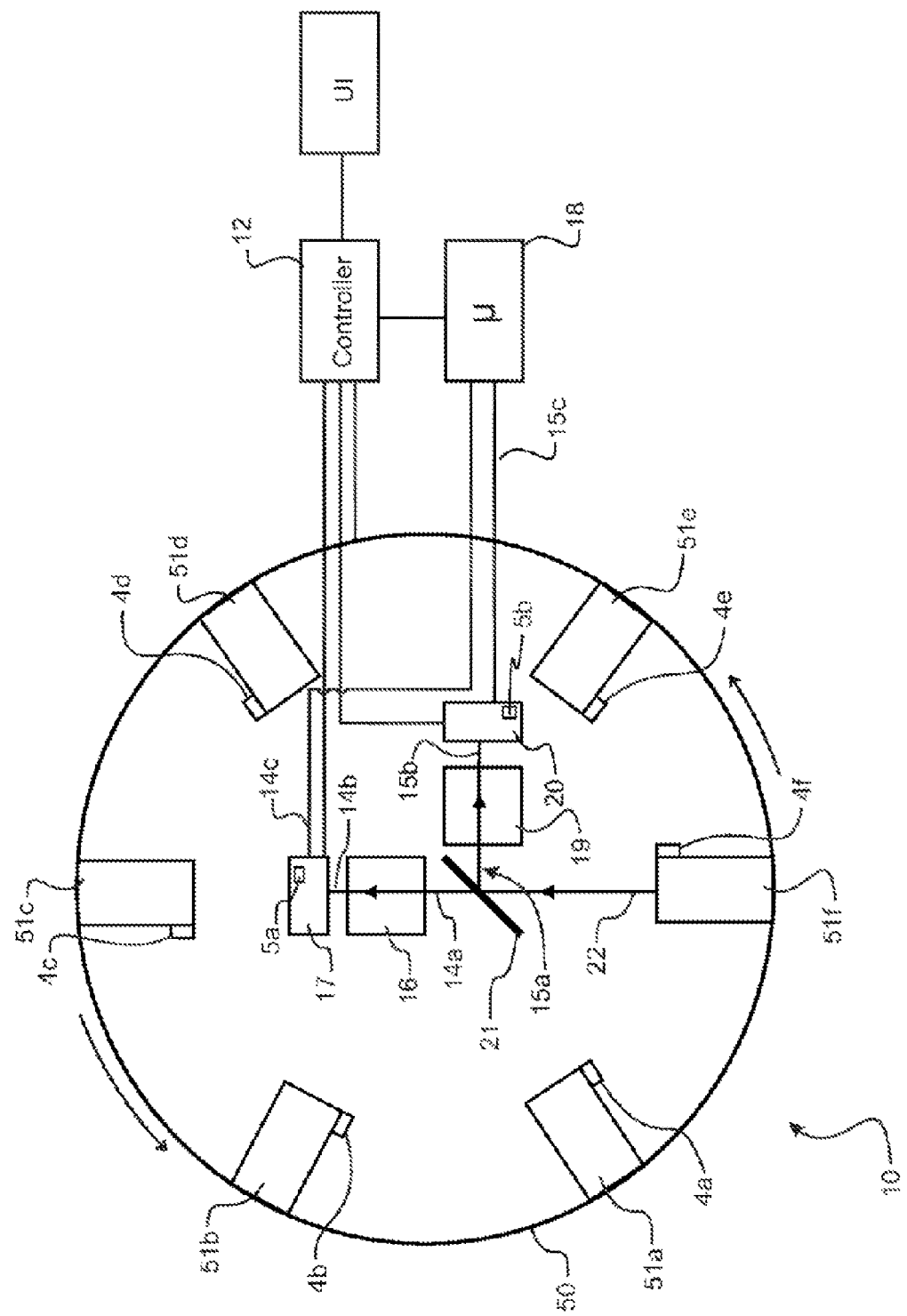
FIG. 7 shows a schematic diagram of a second embodiment of the spectroscopic analyser in which the sources are lasers on a rotating carousel.

FIG. 7 shows in schematic form one possible form of the apparatus 10 as generally described in FIG. 1. The spectroscopic analyser 10 has a controller 12 and a carousel 50 that supports six lasers 51a-51f, which together form the source 11 to output electromagnetic radiation 22 at a plurality of wavelengths in the form of light. Each laser is tuned or tuneable to emit electromagnetic radiation 22 at one of the six wavelengths defined above. Each laser can comprise or be formed from laser diodes providing a stable, high intensity, narrow band collimated electromagnetic radiation output that is readily controlled electronically via driver circuitry. Each laser comprises a lens that can collimate the emitted electromagnetic radiation 14a into a beam using appropriate lenses. Each laser 51a-51f can have one or more photodiodes 4a-4f for detecting output electromagnetic radiation for feedback control of that radiation. Lasers have fewer heat emission problems than other sources, thus reducing the detrimental effects of heat on the measurements. The output power of each laser preferably is nominally the same (typically 30 mW) in the interests of having a balanced apparatus. Preferably, this also enables a common diode driver circuit to be used for the laser diodes.

The controller 12 can control the carousel 50 to rotate about an axis to activate any one of the lasers 51a-51f in turn and align the activated laser (e.g. 51f as shown) to emit a beam 22 along the sample path/beam path 14a. The lasers 51a-51f can also be turned off completely to facilitate the measurement of dark current signals if required. The use of mechanically activated optical chopper can thereby be eliminated (although one can be included if desired.) Once activated, the laser emits electromagnetic radiation 22 towards the sample along the path 14a. The path 14a from the source to the detector is preferably predominantly via free-space preferably with minimal if any optical fibre components. This reduces optical attenuation and hardware. The apparatus also comprises a sample retainer 16a, which is aligned with the beam path 14a. The emitted electromagnetic radiation from an active laser 51a-51f is incident on and transmits or reflects through the sample 16 in the sample retainer.

The detector 16 is placed in the affected radiation path 14b that exits the sample 16a. Preferably the detector 16 is a single photodetector/photodiode biased to have a suitable response to detect electromagnetic radiation of wavelengths that will be in the affected radiation. A single detector reduces the errors due to variability introduced by components—it removes the relative differences between multiple photodetectors enabling a more stable response to the output of the emitted electromagnetic radiation thus enhancing sensitivity. An InGaAs photodiode could be used, for example. The detector 17 detects the affected radiation 14b and the output 14c of the detector 17 is passed to a processor 18 that verifies or identifies the sample as described above.

The apparatus also has a beam splitter 21 to redirect the incident electromagnetic radiation beam 22/14a towards a reference sample retainer along a reference path 15a, which passes through to a reference detector 20. The output of the reference detector 20 is also passed to the processor 18. The reference could be saline, for example.

Preferably, the apparatus also comprises a feedback system to stabilise the temperature of the electromagnetic radiation source 11 and the detectors(s). In one example, thermistors detect the temperature of the electromagnetic radiation source and/or detector(s). Peltier cooling devices can be operated to cool and stabilise the temperate of the source and detectors. The output of the thermistor(s) is sent to the controller, which controls the peltier cooling devices to cool the source and/or detectors. Preferably the thermistor is the built-in photodetector thermistor 5a, 5b. And the pettier thermo-electric cooler is built-in to the photodetector 5a, 5b.

Figure 4:
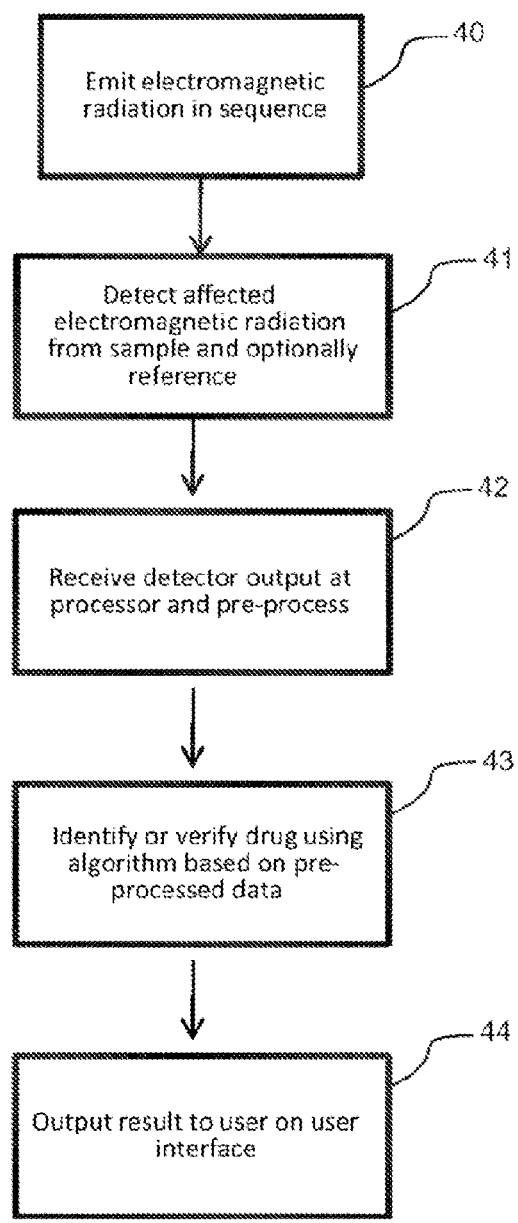
FIG. 4 is a flow diagram showing operation of the spectroscopic analyser.

Referring to FIG. 4, operation of the apparatus 10 will now be described. The controller 12 operates the carousel 50 to rotate each laser 51a-51f in turn to the activate position. When in the activate position, the laser 51a-51f is operated by the controller 12 to emit an electromagnetic radiation beam at one of the selected wavelengths to the sample 16 (and optionally to reference sample 19.) In this manner, six electromagnetic radiation beams with different selected wavelengths are emitted, step 40, in sequence from each of the six lasers 51a-51f, each tuned to a different selected wavelength. Each laser 51a-51f in turn emits an electromagnetic beam 22 along the path 14a towards the sample. The affected radiation coming from the sample is detected, step 41, for each electromagnetic radiation beam emitted 14a towards the sample 16. The electromagnetic radiation beam could be switched on and off to get a reading/measurement made by the detector during the off phase also—this can give a dark signal/current for reference purposes. The emitted electromagnetic radiation is also directed along the reference path 15a, through the reference sample 19 using the beam splitter 21, and detected by the reference detector 20. The outputs from the sample detector 17 and the reference detector 20 are passed to the processor 18, step 42. The processor (optionally) carries out pre-processing on the output from the detectors, and then verifies or identifies the drug based on the pre-processed outputs, step 43. It outputs the results via the user interface 24, step 44.

Figure 8:
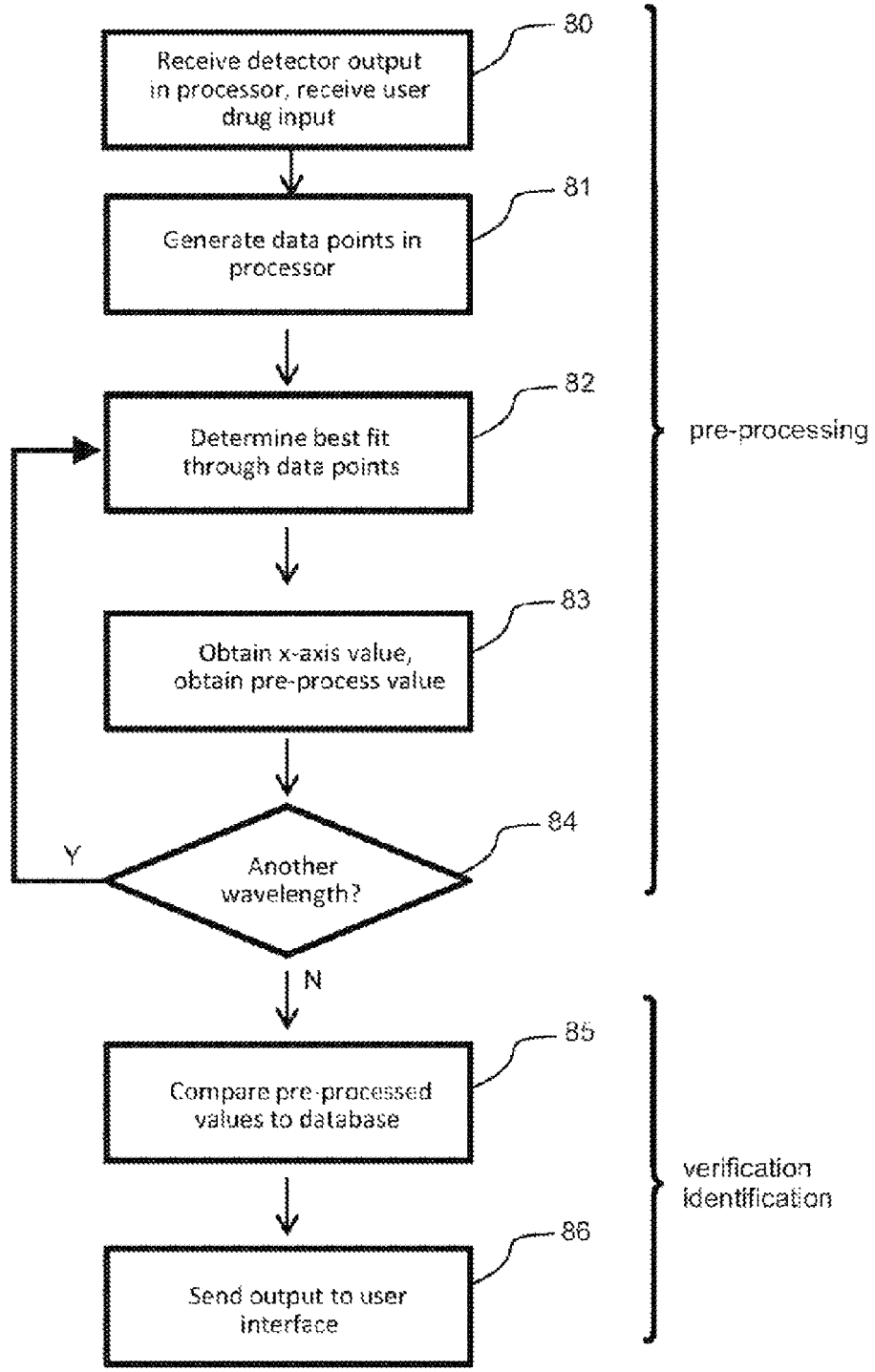
FIG. 8 shows a method of processing the output from the detectors, including a pre-processing and a verification/identification stage.

In one possible embodiment, the processor 18 comprises or implements a pre-processing method and then a verification/identification method as shown in FIG. 8. In this embodiment a reference channel is used and also dark current readings. Dark current is the output provided by the detectors 17, 20 when no electromagnetic radiation (e.g. light) is incident on them. This dark current reading from the detector can be subtracted from the actual reading from the detectors for calibration purposes. Having a dark reading is not essential for the invention and is described here as one possible option—the remaining description of the processing method would work also without dark readings being taken or by.

Figure 9:
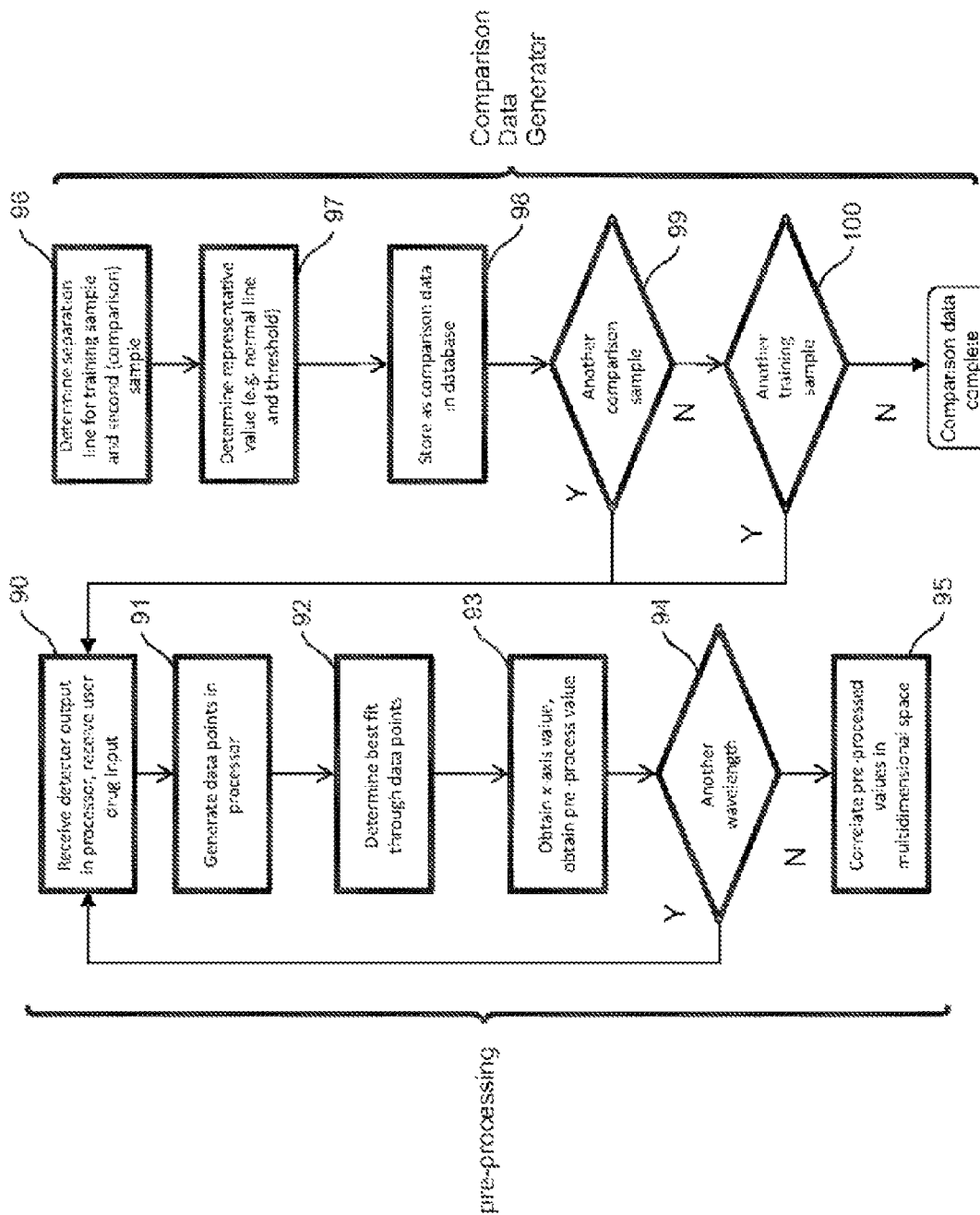
FIG. 9 shows a method of processing the output from the detectors, including a pre-processing and comparison data generation stage.
Figure 11:
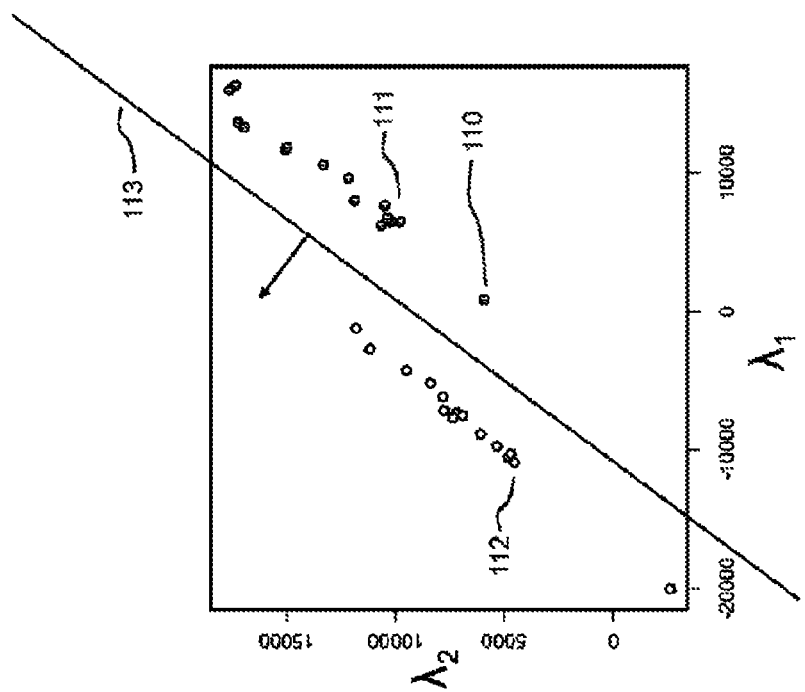
FIG. 11 shows a separation line between pre-processed data points for a training sample and a comparison sample.
Figure 10:
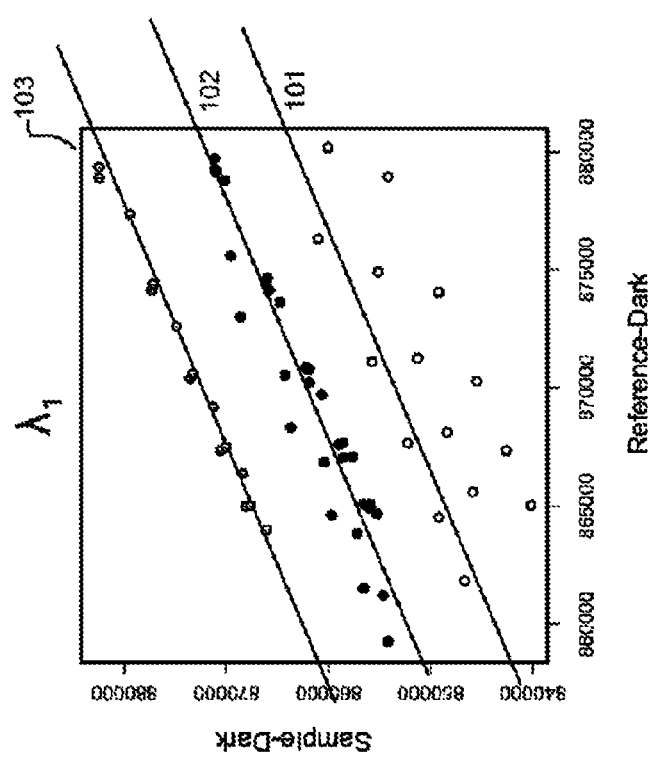
FIG. 10 shows a best fit line through data points obtained from outputs from the sample and reference detectors.

Prior to carrying out the verification or identification in FIG. 8, a training process is carried out to produce a comparison data from which samples can be verified/identified as shown in FIGS. 9-11. In the training process, an algorithm is used to generate the comparison data, which determines the particular linear combination of data values from each of the sample data that optimises the separation between different drugs. The resulting mathematical rule is then applied to the data acquired for the drug under test to verify that it is the intended drug. In the embodiment described, dark current readings are used. The training process preferably comprises a pre-processing stage, and a comparison data generation stage. Pre-processing is not essential, but improves performance.

Referring to FIG. 9, for the training process, a number of training samples are tested in the analyser in turn. Each training sample relates to a sample that will be test for during actual use of the analyser. For each training sample, output from both sample and reference channels is received at the processor, step 90. If dark current is being used, the output from each detector for the dark reading is subtracted from the output of the actual reading. The output 14c received at the processor 18 from the sample detector 17 indicates the intensity of the affected electromagnetic radiation 14b for each emitted electromagnetic radiation beam at the sample 16. It may, for example, comprise data which directly or indirectly indicates photocurrent of the detector and/or intensity of the detected electromagnetic radiation. Likewise, the output 15c received at the processor 18 from the reference detector 20 indicates the intensity of the affected electromagnetic radiation 15b for each emitted electromagnetic radiation beam at the reference sample. Preferably, the apparatus carries out multiple measurements for each wavelength. For example, at each wavelength, the apparatus detects affected electromagnetic radiation affected by the sample at 15 different times and passes this output to the processor, step 94. Similarly, at each wavelength, the apparatus detects affected electromagnetic radiation affected by the reference at 15 different times and passes this output to the processor, step 94.

Next, for each wavelength, the processor 18 generates from the output of the reference and sample detectors a range of sample data points for the sample that correlate an intensity of affected electromagnetic radiation 14b affected by the sample at a particular selected wavelength, step 91. These data points 100 could be plotted, as shown for example in FIG. 10—although it will be appreciated that the processor does not necessarily actually plot the data. The x axis shows intensity indicative values corresponding to detector output for the sample detector 17, and the y axis shows intensity indicative values correlating to detector output for the reference detector 20. The values indicate directly or indirectly the intensity of detected affected electromagnetic radiation. Where a reference channel is used, output on the reference detector is paired with output from the sample detector taken at the same time. Each sample/ reference channel detector output value pair is plotted on the graph. Such measurements can be taken for several times for each wavelength. Therefore, the plot in FIG. 10 shows the values indicative of intensity 103 measured at several times (e.g. 15) for a particular selected wavelength (e.g. nominally 1350 nm) of electromagnetic radiation incident 14a on the training sa 16 and on the reference 19.

For each training sample, the process is then repeated to get similar data points for a second (comparison) sample 101 and a control (e.g. saline) 102. The sample/reference channel detector output value pairs for the second (comparison) 101 sample and control sample 102 could also plotted on the graph, as shown in FIG. 9, step 91.

A best fit straight line can then be calculated using a suitable statistical technique, step 92, and the intercept value of the x axis is found, step 92, for each of the:

training sample set, 103
second (comparison) sample 101, and the
control sample 102 set of data points for the particular wavelength (1350 nm), as shown in FIG. 10.

From this a normalised pre-processed value is found. For example, the x-axis intercept values (e.g. 842500 and 850500) for the training sample 103 and control 102 respectively can be found, and then can be subtracted from each other to obtain normalised pre-processed values (e.g. 8000), step 93. Similarly, the x-axis intercept values (e.g. 86000 and 850500) for the second (comparison) sample 101 and control 102 respectively can be found also, and then subtracted from each other to obtain normalised pre-processed values (e.g. 95000), step 93. This process can be carried out for each of the other selected wavelengths (e.g. five others in this case), step 94 and steps 90-93, resulting in a set of six normalised pre-processed values (—one for each wavelength) for the training sample. The process can also be carried out for each of the other selected wavelengths for the second (comparison) sample, resulting in a set of six normalised pre-processed values for the second (comparison) drug for each wavelength. These sets of normalised pre-processed values for the training sample and second (comparison) for each wavelength sample can be correlated/plotted in a multidimensional space, each axis corresponding to a wavelength and the pre-processed value for that wavelength being plotted relative to that axis.

In practice, this process, steps 90-94, can then be carried out numerous times for each wavelength, so that for each training sample and second (comparison) sample, there are a plurality of sets of six normalised pre-processed values. Each set can be plotted/correlated as one point in a multi-dimensional (six dimensions in this case) space. An example of such a plot is shown in FIG. 11. Here, for simplicity, only a two dimensional space is shown, each axis relating to the results from two wavelengths—in reality it would need to be a six-dimensional graph to cover all six wavelengths. For each set for each of the training sample and second (comparison) sample, a pair of two normalised pre-processed value (i.e. one value for each wavelength) is plotted as a single point on the two dimensional graph, e.g. 110, resulting in a normalised pre-processed value data set for the training sample 111 and the second (comparison) sample 112.

The pre-processing stage described above reduces the detrimental effects of systematic errors in the system and drift in the measured data. Note, the reference channel/value is optional. In an alternative, x-axis intercept values are found for the sample data only.

In an alternative embodiment, the pre-processing steps previously described can be omitted on the grounds that system drift and systematic errors can be virtually eliminated with the use of highly stable laser diode sources and a reference signal derived from the laser's own monitor diode output. This facilitates the use of a single channel with a single photo-detector eliminating the need for separate optical reference channel and/or control sample to be used. To this end, the data base of measured transmission spectra for a range of intravenous drugs can be built up in a more straightforward manner by sequentially measuring samples of each drug in a single channel using multiple test tubes.

After the data has been pre-processed for the training sample and second (comparison) sample and correlated as shown in FIG. 11, a representative value can be obtained for the training sample. If no pre-processing is carried out, the process proceeds to finding the representative value on non-pre-processed (raw) data. First a line 113 that separates the training sample data set 111 from the second (comparison) sample data set 112 is determined, step 95. Then the normal direction of the line is used as a weighting in a score to separate the training sample from the comparison sample. Also, a threshold is determined below which the training sample falls, step 96. The threshold and weighting score provide a representative value for comparison data to assist in verification/identification for that training sample. The representative value is stored as comparison data in a database 23 for the training sample, step 98.

The entire process is the repeated (step 99, and steps 90-98) for the same training sample against a third (comparison) sample to get a second representative value for storing as comparison data in the database 23 for the training sample. Then the process is repeated again (step 99, and steps 90-98) against a fourth and subsequent comparison samples to generated a third and subsequent representative values for storing as comparison data for the training sample. Together these form the representative values in the comparison database to identify/verify the training sample.

The entire process (step 100, step 90-99) is the repeated for each other training sample (in the set of n drugs) against multiple comparison samples, in order to obtain representative values for each additional training sample also.

It will be appreciated that in describing the training process steps 90-100, there has been reference to graphs and techniques. These are described for illustrative purposes. Any processor carrying out the training process to determine representative values might not actually produce such graphs or utilise such techniques to obtain the end result, but rather use other processing techniques that achieve the same result.

The above training process will generate comparison data for each training sample (in the set of n drugs) that can stored in the database 23 and can be used to identify or verify actual samples from the set under test. The comparison database 23 can be generated well in advance of actual sample testing, or can be generated soon before or even on-the-fly. The comparison data can be considered as a multidimensional verification/identification matrix based on the acquired multidimensional spectral data from the detectors. The comparison data can be used to verify or identify any of the drugs from any of the other drugs in the set of n drugs.

Referring back to FIG. 8, once a comparison database is produced and stored in the database 23, verification/identification of actual samples occurs as follows. Output from both sample and reference channels is received at the processor, step 80. If dark current is being used, the output from each detector for the dark reading is subtracted from the output of the actual reading. The output 14c received at the processor 18 from the sample detector 17 indicates the intensity of the affected electromagnetic radiation 14b for each emitted electromagnetic radiation beam at the sample 16. It may, for example, comprise data which directly or indirectly indicates photocurrent of the detector and/or intensity of the detected electromagnetic radiation. Likewise, the output 15c received at the processor 18 from the reference detector 20 indicates the intensity of the affected electromagnetic radiation 15b for each emitted electromagnetic radiation beam at the reference sample. Preferably, the apparatus carries out multiple measurements for each wavelength. For example, at each wavelength, the apparatus detects affected electromagnetic radiation affected by the sample at 15 different times and passes this output to the processor, step 80. Similarly, at each wavelength, the apparatus detects affected electromagnetic radiation affected by the reference at 15 different times and passes this output to the processor, step 80.

This output is then preferably pre-processed, steps 81-84, in the same manner as described above for the training process and with reference to FIGS. 9 to 11. That description need not be repeated here, but in summary, data points are generated, step 81, best fit lines found, step 82, and x-axis values are obtained which provide normalised pre-processed values, step 83. This is done for all wavelengths, step 84. Pre-processing is not essential, but can improve performance.

After this pre-processing is carried out for the affected radiation of each wavelength, steps 81-84, the identification/verification algorithm can then be invoked, step 85. Verification involves confirming that a sample drug is the drug that is expected. For example, a clinician can specify what they think the drug is (e.g. from the set of n drugs) through the user interface 24, e.g. step 80, then use the apparatus to confirm whether the drug in the retainer is actually that drug which is specified by the clinician. Identification involves determining what a drug actually is, without any suggestion from the clinician as to what the drug is. For verification/identification, the spectral data (that is, the pre-processed values) are compared against the comparison data in the database 23, step 85, to identify the drug, or verify whether it is the anticipated drug as specified by the clinician. Output is then provided to the user interface, step 86.

In one possible identification/verification algorithm, once the sample data is obtained and pre-processed, representative values are found for the sample, in the same manner that they were found during the training process as explained with reference to FIGS. 9 to 11. The representative values are found for the sample at each selected wavelength and with respect to each other comparison sample. The representative values are compared to the representative values in the comparison data. If there is sufficient similarity between the representative values found for the sample and the representative values in the comparison data corresponding to the same sample, then verification or identification is made. Sufficient similarity can be determined using any suitable statistical or other technique. For example, sufficient similarity might occur when some or all of the representative values match those in the verification matrix. In another example, this might occur when the sample falls below the threshold for each comparison sample. An alarm or output might be made via a user interface to advise the user of the result of the verification/identification.

Figure 15:
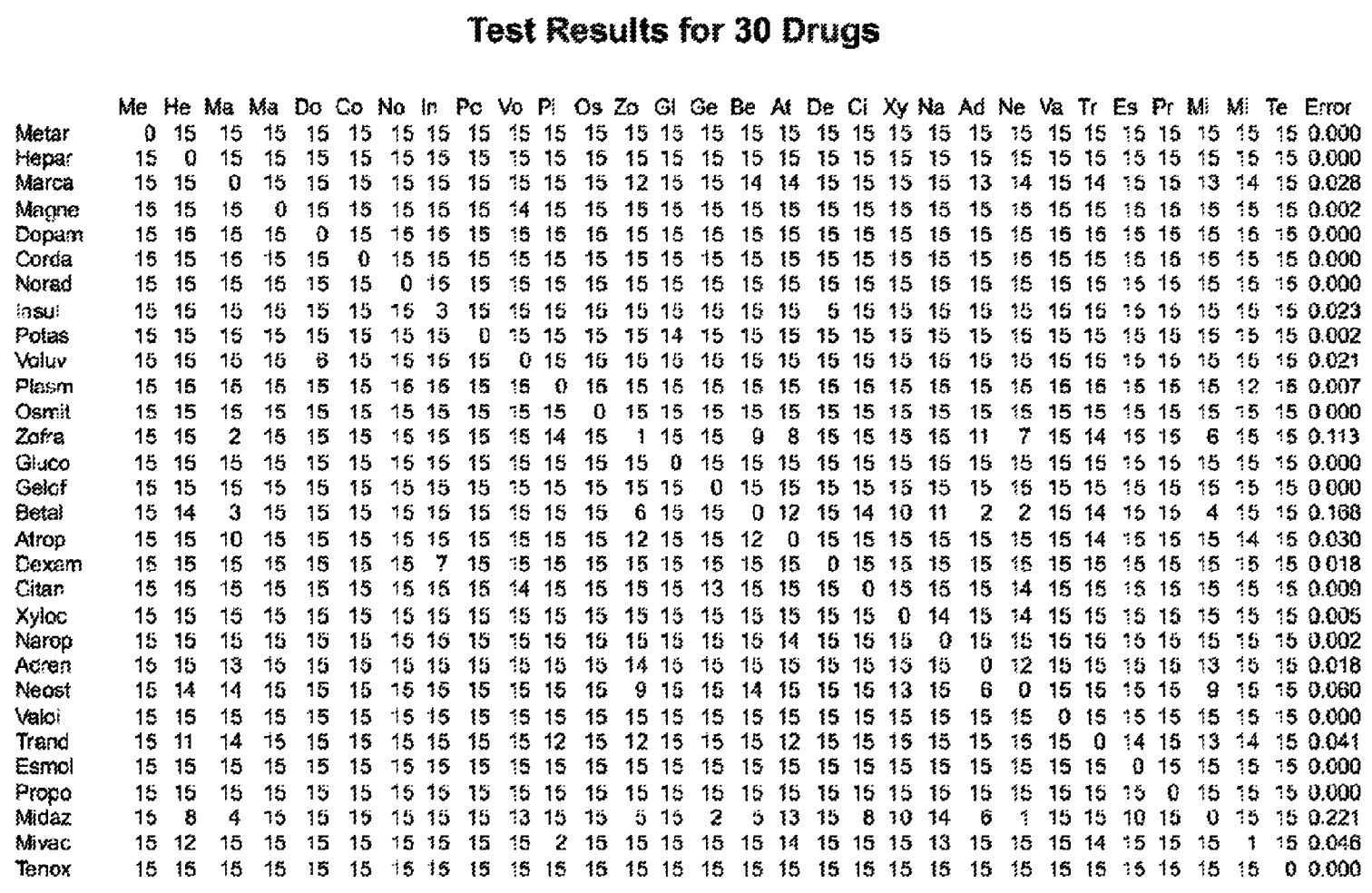

FIG. 15 shows test data for a set of 30 drugs verified using the analyser. In the test, each drug was inserted in the analyser, and then systematically the analyser was configured to check if it was one of the 30 drugs. If an alarm was raised, this indicated the drug was not the one that was anticipated, and the alarm noted. Each drug was tested 15 times, in relation to each of the other drugs. So, for example, Metaraminol was put into the analyser and then the analyser was configured to check for Metaraminol. After 15 tests, the analyser did not once raise an alarm, indicating that the analyser did not detect Metaraminol as another drug. Keeping Metaraminol in the sample retainer, the analyser was then configured to check for Heparin. For each of 15 independent tests, the analyser raised an alarm, indicating it detected each time that the drug in the analyser (Metaraminol) was not the drug it was expecting (Heparin). The analyser was then reconfigured for each of the other drugs, and the test done 15 times for each, while Metaraminol was in the sample retainer. The same process was then repeated for every other drug being used as a sample, with the analyser systematically being re-configured to check for every other drug. Each time an alarm was raised (indicating the analyser did not consider the drug in the retainer was that being checked form), the alarm was noted. The table in FIG. 15 reflects the number of times an alarm was raised of each drug detection combination. The error rates are shown. The low error rates demonstrate a significant improvement in verification accuracy.

Third Embodiment

Figure 12:
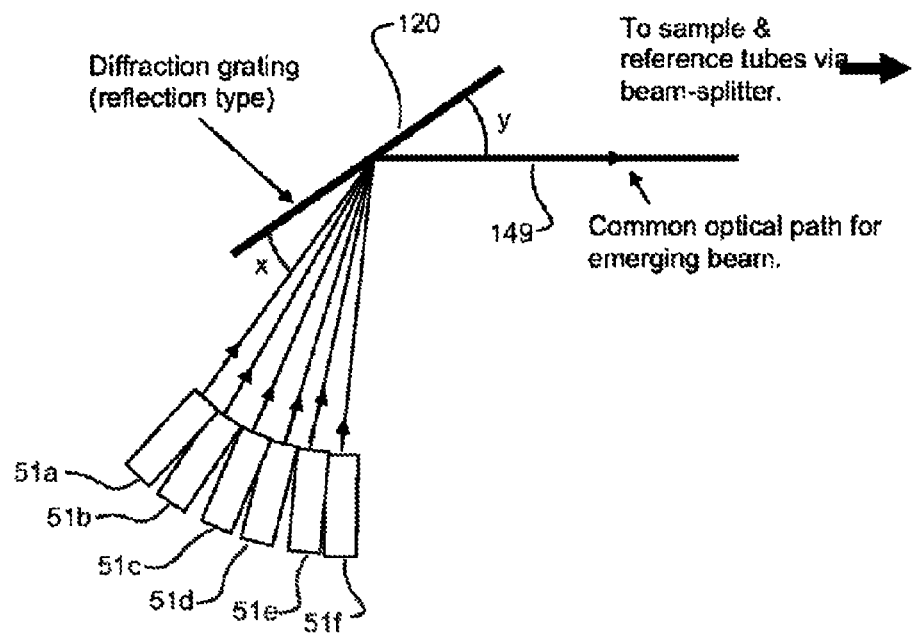
FIG. 12 shows a third embodiment in which the source comprises six lasers that are directed along the sample path 14*a* using a diffraction grating.
Figure 16:
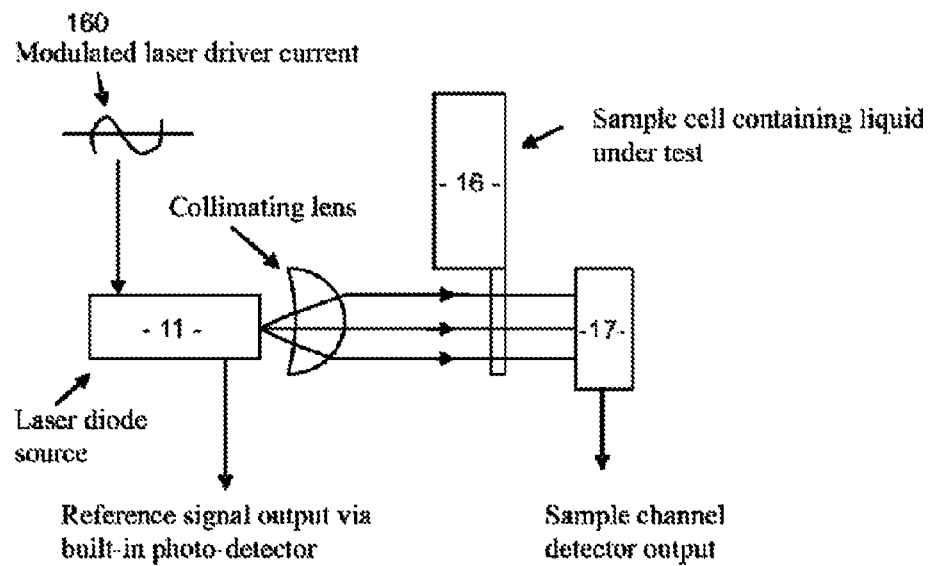
FIG. 16 shows an analyser using source modulation to eliminate a reference channel.

FIG. 12 shows an alternative embodiment of the apparatus 10. In this embodiment rather than using a carousel 50, the six lasers 51a-51f forming the source 11 are arranged to emit their electromagnetic radiation beam 22 towards a diffraction grating 120 of the reflection type. Each laser 51a-51f is operable to emit a tuned or tuneable wavelength of a collimated electromagnetic beam 22 towards the diffraction grating. The angle of incidence X on the grating surface for each laser 51a-51f is chosen that their first order diffracted beam emerges at the same angle Y thereby producing a common optical path 14a for each laser. The controller 12 activates each laser 51a-51f sequentially to emit a beam of a single wavelength towards the sample. Alternatively, multiple lasers 51a-51f could be operated at once such that an electromagnetic beam 22 comprising multiple wavelength components could be emitted towards the sample 16. A separate grating or beam splitter 21 could be used for example as shown in FIG. 1 to direct the beam towards a reference channel sample 19, if there is one. All other aspects of the embodiment can be as shown and described in FIGS. 1, 2, 16 and/or 18.

Fourth Embodiment

Figure 13:
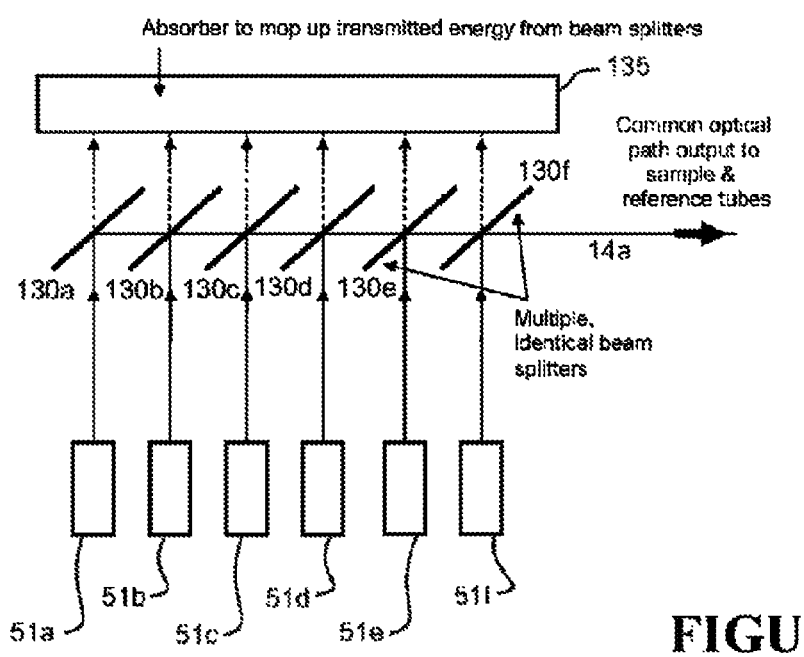
FIG. 13 shows a fourth embodiment comprising a source of six lasers the outputs of which are directed along a sample path using beam splitters.

FIG. 13 shows another alternative embodiment of the apparatus 10. In this embodiment rather than using a carousel 50, the six lasers 51a-51f forming the source 11 are arranged to emit their electromagnetic radiation beam 14a towards respective beam splitters 130a-130f that redirect the emitted electromagnetic radiation beam 22 along the sample path 14a. The controller 12 can control each electromagnetic radiation source 11 in turn to emit a tune or tuneable wavelength of electromagnetic radiation towards the sample via the respective beam splitter 130a-130f. Alternatively, two or more of the lasers 51a-51f could be activated at once to provide an electromagnetic beam 22 with multiple wavelength components towards 14a the sample 16. An absorber 135 is provided behind the beam splitter array to mop up transmitted energy from the beam splitters. A separate grating or beam splitter 21 could be used for example as shown in FIG. 1 to direct the beam towards a reference channel sample 19, if there is one. All other aspects of the embodiment can be as shown and described in FIGS. 1, 2, 16 and/or 18.

Fifth Embodiment

Figure 14:
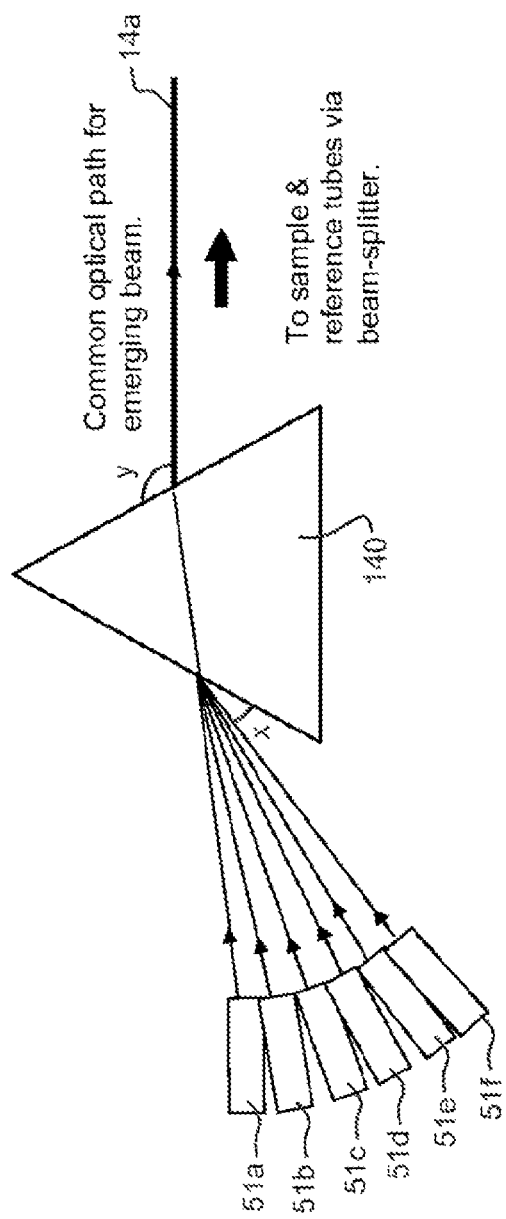
FIG. 14 shows in schematic form a fifth embodiment for the source comprising six lasers the outputs of which are converged onto a sample path using a prism.

FIG. 14 shows an alternative embodiment of the apparatus 10. In this embodiment rather than using a carousel 50, the six lasers 51a-51f forming the source 11 are arranged to emit their electromagnetic radiation beam 22 towards a prism 140. Each laser 51a-51f is operable to emit a tuned or tuneable wavelength of a collimated electromagnetic beam 14a towards the prism. The angle of incidence X on the grating surface for each laser 51a-51f is chosen that their first order refracted beam 22 emerges 14a at the same angle Y thereby producing a common optical path 14a for each laser 51a-51f. The controller 12 activates each laser 51a-51f sequentially to emit a beam of a single wavelength towards the sample. Alternatively, multiple lasers 51a-51f could be operated at once such that an electromagnetic beam 22 comprising multiple wavelength components could be emitted towards 14a the sample 16. A separate grating or beam splitter 21 could be used for example as shown in FIG. 1 to direct the beam towards a reference channel sample 19, if there is one. All other aspects of the embodiment can be as shown and described in FIGS. 1, 2, 16 and/or 18.

Sixth Embodiment

Figure 20:
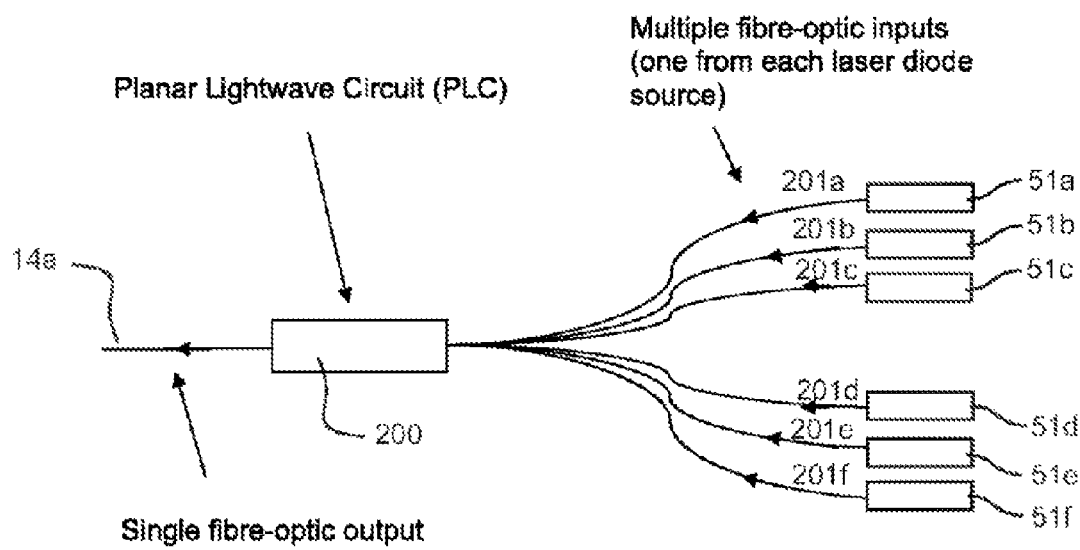
FIG. 20 shows in schematic form a sixth embodiment for the source comprising six lasers the outputs of which are converged onto a sample path using a planar lightwave circuit.

FIG. 20 shows an alternative embodiment of the apparatus 10. In this embodiment rather than using a carousel 50, the six lasers 51a-51f forming the source 11 are arranged to emit their electromagnetic radiation beam 22 through separate fibre optic cables 201a-201f towards a planar lightwave circuit (PLC) (fibre optic combiner) 200. Each laser 51a-51f is operable to emit a tuned or tuneable wavelength of a collimated electromagnetic beam 14a towards the PLC 200 via the fibre optic cables 201a-201f. The controller 12 activates each laser 51a-51f sequentially to emit a beam of a single wavelength towards the sample. Alternatively, multiple lasers 51a-51f could be operated at once such that an electromagnetic beam 22 comprising multiple wavelength components could be emitted towards 14a the sample 16. A separate grating or beam splitter 21 could be used for example as shown in FIG. 1 to direct the beam towards a reference channel sample 19, if there is one. All other aspects of the embodiment can be as shown and described in FIGS. 1, 2, 16 and/or 18.

Seventh Embodiment

Figure 21:
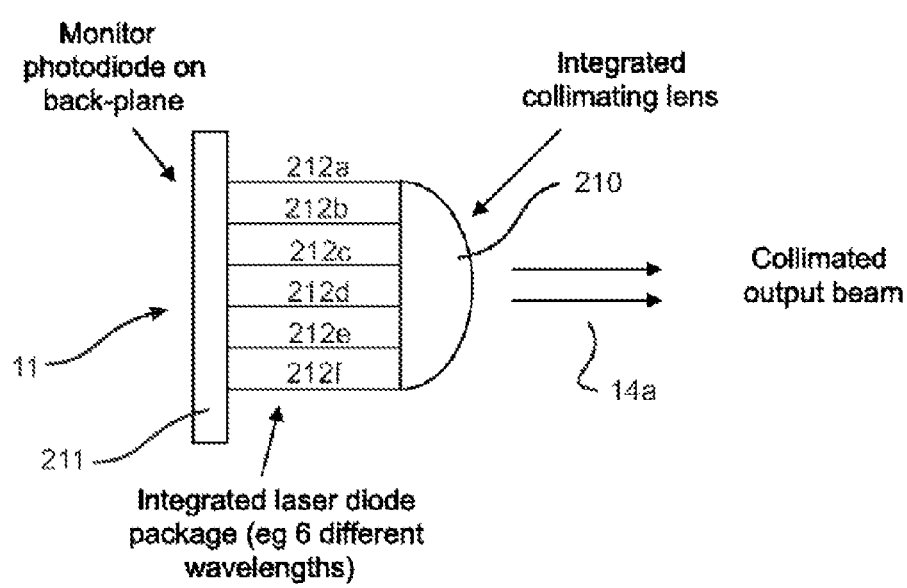
FIG. 21 shows in schematic form a seventh embodiment for the source comprising a single package source and collimated lens.

FIG. 21 shows an alternative embodiment of the apparatus 10. In this embodiment rather than using a carousel 50, a single package 211 comprising 6 lasers forming the source 11 are arranged to emit their electromagnetic radiation beam 201a-201f towards an integrated collimating lens 210. The laser is operable to emit a tuned or tuneable wavelength at each of 6 wavelengths towards the lens 210. The controller 12 activates the laser to sequentially to emit a beam 212a-212f of a single wavelength towards the sample. Alternatively, multiple beams 51a-51f could be operated at once such that an electromagnetic beam 22 comprising multiple wavelength components could be emitted towards 14a the sample 16 via the lens 210. A separate grating or beam splitter 21 could be used for example as shown in FIG. 1 to direct the beam towards a reference channel sample 19, if there is one. All other aspects of the embodiment can be as shown and described in FIGS. 1, 2, 16 and/or 18.

Alternative Embodiments

The nominal analysis range of 1300-2000 nm for selected wavelengths is chosen as it provides advantages for improved drug verification or identification. However, it will be appreciated that the reference to 1300-2000 nm should not be considered limiting, and wavelengths could be chosen that relate spectral characteristics in slightly different ranges or other ranges entirely. The selected wavelengths (and therefore the spectral characteristics) fall within any analysis range provide for improved identification/verification for drugs in the liquid carrier. For example, the analysis range could be a subset of 1300 nm-2000 nm, such as 1300 nm-1900 nm; 1350 nm-1950 nm; 1400 nm-1900 nm; 1500 nm-1800 nm or some other subset. The range could also be larger, such as 1250-2050 nm; 1200 nm-2100 nm; or 1150 nm-2150 nm or the like. The analysis range might even be offset from the nominal range, such as 1200 nm-1900 nm, or 1300 nm-1900 nm. These are non-limiting examples. In general, the analysis range could start, for example, anywhere from 1100 nm-1500 nm and end anywhere from 1800 nm-2150 nm. Even that is non-limiting and the range could be something different entirely that provides for improved verification/identification. Further, wavelengths falling outside these analysis ranges and corresponding to spectral features lying outside these analysis ranges above could also be used in combination with wavelengths falling in the analysis ranges mentioned. Using a plurality of wavelengths corresponding to spectral characteristics falling within the analysis range provides improved performance. Preferably any and all wavelengths are selected within the analysis range, but that does not preclude using wavelengths falling in other ranges also where that might be useful.

The range could be at least partially influenced by component selection. For example, silicon photodiodes have a response down to at least 1100 nm, so if used this wavelength might be used as the bottom end of the range. Preferably, the invention uses only one detector, so the range might be defined by what a single detector can cover—for example 1300 nm-2000 nm in the case of an InGaAs detector.

Other liquids to water might have other analysis ranges that provide improved identification/verification.

Other methods for extracting the information could be known and used by the skilled in the art.

In an alternative analysis process, a reference channel is not used. Rather, the detector output 14c from affected electromagnetic radiation (from the sample) acquired at an anchor wavelength is used, rather than the detector output 15c from affected electromagnetic radiation from the reference in the reference channel. All other detector output 14c from affected electromagnetic radiation received relating to other wavelengths is normalised/corrected using the detector output of affected electromagnetic radiation at the anchor wavelength. The anchor wavelength can be one of the wavelengths already selected, although preferably will be selected to be in the vicinity or within a region spanning a suitable spectral feature/point in the base liquid spectrum. For example, the anchor wavelength could be in the vicinity of or fall within a region spanning a stable region of the base liquid spectrum. Elimination of the reference channel/detector output removes variation between the sample and reference channels that can mask sample differences, thus removal creates a more sensitive and stable apparatus. The output at the anchor wavelength can be used to normalise, calibrate or otherwise adjust the output for the other wavelengths. The output from the anchor wavelength could be processed in the same manner as the output from the reference channel as describe previously in order to verify/analyse the sample. That is, the anchor output can become the reference information.

In one possibility, where water is the base liquid, 1450 nanometers is chosen as the anchor point as there is particular stability in the spectrum of water around this wavelength. This wavelength corresponds to the maximum optical absorption aqueous solutions due to the presence of OH bonds. It is a common transmission medium for sample drugs tested. Data acquired at this wavelength shows minimum thermal sensitivity and is therefore provides a highly stable and predictable reference. This is just one example for water based drug, and is indicative only and should not be considered limiting as to the wavelengths and anchor points that might be chosen based on other considerations.

Each of the previous embodiments describe the optional use of a reference channel to obtain reference measurements for use in processing data. In an alternative, the reference channel is not used. Rather, a photodiode 4 (see FIG. 20) in the laser diode 11 (which is used for power monitoring and control of the laser diode) can be utilised to obtain reference information. Laser diodes are often fitted with built-in photo-detector diodes 4 that are used to monitor the output power of the laser. This is done to stabilise the laser by allowing the laser driver current to be controlled via a feedback circuit incorporating the integrated photo-diode signal.

This alternative for obtaining reference information can be substituted in place of the reference channel for any of the embodiments described. The reference measurements obtained using the alternative can be utilised in the same manner as described any previous embodiment.

The output of the laser diode photodetector 4 which detects the output power of the source electromagnetic radiation is passed to the processor 18 and used instead of reference readings obtained by the reference detector 20 to normalise and/or correct the output from the detector 17 in the sample channel. This output signal from the photodetector 4 performs the same function as a reference channel that would otherwise have been produced more conventionally by using a beam splitter arrangement involving two separate measurement channels. Using the photo-diode output from the laser as a reference signal thereby eliminates the need for beam-splitting optics and an additional reference sample and detector.

In an alternative embodiment, the electromagnetic source 11 is a broadband source with multiple filters 13 at different wavelengths that can be arranged in between the broadband source and the sample. The output from each filter provides an electromagnetic beam 22 with one of the selected wavelengths. The broadband source could be, for example, a broadband filament blackbody source and filters. The source 11 could alternatively take the form of one or more LEDs with or without filters. Any of the alternative sources could be mounted on a carousel 50 and operated as described for the first embodiment, or operated in conjunction with an optical device such as described in embodiments two to four.

Any of the sources could be temperature stabilised with a feedback system, for example by using
thermistors and peltier cooling devices as previously described.

The detectors could be in the form of one or more InGaAs photodiodes or other light sensors.

A separate photodiode or similar or other detector could be used for each of the reference and sample channels. Alternatively, a single photodiode or similar or other detector could be used for both the sample and reference channels, utilising optical devices to merge the affected radiation beams of both channels, or otherwise direct them to the detector.

Random errors in measurements can be reduced by averaging detector readings over many measurements (e.g. 500). Dark measurements (source off) can be used to correct measured data.

For dark current readings, a chopper wheel can optionally be used that blacks out/blocks the electromagnetic radiation 22 incident on the sample 16 and the reference 20. The chopper could form part of the optical device 13. For each electromagnetic reading, the detector 17/20 also takes a "dark" reading when the chopper blocks the electromagnetic radiation 22. Having a chopper wheel and dark reading is not essential for the invention and is described here as one possible option.

Over the band 1300 nm to 2000 nm, it is also possible to use a single type of photo-diode detector based on indium gallium arsenide (InGaAs) technology which further simplifies the detector system.

The present invention preferably uses wavelengths in the analysis region of 1300 nm to 2000 nm or variations thereof. This region has previously been ignored for drug analysis due to the perceived disadvantage of broad spectral peaks and troughs that appear in the absorbance spectrum. Infrared (IR) spectroscopy previously has exploited the numerous narrow-band spectral absorption characteristics that exist for wavelengths longer than 2000 nm. This so-called 'fingerprint' region exhibits spectral lines that are characteristic of certain chemical bonds present in the material under test and offers a highly sensitive technique to identifying the material. The present inventors have determined that the 1300 nm-2000 nm analysis range (or portions thereof) provides an advantage for drug verification or identification or other analysis. Further, the inventors have established that the spectral location of salient spectral features in this analysis region is less affected by temperature variations. The numerous narrow spectral bands that appear in the region above 2000 nm exhibit large temperature sensitivity. If this region above 2000 nm is used for verification or identification, the analysis apparatus requires very precise wavelength resolution. This resolution can only be achieved using high-cost sophisticated spectrometers More particularly, this type of IR spectroscopic measurement (above 2000 nm) requires very fine wavelength resolution (typically a few nanometers) maintained over a wide spectral band in order to resolve the numerous individual spectral features. The fine wavelength resolution is especially required to account for any shift in the narrow spectral lines with respect to temperature variations.

The measurement of such highly resolved spectral lines requires the use of a spectrometer fitted with a sophisticated monochromator based either on a mechanically rotated diffraction grating and single detector, or a fixed grating with a linear array of detector elements. Both options are found in existing spectrometers and both are expensive to implement.

As a cost-effective alternative, aimed for example at water-based intravenous drug verification/identification or other analysis, it has been determined by the present inventors that it is advantageous to make measurements within the shorter wavelength region between 1300 nm and 2000 nm. Whilst the spectral characteristics/features in this wavelength region are much fewer in number and much broader spectrally (differing little from those of water), the inventors have found that there remain sufficient spectral differences between drugs (or other liquid based samples) to facilitate verification/identification. The have also found, that, in the 1300 nm to 2000 nm region, the wavelengths at which the peaks and troughs (and other spectral characteristics) of each drug's IR transmission spectrum occur remain highly stable with respect to temperature for all water-based drugs (or other samples).

Importantly, due to the absence of temperature-sensitive narrow spectral absorption features, they have established there is no requirement for highly resolved spectral lines to be measured thereby eliminating the need for an expensive monochromator. A small number of measurements (5 or 6 typically) made at discrete wavelengths over the range 1300 nm to 2000 nm is sufficient to characterise each drug (or other sample). Typically, each measurement is made over a bandwidth of 12 nm (as determined by a band-pass filter, illuminated by a broad-band source, for example) or over a few nanometers for laser-based illumination.

In general terms, a number of embodiments and variations are described above. It will be appreciated by those skilled in the art, combinations of the features of the various embodiments could be envisaged and the embodiments described should not be considered limiting

The invention claimed is:

1. An analyser for identifying or verifying a sample comprising:
   an electromagnetic radiation source for emitting electromagnetic radiation in at least one beam at a sample, the electromagnetic radiation comprising at least two different wavelengths, the source comprising multiple narrowband sources:
     integrated on a substrate,
     arranged on a carousel,
     arranged to emit radiation to a beam splitter,
     arranged to emit radiation to a prism, or
     arranged to emit radiation through separate fibre optic cables,
   a sample detector that detects affected electromagnetic radiation resulting from the emitted electromagnetic radiation affected by the sample and provides output representing the detected affected radiation,
   a processor for determining sample coefficients from the output, and identifying or verifying the sample using the sample coefficients and training coefficients determined from training samples,
   a modulator such that the emitted electromagnetic radiation at the sample is modulated electromagnetic radiation and prior to determining the sample coefficients the processor extracts the desired spectral component from the intensity at each of the at least two wavelengths to eliminate the dark current, and
   a temperature sensor to measure the temperature of the sample and provide temperature output to the processor, wherein the processor corrects the desired spectral components of the training coefficients at the at least two wavelengths to the temperate of the sample,
   wherein the temperature is corrected according to:

$$I(T_t) = I(T_b) + \frac{dI}{dT}\Delta T \quad (1)$$

where,
I is the intensity of affected electromagnetic radiation detected by a detector at a particular wavelength for a sample,
$T_t$ is the temperature of the training sample when the affected electromagnetic radiation was detected at that wavelength,
$T_b$ is the temperature of the unknown sample when the affected electromagnetic radiation was detected at that wavelength,
$\Delta T = T_t - T_b$ is the sample temperature difference between the training sample temperature and unknown sample temperature, and $$\frac{dI}{dT}$$

is the slope or the linear relationship of between measure intensity and temperature for a sample at a given wavelength.

2. An analyser according to claim 1 wherein prior to determining the training coefficients the desired spectral components are extracted by the processor from the intensity at each of the at least two wavelengths to eliminate the dark current.

3. An analyser according to claim 2 wherein the processor extracts the desired spectral component by multiplying the output representing the detected affected modulated electromagnetic radiation by sine and cosine functions and integrating over the period of modulation oscillation to remove the dark current component.

4. An analyser according to claim 3 wherein the processor extracts the desired spectral component by conducting a Fourier Transform on the output representing the modulated detected affected radiation and removing the dark current component from the transformed output.

5. An analyser for identifying or verifying a sample comprising:
   an electromagnetic radiation source for emitting electromagnetic radiation in at least one beam at a sample, the electromagnetic radiation comprising at least two different wavelengths, wherein:
     the source is broadband source with multiple filters at different wavelengths that can be arranged in between the broadband source and the sample. The output from each filter provides an electromagnetic beam with one of the selected wavelengths,
   a sample detector that detects affected electromagnetic radiation resulting from the emitted electromagnetic radiation affected by the sample and provides output representing the detected affected radiation,
   a processor for determining sample coefficients from the output, and identifying or verifying the sample using the sample coefficients and training coefficients determined from training samples,
   a modulator such that the emitted electromagnetic radiation at the sample is modulated electromagnetic radiation and prior to determining the sample coefficients the processor extracts the desired spectral component from the intensity at each of the at least two wavelengths to eliminate the dark current,
   a temperature sensor to measure the temperature of the sample and provide temperature output to the processor, wherein the processor corrects the desired spectral components of the training coefficients at the at least two wavelengths to the temperate of the sample.

6. An analyser for identifying or verifying a sample comprising:
   an electromagnetic radiation source for emitting electromagnetic radiation in at least one beam at a sample, the electromagnetic radiation comprising at least two different wavelengths, wherein the source is laser diode with a photodiode, a sample detector that detects affected electromagnetic radiation resulting from the emitted electromagnetic radiation affected by the sample and provides output representing the detected affected radiation, a processor for determining sample coefficients from the output, and identifying or verifying the sample using the sample coefficients and training coefficients determined from training samples, a modulator such that the emitted electromagnetic radiation at the sample is modulated electromagnetic radiation and prior to determining the sample coefficients the processor extracts the desired spectral component from the intensity at each of the at least two wavelengths to eliminate the dark current, a temperature sensor to measure the temperature of the sample and provide temperature output to the processor, wherein the processor corrects the desired spectral components of the training coefficients at the at least two wavelengths to the temperate of the sample, wherein the output of the laser diode photodetector relates to the output power of the source electromagnetic radiation and is passed to the processor and used instead of reference readings to normalise and/or correct the output from the sample detector.

* * * * *